US007705138B2

(12) United States Patent
Lin et al.

(10) Patent No.: US 7,705,138 B2
(45) Date of Patent: Apr. 27, 2010

(54) HEPATITIS C VIRUS VARIANTS

(75) Inventors: Chao Lin, Winchester, MA (US); Tara Kieffer, Brookline, MA (US); Christoph Sarrazin, Hamburg (DE); Ann Kwong, Cambridge, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

(21) Appl. No.: 11/599,162

(22) Filed: Nov. 13, 2006

(65) Prior Publication Data

US 2007/0231262 A1    Oct. 4, 2007

Related U.S. Application Data

(60) Provisional application No. 60/854,598, filed on Oct. 25, 2006, provisional application No. 60/735,577, filed on Nov. 11, 2005.

(51) Int. Cl.
*C12N 15/57* (2006.01)
*C12N 15/51* (2006.01)
*C12N 15/74* (2006.01)
*C12N 15/79* (2006.01)
*C12N 9/50* (2006.01)
*C12P 19/34* (2006.01)

(52) U.S. Cl. .................. 536/23.2; 435/69.1; 435/91.21; 435/219; 435/252.3; 435/320.1; 536/23.1; 536/23.72

(58) Field of Classification Search ........................ None
See application file for complete search history.

(56) References Cited

U.S. PATENT DOCUMENTS

| 4,835,168 | A | 5/1989 | Paget et al. |
| 5,484,801 | A | 1/1996 | Al-Razzak et al. |
| 5,631,128 | A | 5/1997 | Kozal et al. |
| 5,807,876 | A | 9/1998 | Armistead et al. |
| 5,866,684 | A | 2/1999 | Attwood et al. |
| 5,948,436 | A | 9/1999 | Al-Razzak et al. |
| 5,990,276 | A | 11/1999 | Zhang et al. |
| 6,018,020 | A | 1/2000 | Attwood et al. |
| 6,037,157 | A | 3/2000 | Norbeck et al. |
| 6,054,472 | A | 4/2000 | Armistead et al. |
| 6,127,422 | A | 10/2000 | Colacino et al. |

(Continued)

FOREIGN PATENT DOCUMENTS

WO    WO 92/03918    3/1992

(Continued)

OTHER PUBLICATIONS

Kieffer, T. L., et al., 2007, "Telaprevir and pegylated interferon-alpha-2a inhibit wild-type and resistant genotype hepatitis C virus replication in patients", Hepatology, vol. 46, pp. 631-639.*

(Continued)

*Primary Examiner*—Nashaat T Nashed
*Assistant Examiner*—William W Moore
(74) *Attorney, Agent, or Firm*—Rogers & Gray LLP

(57) ABSTRACT

The present invention relates to HCV variants, particularly variants that are resistant to a protease inhibitors such as VX-950. Also provided are methods and compositions related to the HCV variants. Further provided are methods of isolating, identifying, and characterizing multiple viral variants from a patient.

28 Claims, 33 Drawing Sheets

V36M and R155K Substitutions Are Additive in Conferring Resistance to Telaprevir

Replicon $IC_{50}$

Fold change: WT = 1, V36M = 7, R155K = 7, V36M+R155K = 63

Enzyme $K_i$

Fold change: WT = 1, V36M = 6, R155K = 11, V36M+R155K = 74

VERTEX

U.S. PATENT DOCUMENTS

| | | | |
|---|---|---|---|
| 6,162,613 | A | 12/2000 | Su et al. |
| 6,258,558 | B1 | 7/2001 | Szostak et al. |
| 6,265,380 | B1 | 7/2001 | Tung et al. |
| 6,344,465 | B1 | 2/2002 | Armistead et al. |
| 6,361,943 | B1 | 3/2002 | Yanagawa et al. |
| 6,489,098 | B1 | 12/2002 | Petropoulos et al. |
| 6,498,178 | B2 | 12/2002 | Stamos et al. |
| 6,538,126 | B1 * | 3/2003 | Cho et al. ............... 536/23.72 |
| 6,541,496 | B1 | 4/2003 | Armistead et al. |
| 6,608,027 | B1 | 8/2003 | Tsantrizos et al. |
| 6,617,130 | B1 | 9/2003 | Bogosian et al. |
| 6,617,156 | B1 | 9/2003 | Doucette-Stamm et al. |
| 6,838,475 | B2 | 1/2005 | Arasappan et al. |
| 6,846,802 | B2 | 1/2005 | Chen et al. |
| 6,849,254 | B1 | 2/2005 | Brass et al. |
| 6,911,428 | B2 | 6/2005 | Zhu et al. |
| 6,914,122 | B2 | 7/2005 | Venkatraman et al. |
| 6,924,270 | B2 | 8/2005 | Ganguly et al. |
| 6,962,932 | B2 | 11/2005 | Blume et al. |
| 7,208,309 | B2 * | 4/2007 | Kukolj et al. ............... 435/219 |
| 2002/0016294 | A1 | 2/2002 | Venkatraman et al. |
| 2002/0016442 | A1 | 2/2002 | Llinas-brunet et al. |
| 2002/0032175 | A1 | 3/2002 | Tung et al. |
| 2002/0147139 | A1 | 10/2002 | Zhu et al. |
| 2002/0177725 | A1 | 11/2002 | Priestley |
| 2003/0008828 | A1 | 1/2003 | Priestley et al. |
| 2003/0162169 | A1 | 8/2003 | Pellerin et al. |
| 2003/0207861 | A1 | 11/2003 | Arasappan et al. |
| 2003/0216325 | A1 | 11/2003 | Saksena et al. |
| 2003/0236242 | A1 | 12/2003 | Perni et al. |
| 2004/0018986 | A1 | 1/2004 | Pitlik et al. |
| 2004/0077600 | A1 | 4/2004 | Tung et al. |
| 2004/0142876 | A1 | 7/2004 | Colarusso et al. |
| 2004/0147483 | A1 | 7/2004 | Priestley |
| 2004/0214994 | A1 | 10/2004 | Burioni et al. |
| 2005/0059606 | A1 | 3/2005 | Saksena et al. |
| 2005/0080017 | A1 | 4/2005 | Cottrell et al. |
| 2005/0085425 | A1 | 4/2005 | Chen et al. |
| 2005/0090450 | A1 | 4/2005 | Farmer et al. |
| 2005/0107304 | A1 | 5/2005 | Britt et al. |
| 2005/0119168 | A1 | 6/2005 | Venkatraman et al. |
| 2005/0136400 | A1 * | 6/2005 | Lin et al. ............... 435/5 |
| 2005/0143439 | A1 | 6/2005 | Blume et al. |
| 2005/0153900 | A1 | 7/2005 | Velazquez et al. |
| 2005/0164921 | A1 | 7/2005 | Njoroge et al. |
| 2005/0176648 | A1 | 8/2005 | Saksena et al. |
| 2005/0197301 | A1 | 9/2005 | Njoroge et al. |
| 2005/0209164 | A1 | 9/2005 | Bogen et al. |
| 2005/0222047 | A1 | 10/2005 | Chen et al. |
| 2005/0245458 | A1 | 11/2005 | Arasappan et al. |
| 2005/0249702 | A1 | 11/2005 | Njoroge et al. |
| 2007/0292840 | A1 * | 12/2007 | Lemon et al. ............... 435/5 |
| 2009/0215869 | A1 * | 8/2009 | Sallberg ............... 514/44 R |

FOREIGN PATENT DOCUMENTS

| | | |
|---|---|---|
| WO | WO 94/14436 | 7/1994 |
| WO | WO 95/07696 | 3/1995 |
| WO | WO 95/09614 | 4/1995 |
| WO | WO 97/40028 | 10/1997 |
| WO | WO 97/43310 | 11/1997 |
| WO | WO 98/11134 | 3/1998 |
| WO | WO 98/12308 * | 3/1998 |
| WO | WO 98/17679 | 4/1998 |
| WO | WO 98/22496 | 5/1998 |
| WO | WO 98/40381 | 9/1998 |
| WO | WO 98/46630 | 10/1998 |
| WO | WO 99/07733 | 2/1999 |
| WO | WO 99/07734 | 2/1999 |
| WO | WO 99/38888 | 8/1999 |
| WO | WO 99/50230 | 10/1999 |
| WO | WO 99/64442 | 12/1999 |
| WO | WO 00/09543 | 2/2000 |
| WO | WO 00/09558 | 2/2000 |
| WO | WO 00/31129 | 6/2000 |
| WO | WO 00/56331 | 9/2000 |
| WO | WO 00/59929 | 10/2000 |
| WO | WO 01/07407 | 2/2001 |
| WO | WO 01/64678 | 9/2001 |
| WO | WO 01/74768 | 10/2001 |
| WO | WO 01/77113 | 10/2001 |
| WO | WO 01/81325 | 11/2001 |
| WO | WO 02/08187 | 1/2002 |
| WO | WO 02/08198 | 1/2002 |
| WO | WO 02/08244 | 1/2002 |
| WO | WO 02/08256 | 1/2002 |
| WO | WO 02/18369 | 3/2002 |
| WO | WO 02/48116 | 6/2002 |
| WO | WO 02/48157 | 6/2002 |
| WO | WO 02/060926 | 8/2002 |
| WO | WO 02/068933 | 9/2002 |
| WO | WO 02/079234 | 10/2002 |
| WO | WO 03/006490 | 1/2003 |
| WO | WO 03/014381 * | 2/2003 |
| WO | WO 2004/039970 | 5/2004 |
| WO | WO 2004/072243 | 8/2004 |
| WO | WO 2005/012502 * | 2/2005 |
| WO | WO 2006/112482 A1 | 10/2006 |
| WO | WO 2007/031867 A2 | 3/2007 |

OTHER PUBLICATIONS

Okamoto, H., et al., 1982, "Full-Length Sequence of a Hepatitis C Virus Genome Having Poor Homology to Reported Isolates: Comparative Study of Four Distinct Genotypes", Virology, vol. 188, pp. 331-341.*

Chamberlain, R. W., et al., 1997, "The Complete Coding Sequence of Hepatitis C Virus Genotype 5a, the Predominant Genotype in South Africa", Biochemical and Biophysical Research Communications, vol. 236, pp. 44-49.*

Vallet, S. et al., 2005, "Genetic Heterogeneity of the NS3 Protease Gene in Hepatitis C Virus Genotype 1 From Untreated Infected Patients", Journal of Medical Virology, vol. 75, pp. 528-537.*

Holland-Staley, C., et al., "Genetic Diversity and Response to IFN of the NS3 Protease Gene from Clinical Strains of the Hepatitis C Virus," *Archives of Virology*, vol. 147:1385-1406, 2002.

Lin, C. et al., "In Vitro Resistance Studies of Hepatitis C Virus Serine Protease Inhibitors, VX-950 and BILN 2061," *Journal of Biological Chemistry*, vol. 279(17):17508-17514, 2004.

Lin, C. et al., "In Vitro Studies of Cross-resistance Mutations against Two Hepatitis C Virus Serine Protese Inhibitors, VX-950 and BILN 2061," *Journal of Biological Chemistry*, vol. 280(44):36784-36791, 2005.

Sarrazin, C. et al., "Clinical Significance of In Vitro Replication—Enhancing Mutations of the Hepatitis C Virus (HCV) Replicon in Patients with Chronic HCV Infection," *Journal of Infectious Diseases*, vol. 192:1710-1719, 2005.

Sarrazin, C. et al., "Dynamic Hepatitis C Virus Genotypic and Phenotypic Changes in Patients Treated With the Protease Inhibitor Telaprevir," *Gastroenterology*, vol. 132:1767-1777, 2007.

Ueno, T. et al., "Isolation and Characterization of Monoclonal Antibodies That Inhibit Hepatitis C Virus NS3 Protease," *Journal of Virology*, vol. 74(14):6300-6308, 2000.

"Nucleosides," *Carbohydrate Chemistry*, Chapter 20:242-276 (1993), Ferrier et al., Eds .

Alberti et al., "Natural history of hepatitis C," *Journal of Hepatology*, 31(1):17-24 (1999).

Alter et al, "The epidemiology of viral hepatitis in the United States," *Gastroenterology Clinics of North America*, 23(3):437-455 (1994).

Alter et al., "Recovery, persistence, and sequelae in hepatitis C virus infection: a perspective on long-term outcome" *Seminars in Liver Disease*, 20(1):17-35 (2000).

Alter, "Hepatitis C virus infection in the United States," *Journal of Hepatology*, 31(1):88-91 (1999).

Barbato et al., "The solution structure of the N-terminal proteinase domain of the hepatitis C virus (HCV) NS3 protein provides new insights into its activation and catalytic mechanism," *Journal of Molecular Biology*, 289(2):371-384 (1999).

Bartenschlager et al., "Complex formation between the NS3 serine-type proteinase of the hepatitis C virus and NS4A and its importance for polyprotein maturation." *Journal of Virology*, 69(12):7519-7528 (1995).

Bartenschlager et al., "Kinetic and structural analyses of hepatitis C virus polyprotein processing," *Journal of Virology*, 68(8):5045-5055 (1994).

Bartenschlager et al., "Nonstructural protein 3 of the hepatitis C virus encodes a serine-type proteinase required for cleavage at the NS3/4 and NS4/5 junctions," *Journal of Virology*, 67(7):3835-3844 (1993).

Behrens et al., "Identification and properties of the RNA-dependent RNA polymerase of hepatitis C virus," *The EMBO Journal*, 15(1):12-22 (1996).

Beyer et al., "Effect of naturally occurring active site mutations on hepatitis C virus NS3 protease specificity," *Proteins* 43(2):82-88 (2001).

Blight et al., "Efficient initiation of HCV RNA replication in cell culture," *Science*, 290(5498):1972-1974 (2000).

Blight et al., "Molecular virology of hepatitis C virus: an update with respect to potential antiviral targets," *Antiviral Therapy*, 3(3):71-81 (1998).

Casbarra et al., "The effect of prime-site occupancy on the hepatitis C virus NS3 protease structure," *Protein Science*, 11(9):2102-2112 (2002).

Chambers et al., "Evidence that the N-terminal domain of nonstructural protein NS3 from yellow fever virus is a serine protease responsible for site-specific cleavages in the viral polyprotein," *PNAS*, 87(22):8898-8902 (1990).

Chander et al., "Treatment of chronic hepatitis C: a systematic review," *Hepatology*, 36 (5 Suppl 1):S135-S144 (2002).

Choo et al., "Genetic organization and diversity of the hepatitis C virus," *PNAS*, 88(6):2451-2455 (1991).

Choo et al., "Isolation of a cDNA clone derived from a blood-borne non-A, non-B viral hepatitis genome," *Science*, 244(4902):359-362 (1989).

Clayette et al., "IFN-tau, a new interferon type I with antiretroviral activity," *Pathology-Biology*, 47(5):553-559 (1999), English abstract only.

Colacino et al., "Evaluation of the anti-influenza virus activities of 1,3,4-thiadiazol-2-ylcyanamide (LY217896) and its sodium salt," *Antimicrobial Agents and Chemotherapy*, 34(11):2156-2163 (1990).

Davis et al., "Future options for the management of hepatitis C," *Seminars in Liver Disease*, 19(1):103-112 (1999).

Davis et al., "Interferon alfa-2b alone or in combination with ribavirin for the treatment of relapse of chronic hepatitis C. International Hepatitis Interventional Therapy Group," *New England Journal of Medicine*, 339(21):1493-1499 (1998).

De Francesco et al., "Approaching a new era for hepatitis C virus therapy: inhibitors of the NS3-4A serine protease and the NS5B RNA-dependent RNA polymerase," *Antiviral Research*, 58(1):1-16 (2003).

De Francesco et al., "Structure and function of the hepatitis C virus NS3-NS4A serine proteinase," *Current Topics in Microbiology and Immunology*, 242:149-169 (2000).

Di Marco et al., "Inhibition of the hepatitis C virus NS3/4A protease. The crystal structures of two protease-inhibitor complexes," *The Journal of Biological Chemistry*, 275(10):7152-7157 (2000).

Dunsdon et al., "Solid phase synthesis of aminoboronic, acids: potent inhibitors of the hepatitis C virus NS3 proteinase," *Bioorganic and Medicinal Chemistry Letters*, 10(14):1577-1579 (2000).

Failla et al., "An amino-terminal domain of the hepatitis C virus NS3 protease is essential for interaction with NS4A," *Journal of Virology*, 69(3):1769-1777 (1995).

Frese et al., "Interferon-alpha inhibits hepatitis C virus subgenomic RNA replication by an MxA-independent pathway," *Journal of General Virology*, 82(Pt 4):723-733 (2001).

Gish et al., "Recent developments in the treatment of chronic hepatitis B virus infection," *Expert Opinion on Investigational Drugs*, 4(2):95-115 (1995).

Grakoui et al., "A second hepatitis C virus-encoded proteinase," *PNAS*, 90(22):10583-10587 (1993).

Grakoui et al., "Characterization of the hepatitis C virus-encoded serine proteinase: determination of proteinase-dependent polyprotein cleavage sites," *Journal of Virology*, 67(5):2832-2843 (1993).

Grakoui et al., "Expression and identification of hepatitis C virus polyprotein cleavage products," *Journal of Virology*, 67(3):1385-1395 (1993).

Han et al., "Alpha-ketoamides, alpha-ketoesters and alpha-diketones as HCV NS3 protease inhibitors," *Bioorganic and Medicinal Chemistry Letters*, 10(8):711-713 (2000).

Hijikata et al., "Proteolytic processing and membrane association of putative nonstructural proteins of hepatitis C virus," *PNAS*, 90(22):10773-10777 (1993).

Hijikata et al., "Two distinct proteinase activities required for the processing of a putative nonstructural precursor protein of hepatitis C virus," *Journal of Virology*, 67(8):4665-4675 (1993).

Hirsch et al., "Antiretroviral drug resistance testing in adults infected with human immunodeficiency virus type I: 2003 recommendations of an International AIDS Society-USA Panel," *Clinical Infectious Diseases*, 37(1):113-128 (2003).

Iwarson, "The natural course of chronic hepatitis C," *FEMS Microbiolog Reviews*, 14(3):201-204 (1994).

Janssen et al., "Suicide associated with alfa-interferon therapy for chronic viral hepatitis," *Journal of Hepatology*, 21(2):241-243 (1994).

Johnson et al., "Update of the Drug Resistance Mutations in HIV-1: 2004," *Topics in HIV Medicine*, 12(4):119-124 (2004).

*Journal of Viral Hepatitis*, "Global surveillance and control of hepatitis C. Report of a WHO Consultation organized in collaboration with the Viral Hepatitis Prevention Board, Antwerp, Belgium", 6(1):35-47 (1999).

Kao et al., "Efficacy of consensus interferon in the treatment of chronic hepatitis C," *Journal of Gastroenterology and Hepatology*,15(12):1418-1423 (2000).

Kato et al., "Molecular cloning of the human hepatitis C virus genome from Japanese patients with non-A, non-B hepatitis," *PNAS*, 87(24):9524-9528 (1990).

Kenny-Walsh, "The natural history of hepatitis C virus infection," *Clinics in Liver Disease*, 5(4):969-977 (2001).

Kers et al., "Nucleoside phosphates, development of synthetic methods and reagents," *Nucleosides & Nucleotides*, 15(1-3):361-378 (1996).

Kew, "Hepatitis C virus and hepatocellular carcinoma," *FEMS Microbiology Reveiws*, 14(3):211-219 (1994).

Kim et al., "Crystal structure of the hepatitis C virus NS3 protease domain complexed with a synthetic NS4A cofactor peptide," *Cell*, 87(2):343-355 (1996).

Kim et al., "C-terminal domain of the hepatitis C virus NS3 protein contains an RNA helicase activity," *Biochemical and Biophysical Research Communications*, 215(1):160-166 (1995).

Koch et al., "Determinants of Substrate Specificity in the NS3 Serine Proteinase of the Hepatitis C Virus", *Virology*, 237:78-88 (1997).

Kolykhalov et al., "Hepatitis C virus-encoded enzymatic activities and conserved RNA elements in the 3' nontranslated region are essential for virus replication in vivo," *Journal of Virology*, 74(4):2046-2051 (2000).

Kolykhalov et al., "Transmission of hepatitis C by intrahepatic inoculation with transcribed RNA," *Science*, 277(5325):570-574 (1997).

Krieger et al., "Enhancement of hepatitis C virus RNA replication by cell culture-adaptive mutations," *Journal of Virology*, 75(10):4614-4624 (2001).

Lahm et al., "Hepatitis C virus proteins as targets for drug development: the role of bioinformatics and modelling," *Current Drug Targets*, 3(4):281-296 (2002).

Lai et al., "Prevalence and clinical correlates of YMDD variants during lamivudine therapy for patients with chronic hepatitis B," *Clinical Infectious Diseases*, 36(6):687-696 (2003).

Lamarre et al., "An NS3 protease inhibitor with antiviral effects in humans infected with hepatitis C virus," *Nature*, 426(6963):186-189 (2003).

Landro et al., "Mechanistic role of an NS4A peptide cofactor with the truncated NS3 protease of hepatitis C virus: elucidation of the NS4A stimulatory effect via kinetic analysis and inhibitor mapping," *Biochemistry*, 36(31):9340-9348 (1997).

LaPlante et al., "NMR line-broadening and transferred NOESY as a medicinal chemistry tool for studying inhibitors of the hepatitis C virus NS3 protease domain," *Bioorganic and Medical Chemistry Letters*, 10(20):2271-2274 (2000).

Lin et al., "A central region in the hepatitis C virus NS4A protein allows formation of an active NS3-NS4A serine proteinase complex in vivo and in vitro," *Journal of Virology*, 69(7):4373-4380 (1995).

Lin et al., "Hepatitis C virus NS3 serine proteinase: trans-cleavage requirements and processing kinetics," *Journal of Virology*, 68(12):8147-8157 (1994).

Lin et al., "In vitro studies of cross-resistance mutations against two hepatitis C virus serine protease inhibitors, VX-950 and BILN 2061," *Journal of Biological Chemistry*, 280(44):36784-36791 (2005).

Lin et al., "The hepatitis C virus NS3 serine proteinase and NS4A cofactor: establishment of a cell-free trans-processing assay," *PNAS*, 92(17):7622-7626 (1995).

Llinas-Brunet et al., "Highly potent and selective peptide-based inhibitors of the hepatitis C virus serine protease: towards smaller inhibitors," *Bioorganic and Medicinal Chemistry Letters*, 10(20):2267-2270 (2000).

Llinas-Brunet et al., "Peptide-based inhibitors of the hepatitis C virus serine protease," *Bioorganic and Medicinal Chemistry Letters*, 8(13):1713-1718 (1998).

Lohmann et al., "Mutations in hepatitis C virus RNAs conferring cell culture adaptation," *Journal of Virology*, 75(3):1437-1449 (2001).

Lohmann et al., "Replication of subgenomic hepatitis C virus RNAs in a hepatoma cell line," *Science*, 285(5424):110-113 (1999).

Love et al., "The crystal structure of hepatitis C virus NS3 proteinase reveals a trypsin-like fold and a structural zinc binding site," *Cell*, 87(2):331-342 (1996).

Lu et al.,"Mutations conferring resistance to a potent hepatitis C virus serine protease inhibitor in vitro" *Antimicrobial Agents and Chemotherapy*, 48(6):2260-2266 (2004).

Markland et al., "Broad-spectrum antiviral activity of the IMP dehydrogenase inhibitor VX-497: a comparison with ribavirin and demonstration of antiviral additivity with alpha interferon," *Antimicrobial Agents and Chemotherapy*, 44(4):859-866 (2000).

McCoy et al., "Solution structure and dynamics of the single-chain hepatitis C virus NS3 protease NS4A cofactor complex," *Journal of Molecular Biology*, 305(5):1099-1110 (2001).

McHutchison et al., "Future therapy of hepatitis C," *Hepatology*, 36 (5 Suppl 1):S245-S252 (2002).

McHutchison et al., "Interferon alfa-2b alone or in combination with ribavirin as initial treatment for chronic hepatitis C. Hepatitis Interventional Therapy Group," *New England Journal of Medicine*, 339(21):1485-1492 (1998).

Migliaccio et al., "Characterization of resistance to non-obligate chain-terminating ribonucleoside analogs that inhibit hepatitis C virus replication in vitro," *Journal of Biological Chemistry*, 278(49):49164-49170 (2003).

Moradpour et al., "Current and evolving therapies for hepatitis C," *European Journal of Gastroenterology and Hepatology*, 11(11):1199-1202 (1999).

Morrison, "Kinetics of the reversible inhibition of enzyme-catalysed reactions by tight-binding inhibitors," *Biochimica et Blophysica Acta*, 185(2):269-286 (1969).

Neumann et al., "Hepatitis C viral dynamics in vivo and the antiviral efficacy of interferon-alpha therapy," *Science*, 282(5386):103-107 (1998).

Nguyen et al., "Resistance profile of a hepatitis C virus RNA-dependent RNA polymerase benzothiadiazine inhibitor," *Antimicrobial Agents and Chemotherapy*, 47(11):3525-3530 (2003).

Pause et al., "An NS3 serine protease inhibitor abrogates replication of subgenomic hepatitis C virus RNA," *Journal of Biological Chemistry*, 278(22):20374-20380 (2003).

Pawlotsky et al., "Hepatitis C. Development of new drugs and clinical trials: promises and pitfalls. Summary of an AASLD hepatitis single topic conference," *Hepatology*, 39(2):554-567 (2004).

Perni et al., "Inhibitors of hepatitis C virus NS3.4A protease 2. Warhead SAR and optimization," *Bioorganic and Medicinal Chemistry Letters*, 14:1441-1446 (2004).

Pietschmann et al., "Characterization of cell lines carrying self-replicating hepatitis C virus RNAs," *Journal of Virology*, 75(3):1252-1264 (2001).

Reddy et al., "Efficacy and safety of pegylated (40-kd) interferon alpha-2a compared with interferon alpha-2a in noncirrhotic patients with chronic hepatitis C," *Hepatology*, 33(2):433-438 (2001).

Renault et al., "Side effects of alpha interferon," *Seminars in Liver Disease*, 9(4):273-277 (1989).

Rice, "Flavivirdae: The Viruses and Their Replication" *Fields Virology*, Third Edition, Chapter 30:31-959 (1996).

Saito et al., "Hepatitis C virus infection is associated with the development of hepatocellular carcinoma," *PNAS*, 87(17):6547-6549 (1990).

Sauder, "Immunomodulatory and pharmacologic properties of imiquimod," *Journal of the American Academy of Dermatology*, 43(I Pt 2):S6-S11 (2000).

Simmonds, "Genetic diversity and evolution of hepatitis C virus—15 years on," *Journal of General Virology*, 85:3173-3188 (2004).

Weiland, "Interferon therapy in chronic hepatitis C virus infection," *FEMS Microbiology Reviews*, 14(3):279-288 (1994).

Wilson et al., "Nitrogen Glycosylation reactions involving pyrimidine and purine nucleodise bases with furanoside sugars," *Synthesis*, 1465-1479 (1995).

Yan et al., "Complex of NS3 protease and NS4A peptide of BK strain hepatitis C virus: a 2.2 A resolution structure in a hexagonal crystal form," *Protein Science*, 7(4):837-847 (1998).

Yao et al., "Molecular views of viral polyprotein processing revealed by the crystal structure of the hepatitis C virus bifunctional protease-helicase," *Structure*, 7(11):1353-1363 (1999).

Younossi et al., "The roles of amantadine, rimantadine, ursodeoxycholic acid, and NSAIDs, alone or in combination with alpha interferons, in the treatment of chronic hepatitis C," *Seminars in Liver Disease*, 19(Suppl 1):95-102 (1999).

Yun et al., "Oxidation of the antihistaminic drug terfenadine in human liver microsomes. Role of cytochrome P-450 3A(4) in N-dealkylation and C-hydroxylation," *Drug Metabolism and Disposition*, 21(3):403-409 (1993).

Simon et al., "Treatment of chronic hepatitis C with interferon alfa-n3: a multicenter, randomized, open-label trial," *Hepatology*, 25(2):445-448 (1997).

Steinkuhler et al., "Hepatitis C virus protease inhibitors: current progress and future challenges," *Current Medicinal Chemistry*, 8(8):919-932 (2001).

Strader et al., "Diagnosis, management, and treatment of hepatitis C," *Hepatology*, 39(4):1147-1171 (2004).

Takamizawa et al., "Structure and organization of the hepatitis C virus genome isolated from human carriers," *Journal of Virology*, 65(3):1105-1113 (1991) .

Taliani et al., "A continuous assay of hepatitis C virus protease based on resonance energy transfer depsipeptide substrates," *Analytical Biochemistry*, 240(1):60-67 (1996).

Tanji et al., "Hepatitis C virus-encoded nonstructural protein NS4A has versatile functions in viral protein processing," *Journal of Virology*, 69(3):1575-1581 (1995).

Tazulakhova et al., "Russian experience in screening, analysis, and clinical application of novel interferon inducers," *Journal of Interferon and Cytokine Research*, 21(2):65-73 (2001).

Tomei et al., "NS3 is a serine protease required for processing of hepatitis C virus polyprotein," *Journal of Virology*, 67(7):4017-4026 (1993).

Trozzi et al., "In vitro selection and characterization of hepatitis C virus serine protease variants resistant to an active-site peptide inhibitor," *Journal of Virology*, 77(6):3669-3679 (2003).

Tsantrizos et al., "Macrocyclic inhibitors of the NS3 protease as potential therapeutic agents of hepatitis C virus infection," *Angewandte Chemie Int. Ed. Engl.*, 42(12):1356-1360 (2003).

Vorgruggen, "Some recent trends and progress in nucleoside synthesis," *Acta Biochimica Polonica*, 43(1):25-36 (1996).

Wasley et al., "Epidemiology of hepatitis C: geographic differences and temporal trends," *Seminars in Liver Disease*, 20(1):1-16 (2000).

Watanabe, "The Chemistry of C-Nucleotides", *Chemistry of Nucleosides and Nucleotides*, 3(Chapter 5):421-535 (1994).

* cited by examiner

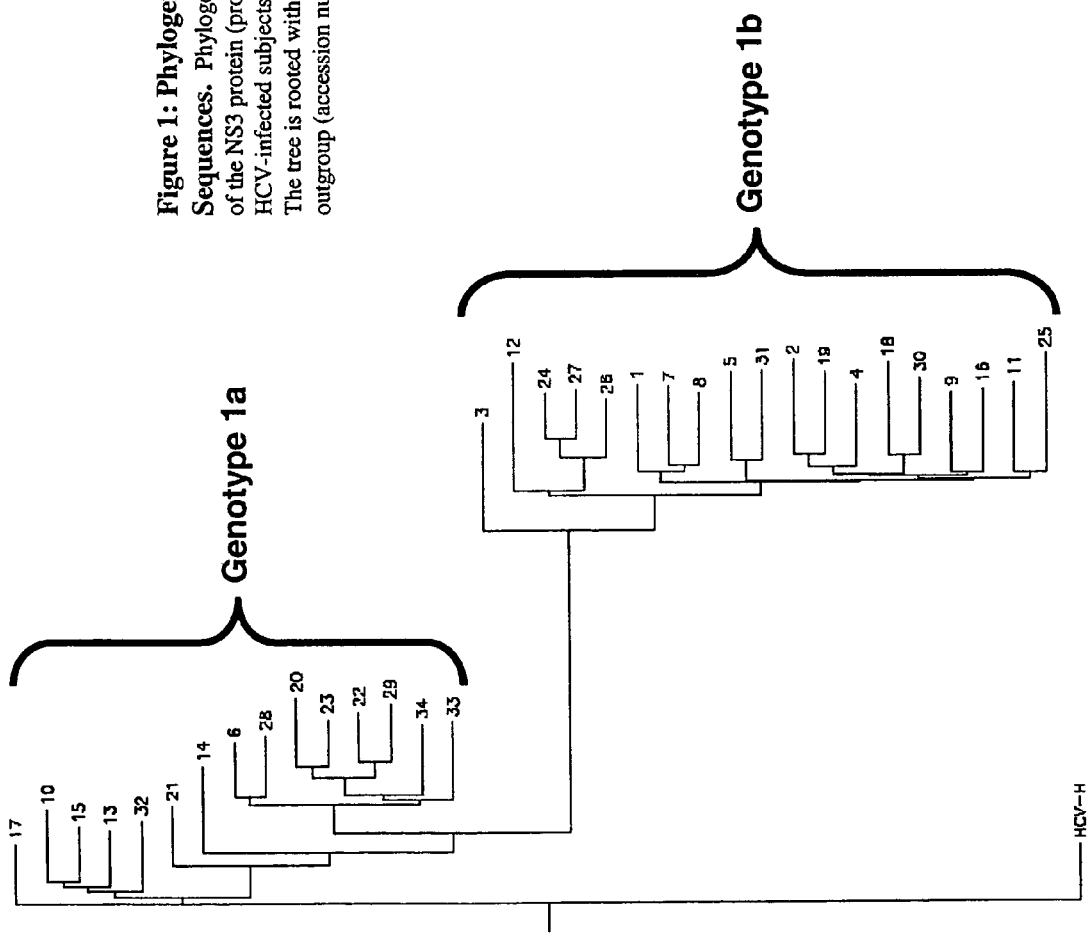
Figure 1: Phylogenetic Analysis of Baseline Sequences. Phylogenetic tree of the N-terminal 543 nucleotides of the NS3 protein (protease domain) from untreated genotype 1 HCV-infected subjects. Sequences cluster into subtypes 1a and 1b. The tree is rooted with the reference lab strain HCV-H as an outgroup (accession number M67463).

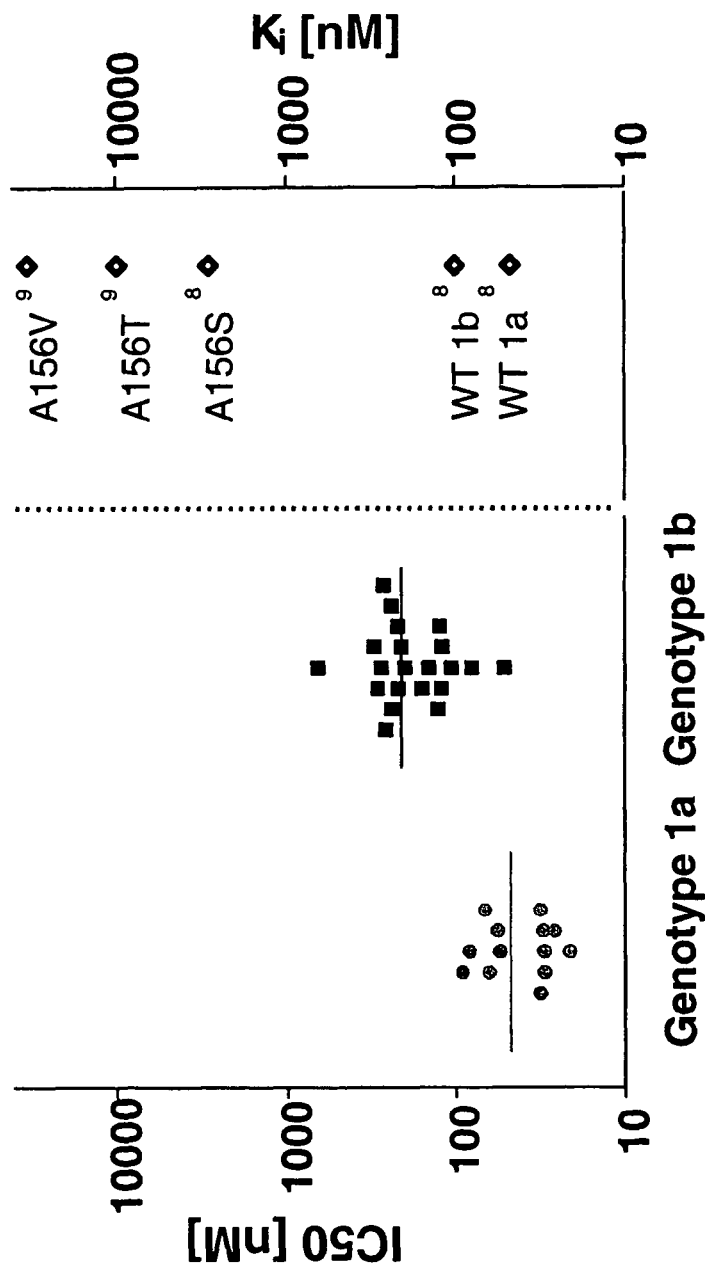

Figure 2: Baseline IC$_{50}$s for Genotype 1a and 1b. Protease variants from untreated subjects were expressed, purified, and tested for sensitivity to VX-950. The enzyme IC$_{50}$ of VX-950 against each protease is shown (values are the mean of 2 independent experiments). Results are grouped by genotype 1a and genotype 1b. The line indicates the mean of all data points. Included for comparison are K$_i$ values of previously published wild-type proteases and protease mutants known to confer resistance to VX-950 (A156V/T/S).

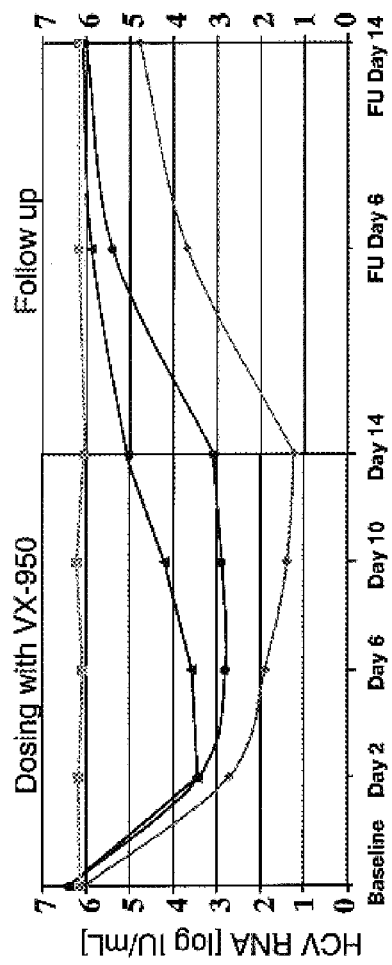
Figure 3: Subject Groups by Viral Response. Subject groups are divided by HCV RNA response to 14 days of dosing with VX-950 based on mutational patterns. HCV RNA values shown are the mean values for each group of subjects.

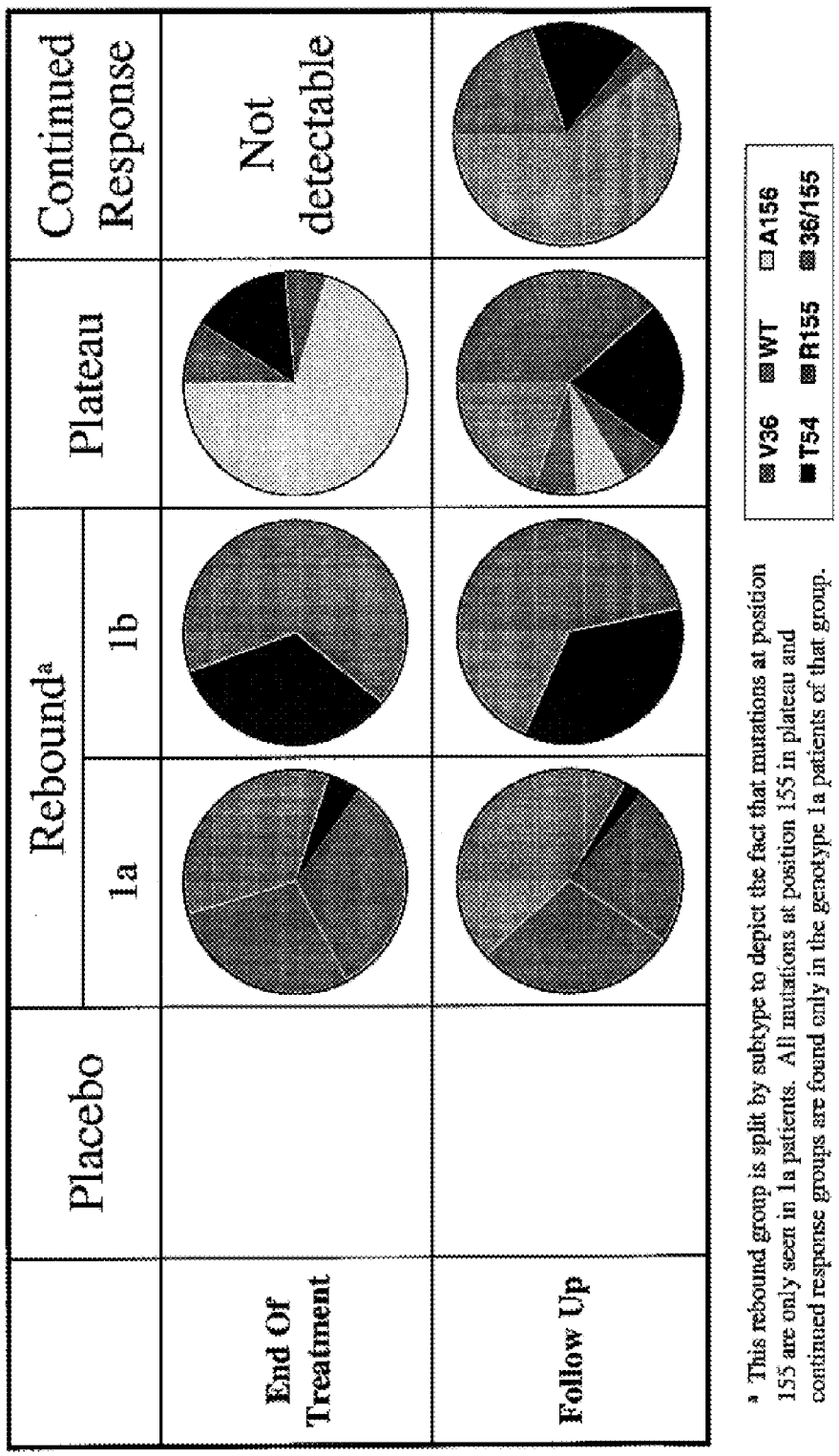

Figure 4: Summary of Viral Response and Mutation Patterns. Pie charts show the average percent of mutations at a given amino acid position for all subjects within a given response group.

[a] This rebound group is split by subtype to depict the fact that mutations at position 155 are only seen in 1a patients. All mutations at position 155 in plateau and continued response groups are found only in the genotype 1a patients of that group.

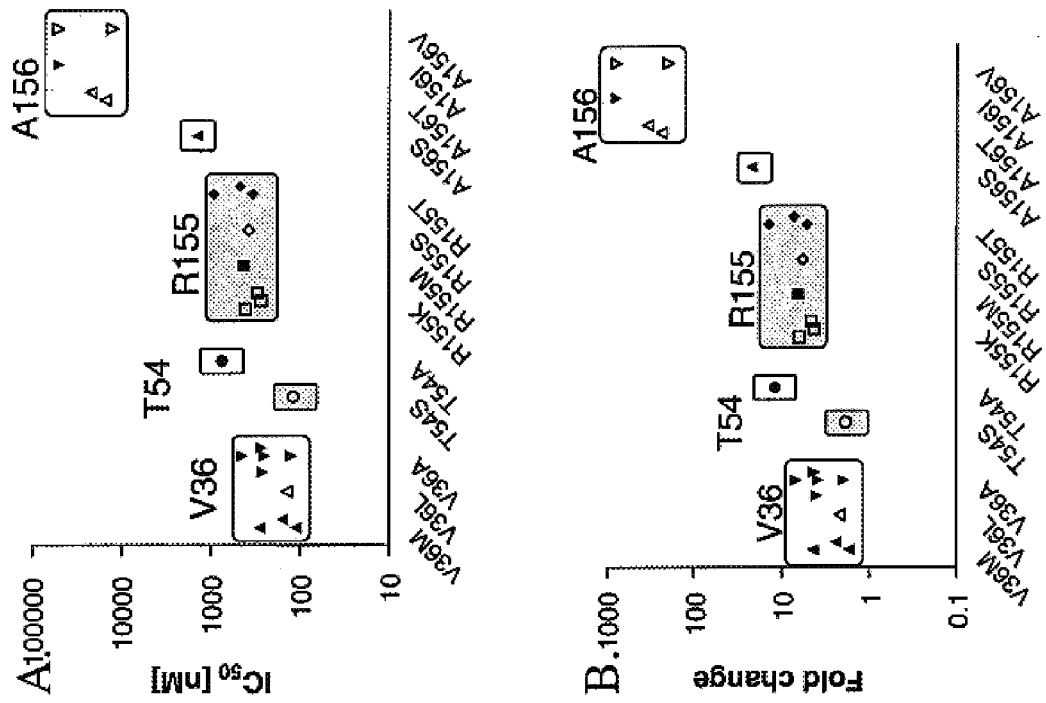

Figure 5: Enzymatic IC50 and Fold Change from Reference 1a Strain HCV-H of Protease Single Resistance Mutants to VX-950. Protease mutants selected in subjects dosed with VX-950 were expressed, purified and tested for sensitivity to VX-950. Values are the mean of 2 independent experiments for a given protease mutant sequence. The IC50 of VX-950 against each protease is shown (A) and compared to the reference strain HCV-H (B).

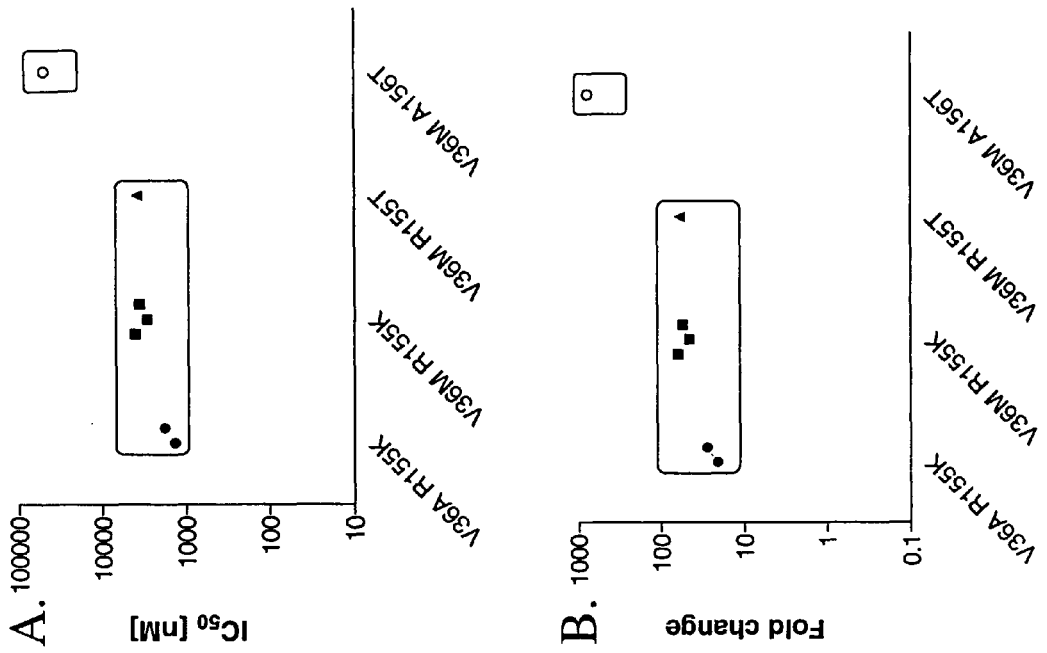

Figure 6: Enzymatic IC50 and Fold Change from Reference 1a Strain HCV-H of Protease Double Resistant Mutants to VX-950. Protease mutants selected in subjects dosed with VX-950 were expressed, purified and tested for sensitivity to VX-950. Values are the mean of 2 independent experiments for a given protease mutant sequence. The IC50 of VX-950 against each protease is shown (A) and compared to the reference strain HCV-H (B).

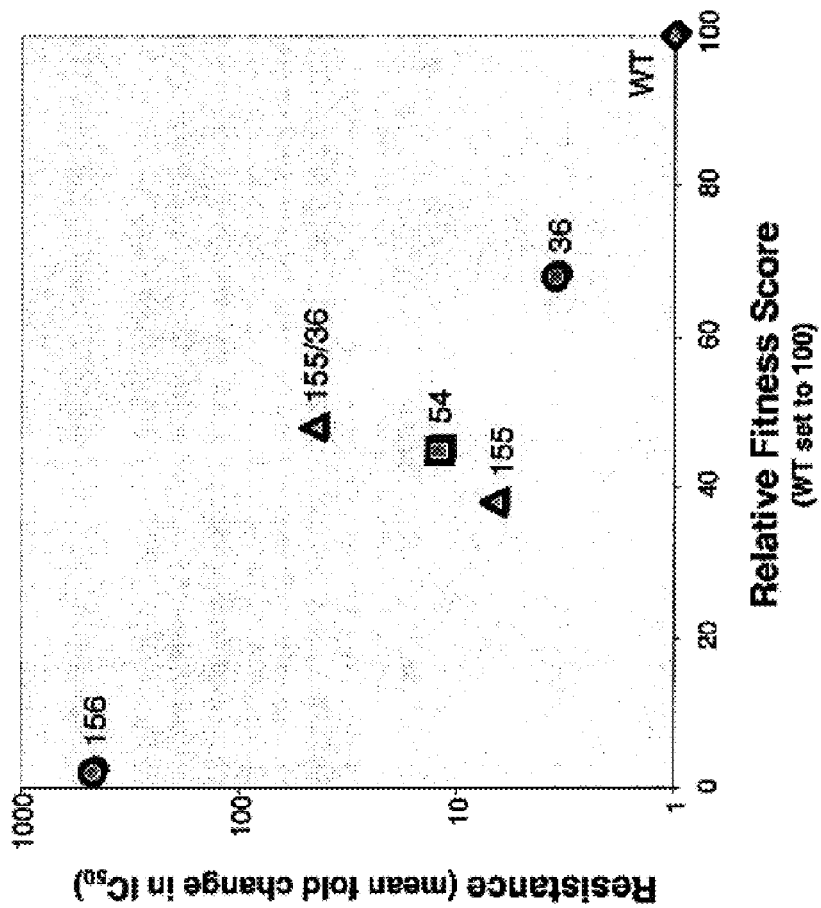
Figure 7: Inverse Correlation Between Resistance and Fitness

Location of Telaprevir-resistant Mutations in the HCV Protease

V36 Does not Make Direct Contact with Telaprevir (VX-950)

- V36 does not make direct contact with telaprevir (VX-950)
- V36 is located next to the NS4A cofactor ß-strand
- V36 (and T54) make hydrophobic contacts with F43
- F43, in turn, interacts with the P1' group of telaprevir (VX-950)

V36M Variant in G1a: Low-level Resistance, More Fi

- Phenotype
  - 6-7 fold resistance to telaprevir

V36G Variant in G1b: Low-level Resistance, Less Fit

- Phenotype
  - Similar resistance as V36M/A
  - Average % of HCV RNA at day 14 in patients dosed with telaprevir alone
    - 0% in G1a (1-nt change)
    - 14% in G1b (1-nt change)
  - Less fit than V36M
- Mechanism
  - Loss of hydrophobic interaction with F43 ➠ increased flexibility of F43 and P1' pocket
  - Loss of interaction between F43 and telaprevir P1' group
  - Does NOT gain additional interaction with protease

VERTE

Figure 16

V36L Variant: No Resistance, Rare in G1 (Polymorphism)

- Phenotype
  - No resistance
  - Average % of HCV RNA at day 14 in patients dosed with telaprevir alone
    - 0.7% in G1a (polymorphism)
    - 0% in G1b
  - L36 exists in G2, G3, or G4 HCV NS3 protease
- Mechanism
  - Little loss of hydrophobic interaction with F43
  - Little loss of interaction between F43 and telaprevir P1' group

HCV Sequence Diversity and Resistance Mutations

- Sequence changes (mutations) in the HCV genome occur spontaneously and frequently as a natural result of viral replication
  - HCV polymerase has a high error rate (~1 error per genome)
  - High rate of HCV replication (~$10^{12}$ virions produced per day)

- Therefore, variants with mutations conferring resistance to a specifically-targeted antiviral most likely exist at a low frequency prior to drug treatment

- Strong inhibition of wild-type virus with a specifically-targeted antiviral drug selects for drug-resistant virus

- NS3 protease mutations observed in Ph 1b trial of telaprevir alone
  - V36M/A/G
  - T54A
  - R155K/T/M/S/I/G
  - A156S/V/T (observed previously in replicon-based in vitro studies)
  - V36M/A+R155K/T

VERTEX

Figure 30

Mechanisms of Resistance to HCV Protease Inhibitors

- In the active site
  - A156S/V/T (Lin 2004, Lu 2004, & Lin 2005)
    - Steric hindrance (direct) to inhibitor binding
  - D168A/V (Trozzi 2003, Lin 2004 & Lu 2004)
    - Steric hindrance (indirect) to inhibitor binding
  - R155K/T/S/I/M/G (Lin AASLD 2006)
    - Loss of contact (direct) to inhibitor
- Outside the active site
  - V36M/A/G ??
  - T54A

Figure 31

Conclusions

- Mechanism of resistance to HCV protease inhibitors
  - A156S/V/T: Steric hindrance (direct) to telaprevir binding
  - D168A/V: Steric hindrance (indirect) to BILN 2061 binding
  - R155K/T: Loss of contact (direct) to telaprevir
  - V36M/A/G: Loss of contact (indirect) to telaprevir
    - V36M: Low-level resistance, more fit than V36A/G
    - V36A/G: Low-level resistance, less fit than V36M
    - V36L: No resistance (polymorphism)

VERTE

Figure 32

Summary

- Telaprevir-resistant variants can be classified into two groups:
  - Low-level resistance (<25-fold): V36, T54, R155, A156S
  - High-level resistance (>50-fold): A156V/T or V36+R155

- Mechanism of resistance to telaprevir:
  - Loss of interaction to the P1' group (V36)
  - Loss of interaction to the P2 group (R155)

- Telaprevir-resistant variants remain sensitive to IFN-alpha and ribavirin in replicon cells
- No subjects had viral breakthrough during dosing of telaprevir in combination with PEG-IFN +/- ribavirin

VERTEX

Figure 33

HEPATITIS C VIRUS VARIANTS

RELATED APPLICATIONS

This application claims the benefit of and priority to U.S. provisional application No. 60/735,577, filed Nov. 11, 2005 and U.S. provisional application No. 60/854,598, filed Oct. 25, 2006. The contents of these provisional applications are incorporated herein by reference.

FIELD OF THE INVENTION

The present invention relates to hepatitis C virus (HCV) variants.

BACKGROUND OF THE INVENTION

Hepatitis C virus (HCV) infects more than 170 million people worldwide and is the leading cause of chronic hepatitis, which can ultimately lead to end-stage liver cirrhosis and hepatocellular carcinoma. The standard treatment for HCV infection is currently pegylated interferon alpha (Peg-IFN) in combination with ribavirin (RBV). The goal of HCV therapy is to eliminate viral infection by obtaining a sustained viral response (SVR) as defined by having undetectable HCV-RNA in the blood after 6 months of antiviral treatment. Unfortunately, the current treatment is not effective in about 50% of subjects with genotype 1, and the side effects are significant. Thus, new antiviral targets and improved treatment strategies are needed (Pawlotsky, J. M., and J. G. McHutchison, 2004, Hepatitis C. Development of new drugs and clinical trials: promises and pitfalls. Summary of an AASLD hepatitis single topic conference, Chicago, Ill., Feb. 27-Mar. 1, 2003, Hepatology 39:554-67; Strader, et al., 2004, Diagnosis, management, and treatment of hepatitis C. Hepatology 39:1147-71).

The non-structural (NS) 3-4A protease is essential for HCV replication and a promising target for new anti-HCV therapy. VX-950, a potent and specific NS3-4A protease inhibitor demonstrated substantial antiviral activity in a phase 1b trial of subjects infected with HCV genotype 1 (Study VX04-950-101). The degree to which a subject responds to treatment and the rate at which viral rebound is observed could in part be due to genotypic differences in sensitivity to the protease inhibitor. The rapid replication rate of HCV, along with the poor fidelity of its polymerase, gives rise to an accumulation of mutations throughout its genome (Simmonds, P., 2004, Genetic diversity and evolution of hepatitis C virus—15 years on. J. Gen. Virol. 85:3173-88). The degree to which sequence variability in the protease region affects the catalytic efficiency of the enzyme or the binding of an inhibitor is not known. Additionally, the generation of numerous viral genomes with remarkable sequence variation presents potential problems of emerging drug resistant virus in subjects treated with antiviral therapy. Indeed, drug resistance against antiviral drugs, such as HIV protease inhibitors, is well documented (Johnson, et al., 2004, Top. HIV Med. 12:119-24). Drug resistant mutations have already been shown to develop in vitro in the presence of HCV protease inhibitors (Lin, et al., 2005, In vitro studies of cross-resistance mutations against two hepatitis C virus serine protease inhibitors, VX-950 and BILN 2061. J. Biol. Chem. 280: 36784-36791; Lin, et al., 2004, In vitro resistance studies of hepatitis C virus serine protease inhibitors, VX-950 and BILN 2061: Structural analysis indicates different resistance mechanisms. J. Biol. Chem. 279:17508-17514; Lu, et al., 2004, Antimicrob. Agents Chemother. 48:2260-6; Trozzi, et al., 2003, In vitro selection and characterization of hepatitis C virus serine protease variants resistant to an active-site peptide inhibitor. J. Virol. 77:3669-79). Mutations resistant to the protease inhibitor BILN 2061 have been found at positions R155Q, A156T, and D168V/A/Y in the NS3 gene, but no mutations have yet been observed in the NS4 region or in the protease cleavage sites. A VX-950 resistance mutation has also been found in vitro at position A156S. Cross-resistant mutations against both VX-950 and BILN 2061 have also been shown to develop in vitro at position 156 (A156V/T (Lin, et al., 2005, supra).

Accordingly, there exists a need in identifying mutated HCVs or other viruses that exhibit resistance to drugs or other therapies and in developing new viral therapeutics effective against these mutated viruses.

SUMMARY OF THE INVENTION

Accordingly, the present invention provides HCV variants, and related methods and compositions. In particular, HCV variants and variant HCV proteases that have reduced sensitivity to one or more protease inhibitors such as VX-950 are provided.

In one aspect, this invention provides an isolated HCV polynucleotide encoding an HCV NS3 protease, a biologically active analog thereof, or a biologically active fragment thereof. The isolated HCV polynucleotide has at least one codon that corresponds to codon 36, 41, 43, 54, 148, 155, or 156 of a wild-type HCV polynucleotide that is mutated such that it encodes an amino acid different from the amino acid encoded by the corresponding codon of the wild-type HCV polynucleotide. The wild-type HCV polynucleotide may comprise a nucleotide sequence of SEQ ID NO:1 or a portion thereof such as for example the first 543 nucleotides of SEQ ID NO:1. Alternatively, the wild-type HCV polynucleotide may comprise a nucleotide sequence that is at least 60%, 75%, 80%, 85%, 90%, 95%, 97%, 98%, 99%, or higher, identical to the sequence of SEQ ID NO:1 or a portion thereof.

In certain embodiments, the isolated HCV polynucleotide comprises a codon corresponding to codon 36 of the wild-type HCV polynucleotide, and the codon does not encode V. In certain embodiments, the codon encodes M, L, A, or G.

In certain embodiments, the isolated HCV polynucleotide comprises a codon corresponding to codon 41 of the wild-type HCV polynucleotide, and the codon does not encode Q. In certain embodiments, the codon encodes H.

In certain embodiments, the isolated HCV polynucleotide comprises a codon corresponding to codon 43 of the wild-type HCV polynucleotide, and the codon does not encode F. In certain embodiments, the codon encodes S.

In certain embodiments, the isolated HCV polynucleotide comprises a codon corresponding to codon 54 of the wild-type HCV polynucleotide, and the codon does not encode T. In certain embodiments, the codon encodes S or A.

In certain embodiments, the isolated HCV polynucleotide comprises a codon corresponding to codon 148 of the wild-type HCV polynucleotide, and the codon does not encode G. In certain embodiments, the codon encodes E.

In certain embodiments, the isolated HCV polynucleotide comprises a codon corresponding to codon 155 of the wild-type HCV polynucleotide, and the codon does not encode R. In certain embodiments, the codon encodes K, M, S, T, G, I, or L.

In certain embodiments, the isolated HCV polynucleotide comprises a codon corresponding to codon 156 of the wild-type HCV polynucleotide, and the codon does not encode A. In certain embodiments, the codon encodes S, T, V, or I.

In certain embodiments, the isolated HCV polynucleotide comprises two codons that correspond to any two codons selected from the group consisting of: codons 36, 41, 43, 54, 148, 155, and 156 of a wild-type HCV polynucleotide, and the two codons are mutated such that either codon encodes an amino acid different from the amino acid encoded by the corresponding codon of the wild-type HCV polynucleotide. For example, the isolated HCV polynucleotide comprises a codon corresponding to codon 36 of the wild-type HCV polynucleotide, and the codon encodes A or M; the isolated HCV polynucleotide further comprises a codon corresponding to codon 155 of the wild-type polynucleotide, and the codon encodes K or T; alternatively, the isolated HCV polynucleotide further comprises a codon corresponding to codon 156 of the wild-type polynucleotide, and the codon encodes T.

In certain embodiments, the isolated HCV polynucleotide comprises three codons that correspond to any three codons selected from the group consisting of: codons 36, 41, 43, 54, 148, 155, and 156 of a wild-type HCV polynucleotide, and the three codons are mutated such that each of the three codons encodes an amino acid different from the amino acid encoded by the corresponding codon of the wild-type HCV polynucleotide.

In certain embodiments, the isolated HCV polynucleotide comprises four codons corresponding to codons 36, 41, 43, 54, 148, 155, and 156 of a wild-type HCV polynucleotide; and the four codons are mutated such that each of the four codons encodes an amino acid different from the amino acid encoded by the corresponding codon of the wild-type HCV polynucleotide.

In further embodiments, this invention provides methods and compositions involving an HCV polynucleotide of the invention. For example, an expression system comprising the HCV polynucleotide is provided, and such expression system may include a vector that comprises the HCV polynucleotide operably linked to a promoter; also provided is a host cell transfected, transformed, or transduced with the vector. Alternatively, an expression system of the invention is based on an mRNA display technology, e.g., the RNA-protein fusion technology as described in U.S. Pat. No. 6,258,558 or the in vitro "virus" technology as described in U.S. Pat. No. 6,361,943.

In another aspect, this invention provides isolated HCV variants. An isolated HCV variant may comprise a polynucleotide encoding an HCV NS3 protease, wherein at least one codon of the polynucleotide that corresponds to a codon selected from the group consisting of: codons 36, 41, 43, 54, 148, 155, and 156 of a wild-type HCV polynucleotide is mutated such that it encodes an amino acid different from the amino acid encoded by the corresponding codon of the wild-type HCV polynucleotide. Further embodiments of the invention provide methods and compositions involving the HCV variants. For example, a method is provided to identify a compound that can inhibit replication of an HCV variant of the invention; a cell is provided that is infected by an HCV variant of the invention.

In another aspect, this invention provides isolated HCV proteases, particularly HCV NS3 proteases. An isolated HCV NS3 protease may comprise an amino acid sequence in which the amino acid at at least one position selected from the group consisting of: 36, 41, 43, 54, 148, 155, and 156 of a wild-type HCV NS3 protease is different from the amino acid at each corresponding position of the wild-type HCV NS3 protease. The wild type HCV NS3 protease may comprise an amino acid sequence of SEQ ID NO:2 or a portion thereof such as for example the first 181 amino acids of SEQ ID NO:2. The isolated HCV NS3 protease may comprise a biologically active analog or fragment of an HCV NS3 protease, for example, the isolated HCV NS3 protease may not have the N-terminal 5, 10, 15, 20, 30, 35, 40, 45, or 48 amino acids of SEQ ID NO:2.

An isolated HCV NS3 protease may also include an NS4A cofactor, such as for example an NS4A protein as represented by the last 54 amino acids of SEQ ID NO:2. An isolated HCV NS3 protease may be a protein complex formed by tethering an NS4A cofactor to an NS3 protease domain, for example as described in U.S. Pat. Nos. 6,653,127 and 6,211,338.

In a further aspect, this invention provides an antibody specific to an HCV protease of the invention. The antibody may recognize an HCV NS3 protease comprising an amino acid sequence in which the amino acid at at least one position selected from the group consisting of: 36, 41, 43, 54, 148, 155, and 156 of a wild-type HCV NS3 protease is different from the amino acid at each corresponding position of the wild-type HCV NS3 protease. Further embodiments of the invention provide methods and compositions involving an anti-HCV protease antibody of the invention. For example, a diagnostic kit comprising an antibody of the invention, and a pharmaceutical compositions comprising an antibody of the invention and a pharmaceutically acceptable carrier are provided.

In another aspect, this invention provides a nucleotide probe or primer capable of hybridizing under stringent conditions to a nucleic acid sequence of an HCV polynucleotide of the invention. Further embodiments of the invention provide methods and compositions involving the probe or primer. For example, a diagnostic or detection kit comprising a probe or primer of the invention is provided, and the kit is useful in, e.g., determining whether an HCV variant or an HCV NS3 protease of the invention is present in a sample.

In a further aspect, this invention provides methods for evaluating drug resistance or sensitivity to a protease inhibitor of an HCV infection in a patient. Such a method may comprise collecting a biological sample from the HCV infected patient and evaluating or determining whether the sample comprises a nucleic acid encoding an HCV NS3 protease that comprises an amino acid sequence in which the amino acid at at least one position selected from the group consisting of: 36, 41, 43, 54, 148, 155, and 156 of a wild-type HCV NS3 protease is different from the amino acid at each corresponding position of the wild-type HCV NS3 protease. The protease inhibitor may be VX-950 or another protease inhibitor.

Also provided is a method for guiding a treatment or designing a therapeutic regimen for an HCV infection in a patient. The method may comprise evaluating drug resistance or sensitivity to a protease inhibitor of the patient and determining the regimen for the patient based on the drug resistance or sensitivity. For example, if drug resistance is predicted or detected (e.g., reduced sensitivity to a protease inhibitor such as VX-950), one or more other compounds or agents may be included in the patient's treatment plan or therapeutic regimen. The method may comprise any combination of determining the sequence (e.g., genotyping) of an HCV NS3 protease in the patient, determining the sensitivity to a protease inhibitor of an HCV NS3 protease in the patient (e.g., phenotyping), or determining the viral fitness level of the patient's HCVs. The phenotyping may be carried out in a cell-free system (e.g., in vitro protease assays) as well as a cell-based system (e.g., replicon assays or viral infection or replication assays).

In another aspect, this invention provides methods for identifying a candidate compound for treating an HCV infection in a patient. Such a method may comprise providing a sample infected with an HCV variant of the invention and assaying the ability of the candidate compound in inhibiting an activity of the HCV variant in the sample. The sample infected with an HCV variant may be obtained from a patient, such as cell or plasma samples. The sample infected with an HCV variant may also be cultured cells. The activity of the HCV variant may be determined by its ability to infect, replicate, and/or become released.

Alternatively, such a method may comprise providing a replicon RNA comprising an HCV polynucleotide of the invention and determining whether the candidate compound inhibits replication of the replicon RNA in a suitable assay.

Another alternative method may comprise providing an isolated HCV NS3 protease of invention and a protease substrate, and determining whether the HCV NS3 protease activity is reduced in the presence of a candidate compound; the HCV NS3 protease and/or the protease substrate may be in a cell-based system, for example expressed in cultured cells, or the HCV NS3 protease and/or the protease substrate may be in a cell-free system, for example a reaction mixture including an HCV NS3 protease and a peptide substrate. The HCV NS3 protease may be an RNA-protein fusion molecule as described in U.S. Pat. No. 6,258,558, and such a fusion molecules can be included in cell-free assays that evaluate protease activity.

A further alternative method for evaluating a candidate compound for treating an HCV infection in a patient may include introducing a vector comprising an HCV polynucleotide of the invention and an indicator gene encoding an indicator into a host cell and measuring the indicator in the presence of the candidate compound and in the absence of the candidate compound.

Another aspect of this invention provides a method for identifying a compound capable of rescuing the activity of VX-950 against an HCV NS3 protease, for example, an HCV NS3 protease that has become resistant to VX-950. Such a compound is also termed "a secondary compound." The method may comprise contacting an HCV NS3 protease of the invention with a candidate compound and assaying the ability of VX-950 to inhibit the activity of the HCV NS3 protease. The method may also comprise the steps of in silico modeling a variant HCV NS3 protease with reduced sensitivity to VX-950 (e.g., as determined by measuring $IC_{50}$ and/or $K_i$), and designing and/or selecting a compound that may rescue the activity of VX-950.

Also provided is a method for treating an HCV infection in a patient, and the method comprises administering to the patient a pharmaceutically effective amount of a secondary compound that can rescue the activity of VX-950. The secondary compound can be administered to the patient alone or in combination with VX-950. The secondary compound may replace VX-950 in the patient's therapeutic regimen temporarily or permanently. For example, in a temporary replacement therapeutic regimen, VX-950 is administered to the patient again after the compound is administered to the patient and has rescued the activity of VX-950.

Further provided is a method for identifying a compound effective in reducing an HCV NS3 protease activity. The method may comprise obtaining a three dimensional model of an HCV NS3 protease of the invention and designing or selecting a compound. The method may further comprise evaluating, in silico, in vitro, and/or in vivo, the ability of the compound to bind to or interact with the protease. The method may also involve determine whether the designed or selected compound can inhibit the activity of an HCV NS3 protease, in particular, a variant HCV NS3 protease with reduced sensitivity to a protease inhibitor such as VX-950, in a cell-free or cell-based assay. The method may further or alternatively include assaying the ability of a designed or selected compound to inhibit HCV replication in a cell or sample. The HCV replication can be determined by measuring the replication of an HCV variant of the invention or an HCV replicon of the invention.

Another aspect of this invention provides methods for eliminating or reducing HCV contamination of a biological sample, or a medical or laboratory equipment. The method may comprise the step of contacting the biological sample, or the medical or laboratory equipment with a compound of the invention, such as a compound identified by a method described herein.

A further aspect of this invention provides a method for treating an HCV infection in a patient. The method may comprise administering to the patient a pharmaceutically or therapeutically effective amount of a compound identified by a method of the invention alone or in combination with another anti-viral agent.

Another aspect of the invention relates to computer tools, which provides a machine-readable data storage medium comprising a data storage material encoded with machine-readable data, wherein the machine-readable data comprise index values for at least two features associated with an HCV variant or biological sample. The features are selected from: a) the ability to exhibit resistance for reduced sensitivity to a protease inhibitor; b) an HCV protease comprising an amino acid sequence in which the amino acid at at least one position selected from the group consisting of: 36, 41, 43, 54, 148, 155, and 156 of a wild-type HCV NS3 protease is different from the amino acid at each corresponding position of the wild-type HCV NS3 protease; c) morbidity or recovery potential of a patient; and d) altered replication capacity (increased or decreased) of the HCV variant.

A further aspect of the invention provides a method of obtaining a profile of HCV variants in an HCV-infected patient. The method may comprise obtaining a sample (e.g., a plasma sample) from the patient and genotyping and/or phenotyping an HCV protease from at least 2, 20, 50, 100, 200, 500 or more HCV virions from the sample. For example, such genotyping may include determining the nucleotide sequence of an HCV protease from at least 2, 20, 50, 100, 200, 500 or more HCV virions from the plasma sample.

In certain embodiments, the patient subjected to such profiling may have been treated or be selected to be treated with a protease inhibitor such as VX-950. In certain embodiments, plasma samples are obtained from the patient subjected to such profiling at two or more different time points.

BRIEF DESCRIPTION OF THE DRAWINGS

FIG. 1 illustrates a phylogenetic analysis of baseline sequences of the N terminal 543 nucleotides of the NS3 protein from untreated genotype 1 HCV-infected subjects.

FIG. 2 shows the baseline $IC_{50}$s of Telaprevir (VX-950) for genotype 1a and 1b protease variants.

FIG. 3 illustrates the grouping of subjects based on viral response to VX-950.

FIG. 4 (in color) summarizes viral responses corresponding to mutation patterns.

FIG. 5 shows enzymatic $IC_{50}$s and fold change from the reference genotype 1a strain of HCV-H of protease single resistance mutants to VX-950.

FIG. 6 shows enzymatic $IC_{50}$s and fold change from the reference genotype 1a strain of HCV-H of protease double resistance mutants to VX-950.

FIG. 7 shows the inverse correlation between resistance to VX-950 and fitness.

Figure 19:
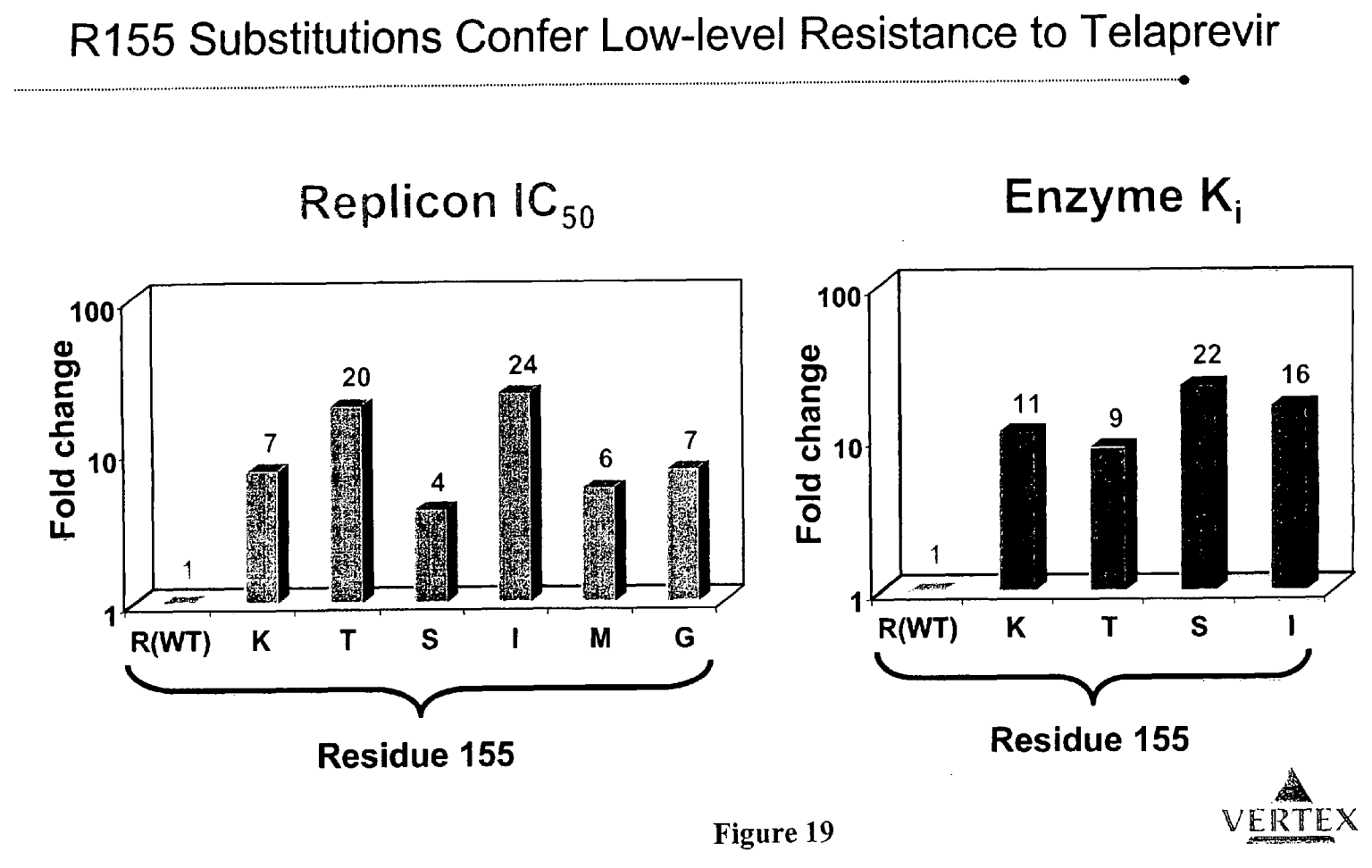

FIG. 19 shows that R155 substitutions confer low-level resistance to VX-950.

Figure 28:
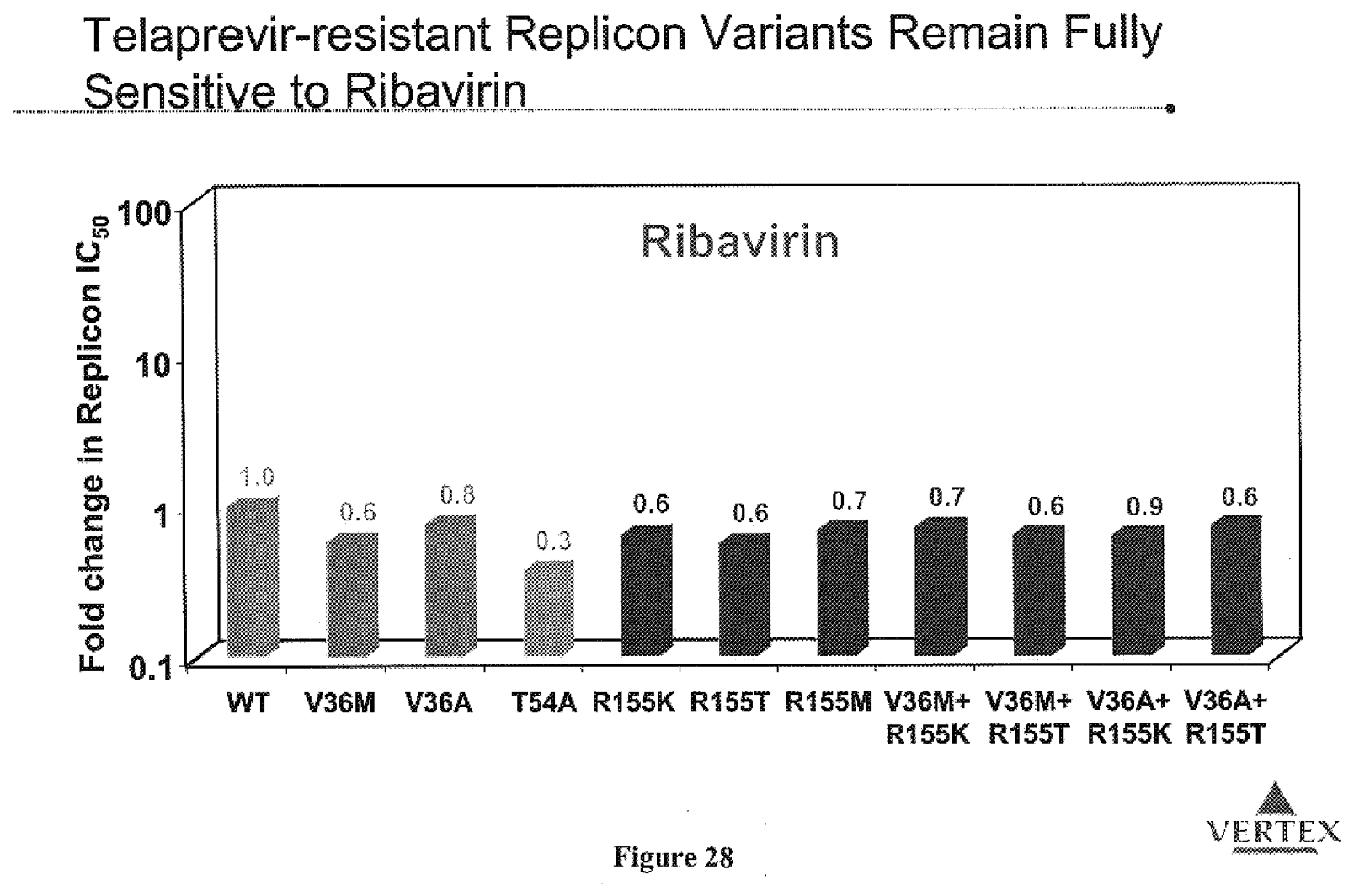

FIG. 28 shows that the VX-950 resistant replicon variants remain fully sensitive to Ribavirin.

FIG. 30 provides summary points regarding HCV sequence diversity and resistance mutations.

FIG. 31 summarizes the mechanisms of viral variants resistance to HCV protease inhibitors including previous studies.

FIG. 32 outlines conclusions regarding the mechanisms of viral variants resistance to HCV protease inhibitors including previous and present studies.

FIG. 33 summarizes certain conclusions based on the present studies.

DETAILED DESCRIPTION OF THE INVENTION

Figure 8:
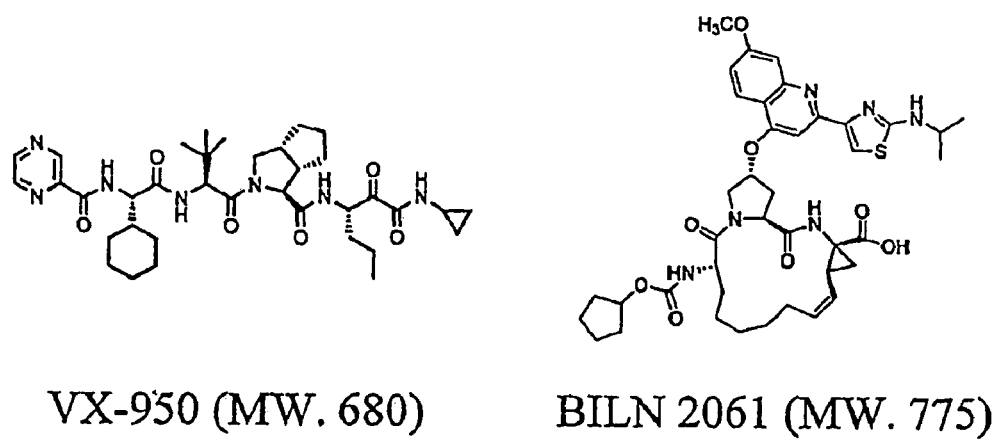
FIG. 8 illustrates the structure of two HCV protease inhibitors: VX-950 and BILN 2061.
Figure 9:
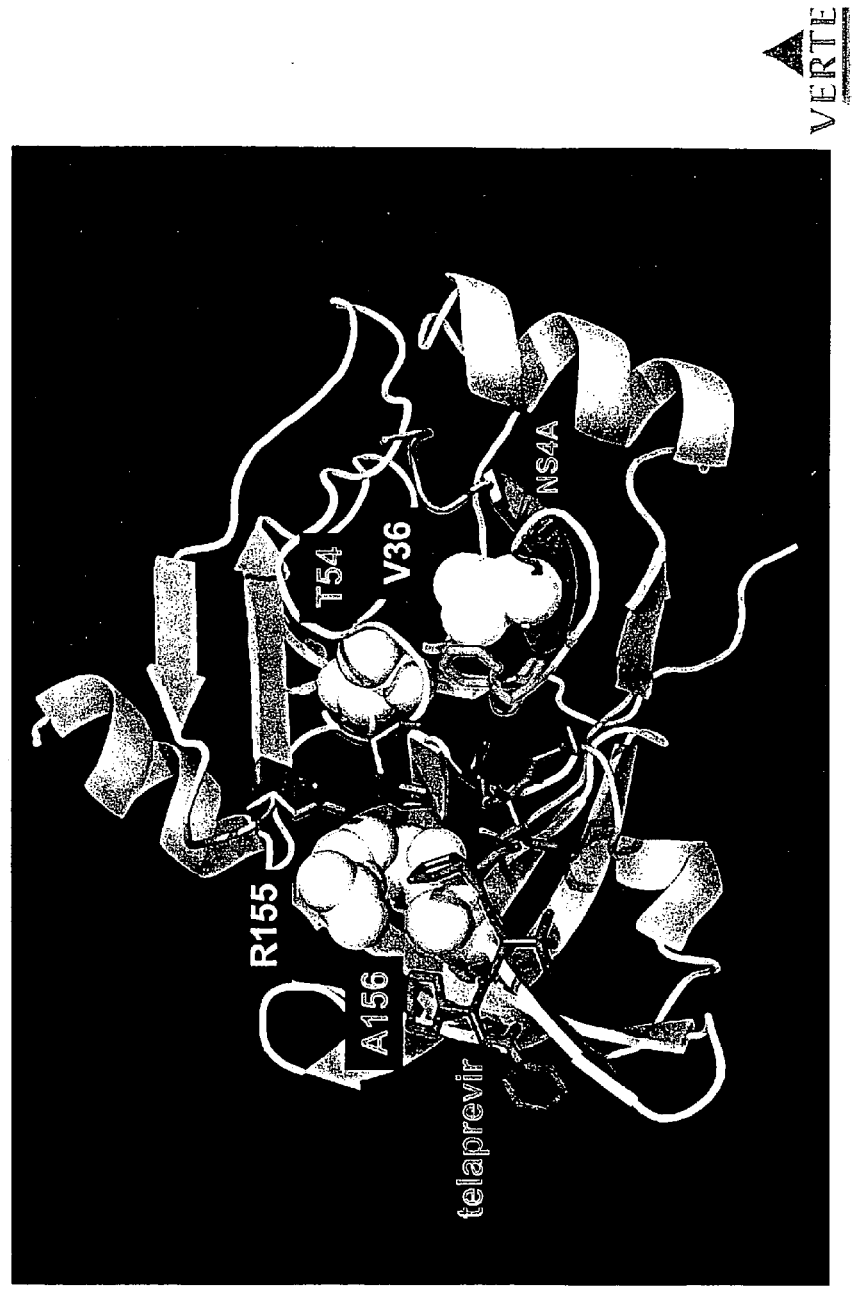
FIG. 9 illustrates the location of VX-950 variations in the HCV protease according to structural studies.
Figure 10:
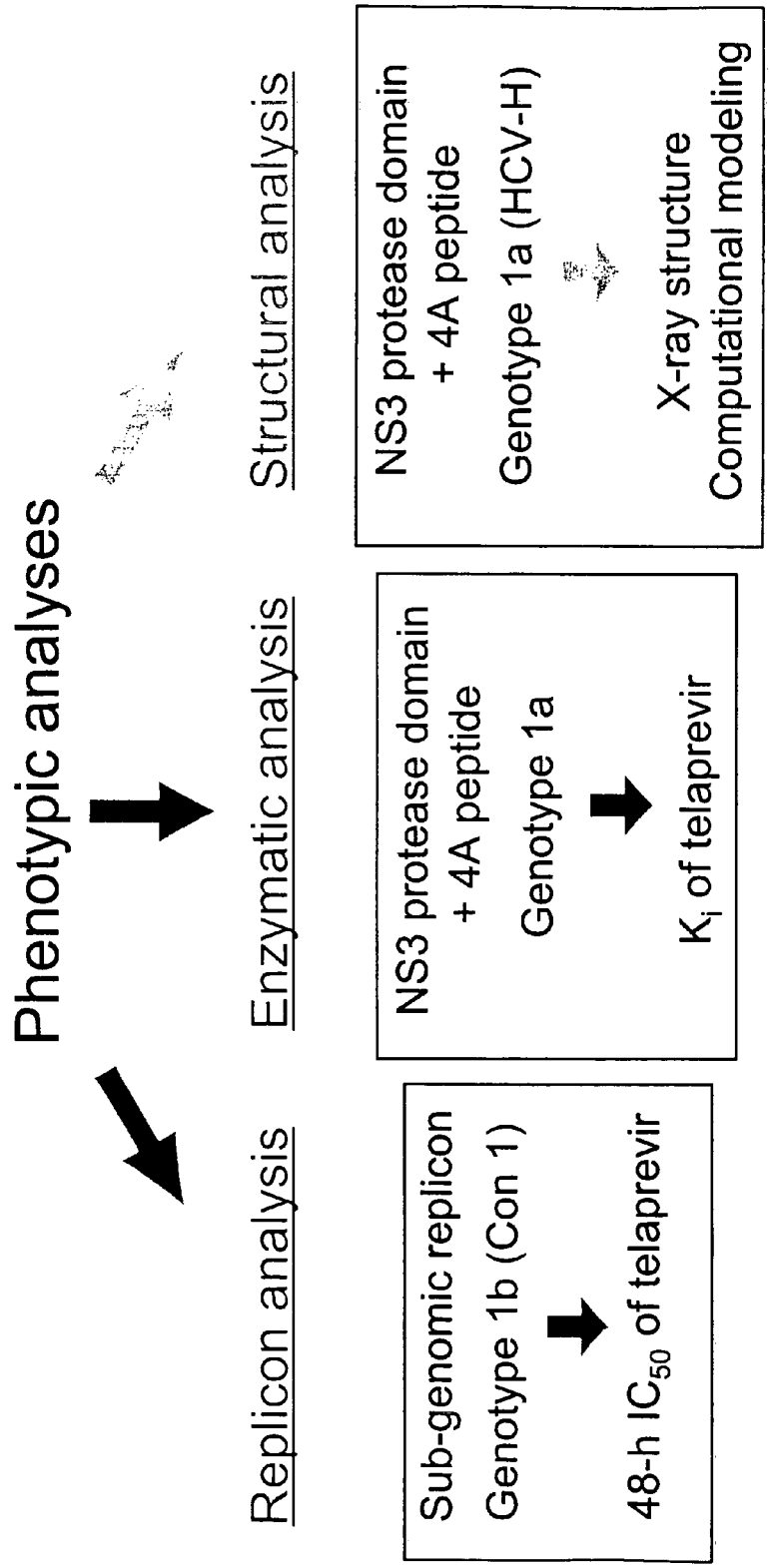
FIG. 10 outlines the methods for phenotypic analysis of HCV viral variants.
Figure 11:
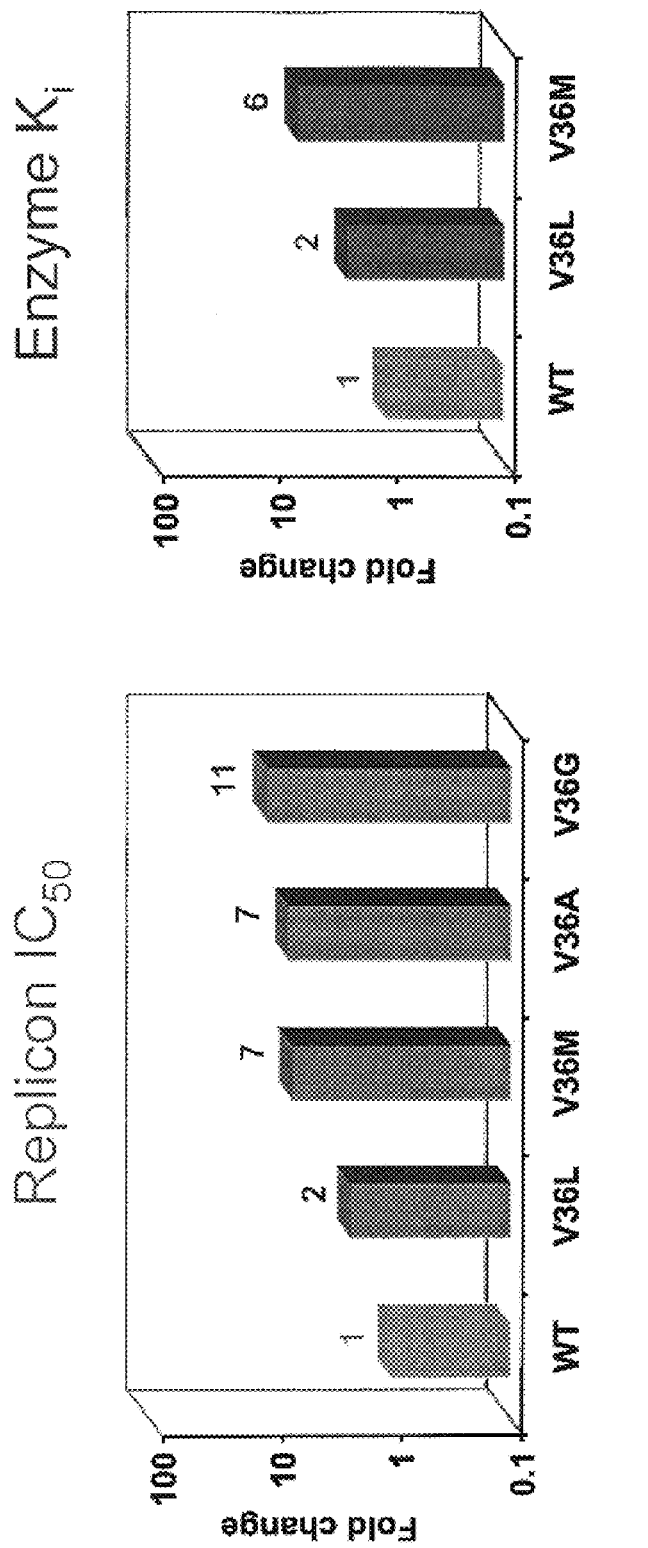
FIG. 11 shows that V36 substitutions confer low-level resistance to VX-950.
Figure 12:
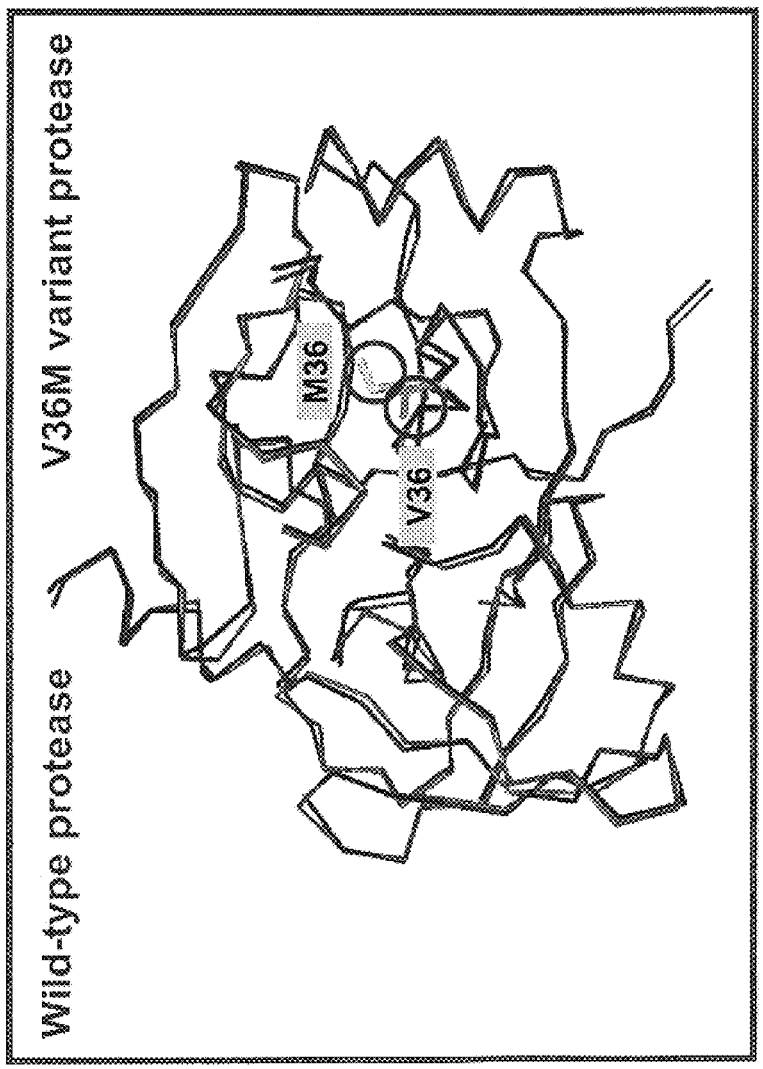
FIG. 12 shows X-ray structure of the V36M variant protease.
Figure 13:
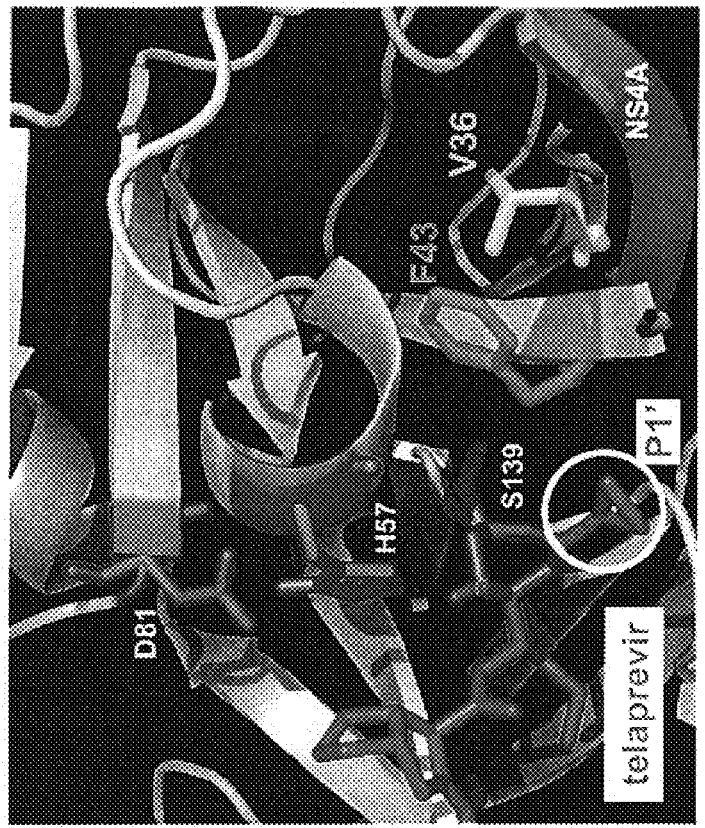
FIG. 13 shows that V36 does not make direct contact with VX-950.
Figure 14:
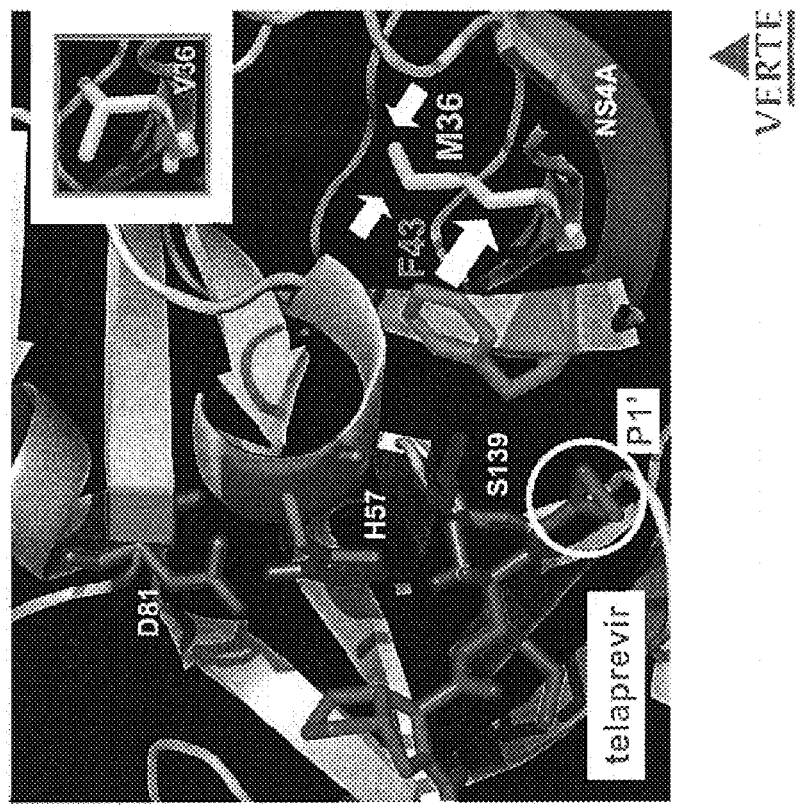
FIG. 14 shows the V36M variant in G1a with low-level resistance and better fitness.
Figure 15:
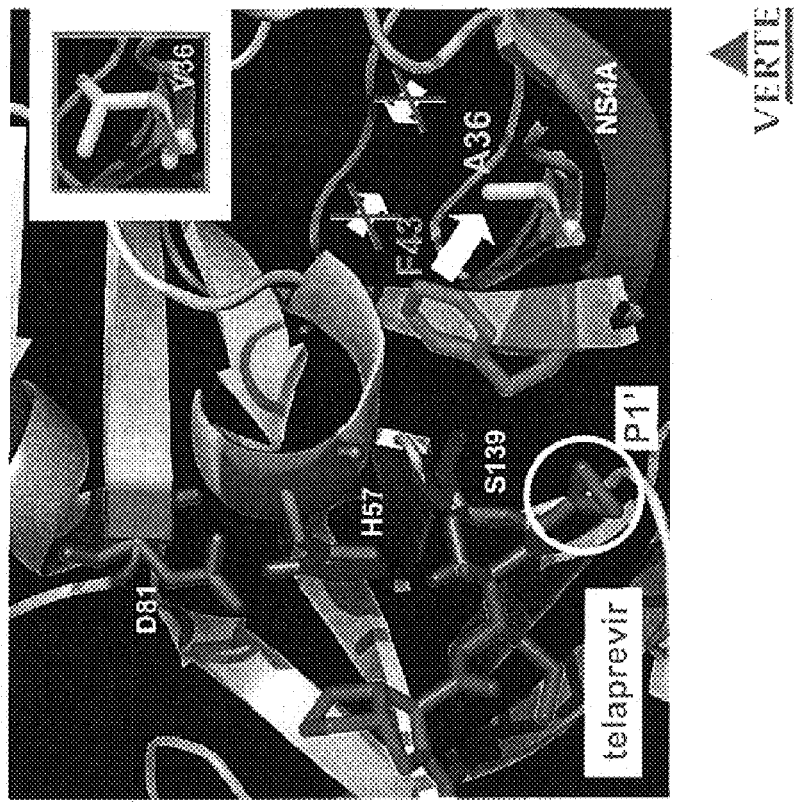
FIG. 15 shows the V36A variant in G1a/b with low-level resistance and worse fitness.
Figure 16:
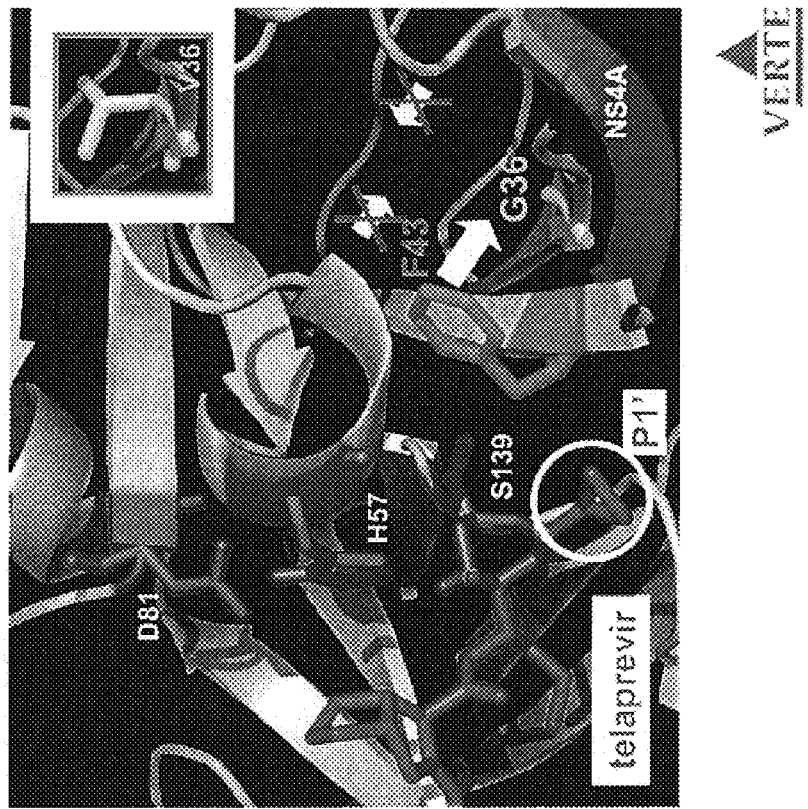
FIG. 16 shows the V36G variant in G1b with low-level resistance and worse fitness.
Figure 17:
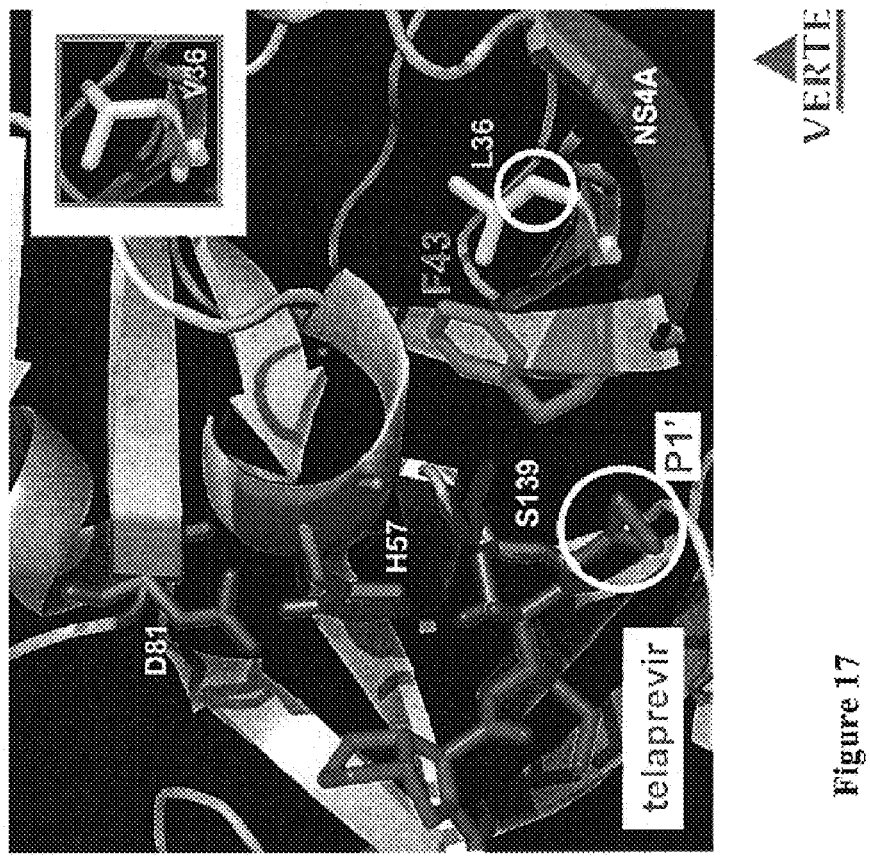
FIG. 17 shows the V36L variant with no resistance, which is also rare in G1.
Figure 18:
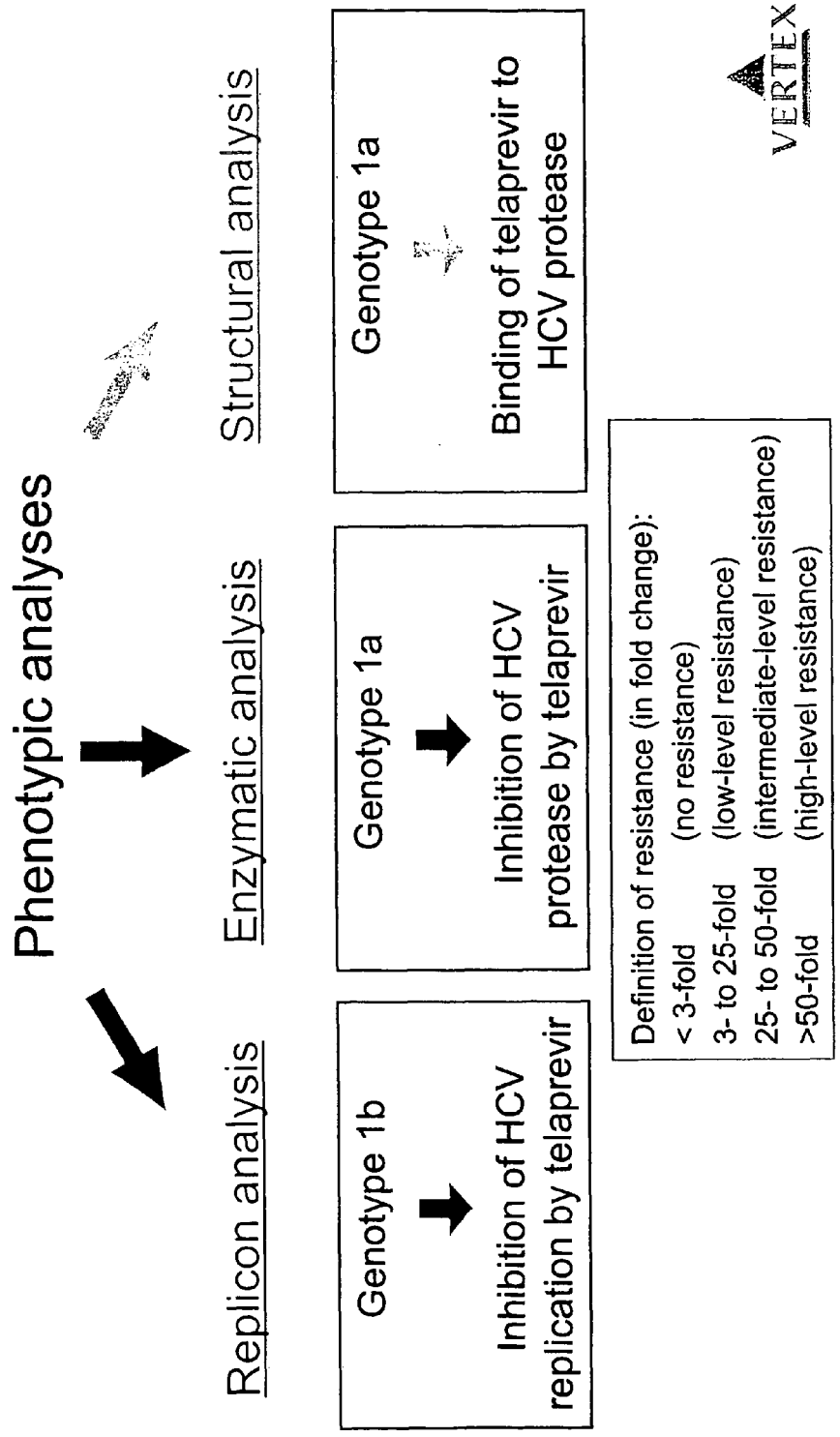
FIG. 18 also outlines the methods for phenotypic analyses of HCV viral variants.
Figure 20:
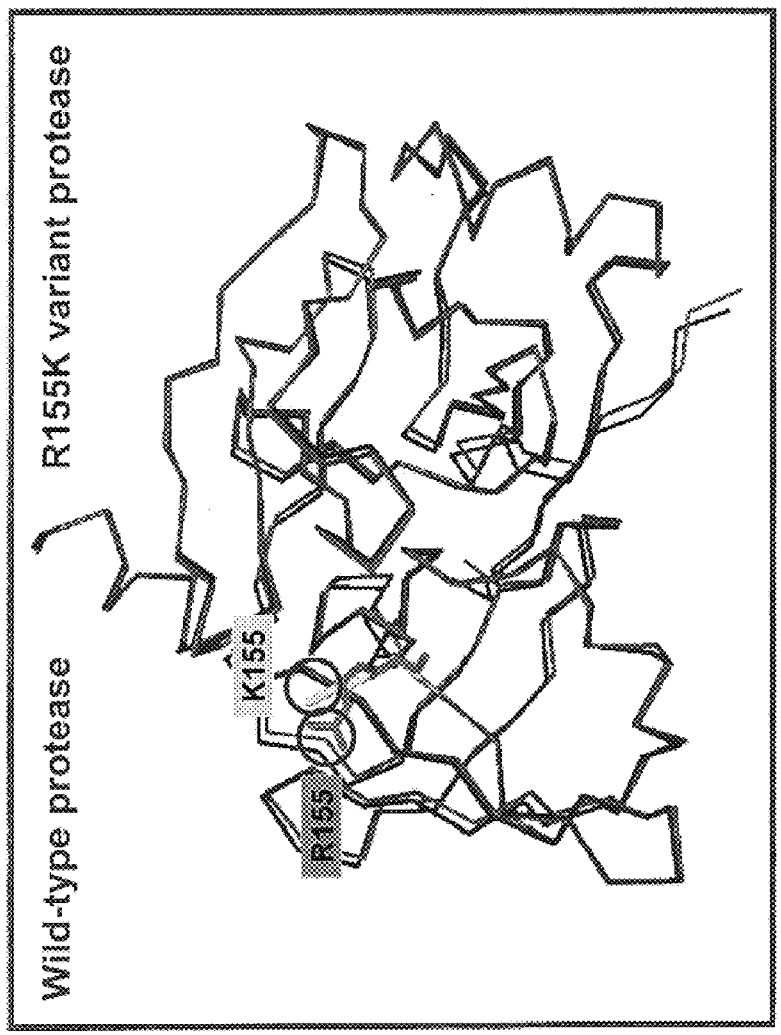
FIG. 20 shows the X-ray structure of the R155K variant protease.
Figure 21:
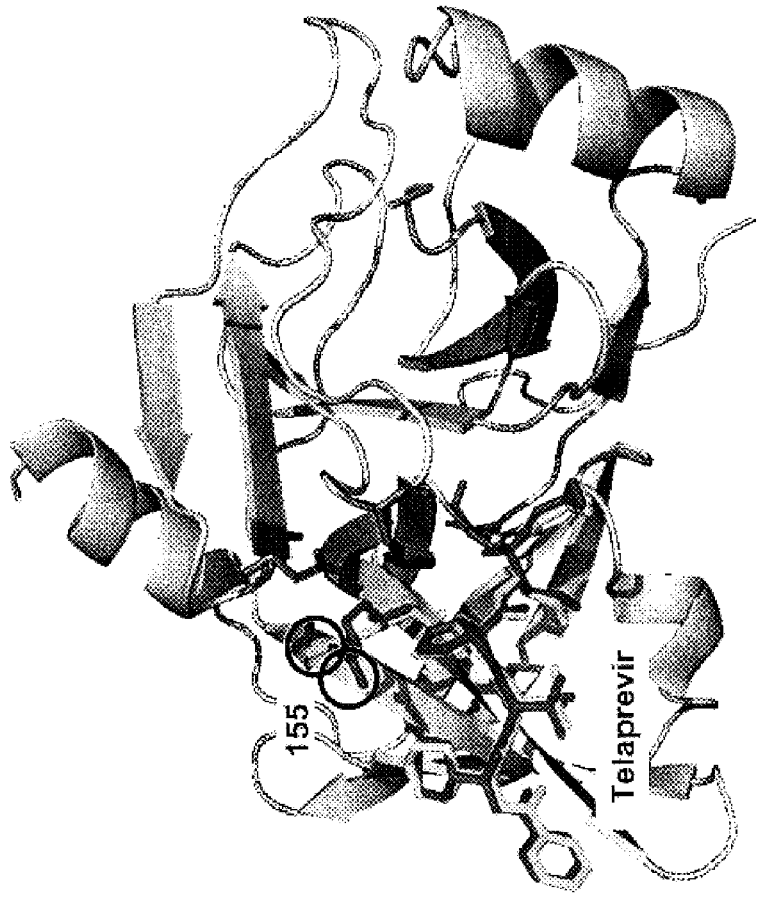
FIG. 21 shows the computer model of VX-950 binding to the R155K variant protease.
Figure 22:
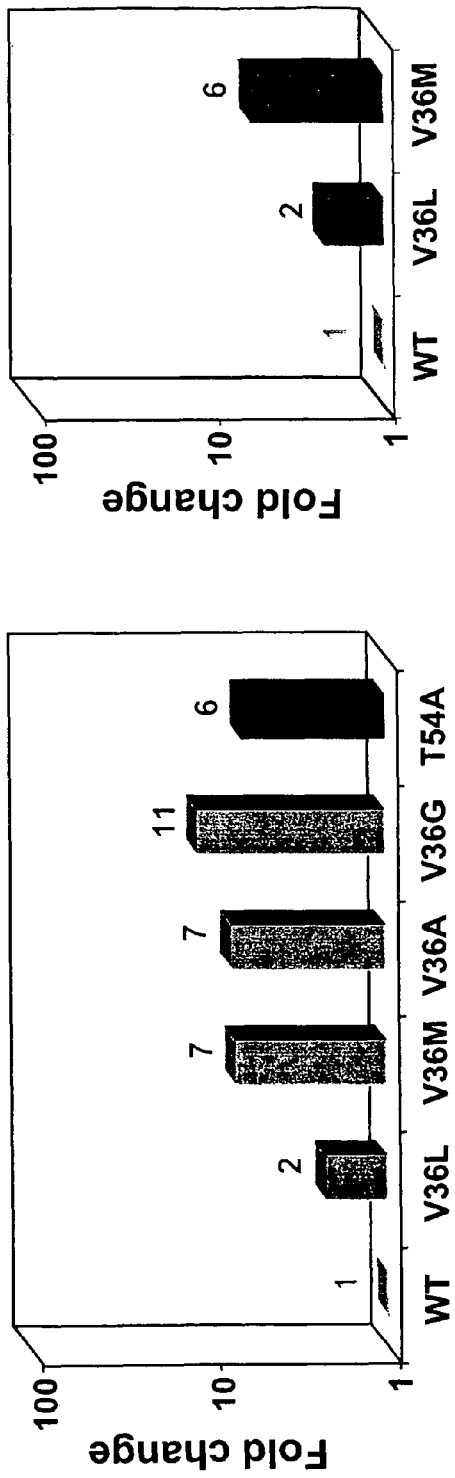
FIG. 22 shows that V36 or T54 substitutions confer low-level resistance to VX-950.
Figure 23:
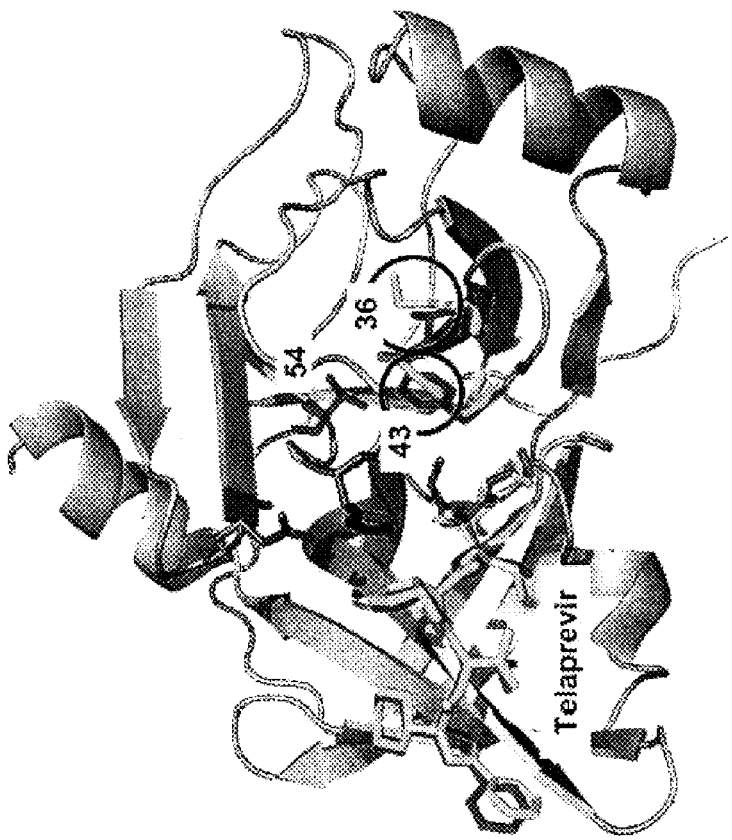
FIG. 23 shows the computer model of VX-950 binding to the V36M variant protease.
Figure 24:
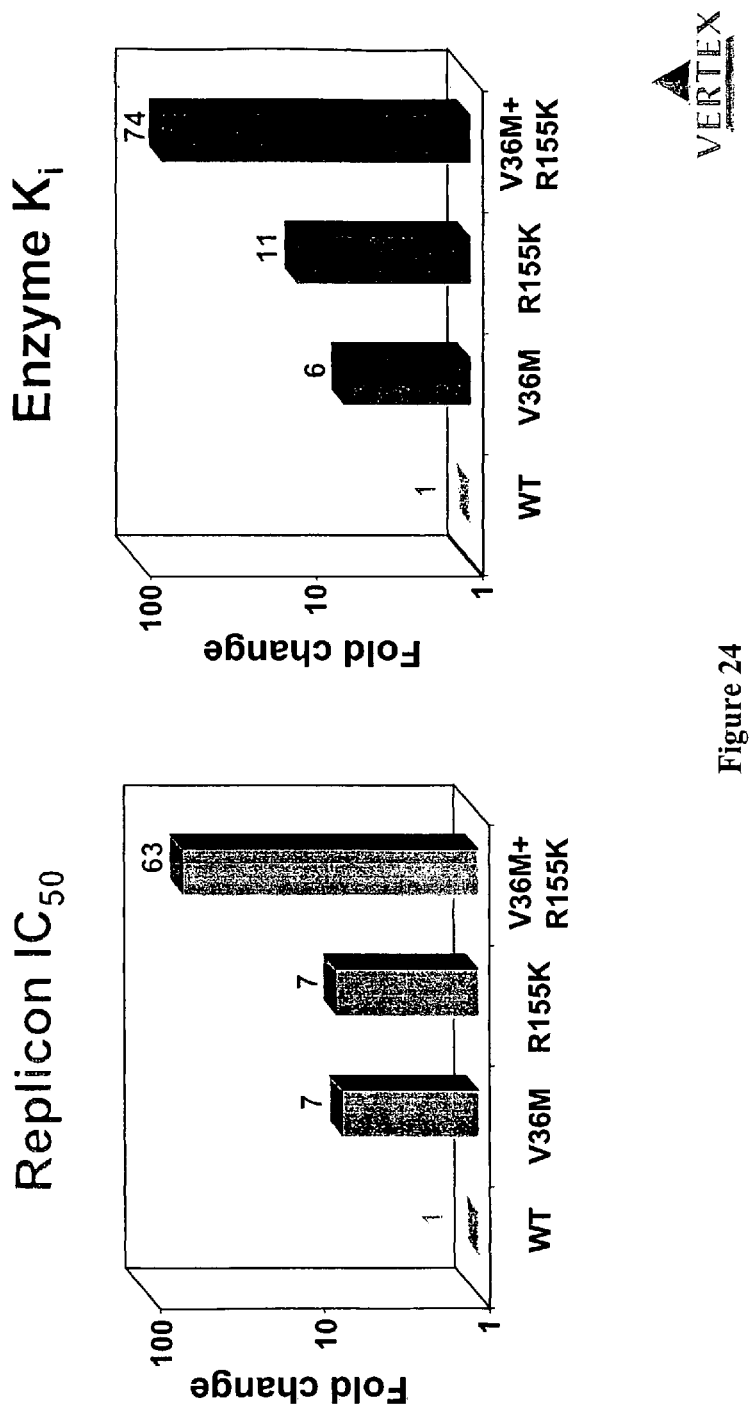
FIG. 24 shows that the V36M and R155K substitutions are additive in conferring resistance to VX-950.

The present invention relates to HCV variants. In particular, HCV variants that exhibit resistance to a protease inhibitor are provided. Also provided are methods and compositions related to the HCV variants. The methods and compositions are useful in identifying viral variants, including variants of an HCV and other viruses, evaluating and identifying anti-viral compounds, and developing and optimizing therapeutics against viral infections.

The present invention is based on a study that first characterized the extent of sequence diversity within the NS3 protease domain of an HCV isolated from 34 subjects enrolled in a clinical trial, Study VX04-950-101, before dosing with VX-950. Emergence of resistance to VX-950 in vivo was then monitored by sequence analysis of the protease NS3-4A region in the subjects after 14 days of dosing with VX-950. A follow-up sample was further collected 7 to 10 days after the end of dosing to see whether any drug-resistant mutations that developed during dosing was maintained in the plasma after removal of VX-950. Any mutations found to have increased in the population above baseline were considered potential drug resistant mutations. Because drug-resistance mutations may take some time to accumulate to a measurable level, the study included a new method to detect minor populations of variants (instead the dominant species in a population of wild-type viruses and viral variants), which involved obtaining sequences from many (e.g., 80-85) individual viral clones per subject per time point, so that viral variants that may emerge in 14 days of dosing with VX-950 with a sensitivity of down to about 5% of the population can be detected and identified. Such 80/85 individual viral clones may represent up to 80/85 different virions.

HCV Variants and Related Polynucleotides and Proteases

The present invention provides HCV variants. In particular embodiments, an HCV variant includes a polynucleotide sequence that encodes an HCV protease with reduced sensitivity to a protease inhibitor (also termed "a variant HCV protease"), such as VX-950. As used herein, a wild-type HCV refers to an HCV comprising a polynucleotide (also termed "a wild-type polynucleotide") that encodes an HCV protease with normal or desirable sensitivity to a protease inhibitor, and in particular embodiments, the protease inhibitor is VX-950. Similarly, a wild-type HCV protease refers to an HCV protease with normal or desirable sensitivity to a protease inhibitor, and in particular embodiments, the protease inhibitor is VX-950.

As used here in, an HCV can be an HCV of any genotype or subtype, for example, genotypes 1-6.

As used herein, an "NS3 protease" or an "HCV NS3 protease" refers to an HCV NS protein 3 or a portion thereof that has serine protease activity. For example, an NS3 protease can be the NS3 protein as represented by the first 631 amino acid sequence of SEQ ID NO:2 (685 amino acids); alternatively, an NS3 protease can be a protein as represented by the first 181 amino acids of SEQ ID NO:2; the 181-amino acid fragment is also referred to as the NS3 protease domain in the art. An NS3 protease can also be an NS3-NS4A protein complex, such as the complexes described in U.S. Pat. Nos. 6,653,127; 6,211,338. An "NS3 protease activity" means the protease activity of an HCV NS protein 3 or a portion thereof in the presence or absence of an NS4A protein or a biologically active portion thereof. An NS4A protein, such as for example as represented by the last 54 amino acid sequence of SEQ ID NO:2, usually functions as a co-factor for an NS3 protease and can form an NS3-NS4A serine protease complex; a biologically active portion of an NS4A protein refers to a fragment of an NS4A protein that retains the NS4A protein's function as a co-factor for an NS3 protease.

The present invention also provides isolated HCV variants, isolated variant HCV NS3 proteases, and isolated polynucleotide that encodes a variant HCV NS3 protease. The term "isolated" generally means separated and/or recovered from a component of natural environment of a subject virus, protease, or polynucleotide.

In certain embodiments, a variant HCV protease may be a variant HCV NS3 protease that comprises an amino acid sequence in which the amino acid(s) at one or more positions from positions 36, 41, 43, 54, 148, 155, or 156 of a wild-type HCV NS3 protease is(are) different from the amino acid at each corresponding position of the wild-type HCV NS3 protease. The wild type HCV NS3 protease may comprise an amino acid sequence of SEQ ID NO:2 or a portion thereof such as for example the first 181 amino acids of SEQ ID NO:2. The isolated HCV NS3 protease may comprise a biologically active analog or fragment of an HCV NS3 protease, for example, the isolated HCV NS3 protease may not have the N-terminal 5, 10, 15, 20, 30, 35, 40, 45, or 48 amino acids of SEQ ID NO:2.

Examples of amino acid substitutions or mutations at various positions of a variant HCV NS3 protease are shown in Tables 1-4. The Tables, Figures, and Examples herein also provide various data obtained with variant HCV NS3 proteases or HCV viral variants as compared to wild-type HCV NS3 proteases or wild-type HCVs.

Biologically active fragments or analogs of a variant HCV NS3 protease of the invention are also provided. Bartenschlager et al. (1994, J. Virology 68: 5045-55) described various fragments of HCV NS3 proteins, for example, the deletion of N-terminal 7 or 23 residues abolished cleavage at NS4B/5A site, but no effect on other cleave sites subjected to the NS3 protease activity; and the deletion of N-terminal 39 residues abolished cleavage at NS4B/5A and NS5A/5B sites and decreased the NS3 protease activity on the NS4A/4B site. Failla et al. (1995, J. Virology 69: 1769-77) described that the deletion of N-terminal 10 residues of a wild-type NS3 protein had no effect on the NS3 protease activity, the deletion of N-terminal 15 or 28 residues resulted in a NS3 protein with partial protease activity (normal cleavage at NS5A/5B, but lower at NS4A/4B and NS4B/5A sites), the deletion of N-terminal 49 residues resulted in a completely inactive NS3 protease, and the deletion of C-terminal 10 residues of the NS3 protease domain in the NS3 protein also resulted in a completely inactive NS3 proteases.

Expression systems are provided, for example, to make the variant HCV proteases of the invention. An expression system may include an expression vector that comprises an HCV polynucleotide of the invention. Suitable prokaryotic or eukaryotic vectors (e.g., expression vectors) comprising an HCV polynucleotide (or "nucleic acid," used interchangeably herein) of the invention can be introduced into a suitable host cell by an appropriate method (e.g., transformation, transfection, electroporation, infection), such that the polynucleotide is operably linked to one or more expression control elements (e.g., in the vector or integrated into the host cell genome). For production, host cells can be maintained under conditions suitable for expression (e.g., in the presence of inducer, suitable media supplemented with appropriate salts, growth factors, antibiotic, nutritional supplements, etc.), whereby the encoded polypeptide is produced. If desired, the encoded protein can be recovered and/or isolated (e.g., from the host cells or medium). It will be appreciated that the method of production encompasses expression in a host cell of a transgenic animal (see e.g., WO 92/03918). An expression system may be based on a cell-free system such as the RNA-protein fusion technology described in U.S. Pat. No. 6,258,558 or the in vitro "virus" described in U.S. Pat. No. 6,361,943. Ribosome display method can also be used, such as the method described in U.S. Pat. No. 5,843,701.

Various assays are provided, for example, assays suitable for phenotyping HCVs. The assays may be directed to measuring a viral activity (e.g., infection, replication, and/or release of viral particles) or an enzymatic activity (e.g. protease activity). Viral activity assays may employ cells or samples infected with a virus or viral variant of which the activity is to be measured. The cells or samples may be obtained from a patient such as a human patient. Alternatively, the cells or samples may be cultured and infected with a virus or viral variant in vitro. Viral activity assays may employ a replicon-based system, such as the replicon-based assays described in Trozzi et al. (13) and U.S. patent application publication No. 20050136400.

Enzymatic activity can be determined in cell-free or cell-based systems which generally include the enzyme of interest or a biologically active fragment or analog thereof and a substrate for the enzyme of interest. For example, U.S. patent application publication No. 20030162169 describes a surrogate cell-based system and method for assaying the activity of HCV NS3 protease. Trozzi et al. (13) describes an in vitro, cell-free protease assay that employs peptide substrates and HPLC systems.

The present invention takes advantage of the fact that the three-dimensional structure of NS3/4A protease has been resolved (see e.g., WO 98/11134). A three dimensional model of the variant protease of the invention can be obtained; compounds are designed or selected, for example based on their ability to interact with the three-dimensional structure of the variant protease, and the ability to bind to or interact with the protease is evaluated by modeling in silico and can be further evaluated by in vitro or in vivo assays.

The compound may be one identified from a combinatorial chemical library or prepared through rational drug design. In exemplary embodiments, the compound is a compound prepared through rational drug design and derived from the structure of a known protease inhibitor such as VX-950. Rational drug design also may be combined with a systematic method of large-scale screening experiments where potential protease inhibitor drug targets are tested with compounds from combinatorial libraries. Rational drug design is a focused approach, which uses information about the structure of a drug receptor or one of its natural ligands to identify or create candidate drugs. The three-dimensional structure of a protein can be determined using methods such as X-ray crystallography or nuclear magnetic resonance spectroscopy. In the present invention, the three dimensional structure of a variant HCV NS3 protease that contains one or more of the mutations of residues 36, 41, 43, 54, 148, 155, or 156 may now readily be determined using routine X-ray crystallographic and/or NMR spectroscopy techniques. Rational drug design also may be combined with a systematic method of large-scale screening experiments where potential protease inhibitor drug targets are tested with compounds from combinatorial libraries. Computer programs can be devised to search through databases containing the structures of many different chemical compounds. The computer can select those compounds that are most likely to interact with the variant HCV NS3 proteases, and such identified compound can be tested in assays (e.g., viral or enzymatic assays) suitable for evaluating protease inhibitors.

In certain embodiments, the identified compound is formulated into a composition comprising the compound and a pharmaceutically acceptable carrier, adjuvant or vehicle. Preferably the composition contains the compound in an amount effective to reduce the activity of an HCV NS3 serine protease. Even more preferably the composition is formulated for administration to a patient. The compositions also may comprise an additional agent selected from an immunomodulatory agent; an anti-viral agent; a second inhibitor of HCV protease; an inhibitor of another target in the HCV life cycle; a cytochrome P-450 inhibitor; or combinations thereof. The various compositions are described in greater details below.

In another aspect, the present invention provides antibodies that are specific to an HCV protease, in particular, an HCV NS3 protease with one or more amino acids altered as compared to a wild type HCV NS3 protease. The term "antibody" is used in the broadest sense and specifically covers, without limitation, intact monoclonal antibodies, polyclonal antibodies, chimeric antibodies, multispecific antibodies (e.g., bispecific antibodies) formed from at least two intact antibodies, and antibody fragments, so long as they exhibit the desired biological activity. The term "immunoglobulin" includes a variety of structurally related proteins that are not necessarily antibodies.

"Antibody fragments" comprise a portion of an intact antibody, preferably the antigen-binding or variable region of the intact antibody. Examples of antibody fragments include Fab, Fab', F(ab')$_2$, and Fv fragments; diabodies; linear antibodies (Zapata et al., Protein Eng., 8(10): 1057-1062 (1995)); single-chain antibody molecules; and multispecific antibodies formed from antibody fragments.

"Single-chain Fv" or "scFv" antibody fragments comprise the VH and VL domains of an antibody, wherein these domains are present in a single polypeptide chain. Preferably, the Fv polypeptide further comprises a polypeptide linker between the VH and VL domains that enables the scFv to form the desired structure for antigen binding. For a review of scFv see Pluckthun in The Pharmacology of Monoclonal Antibodies, vol. 113, Rosenburg and Moore, eds. (Springer-Verlag: New York, 1994), pp. 269-315.

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90: 6444-6448 (1993).

An antibody against a variant HCV protease may be developed from a known antibody against an HCV NS3 protein, for example through molecular evolution. U.S. patent application publication No. 20040214994 describes an human recombinant antibody against the HCV NS3 protein. Amino acid sequence variants of are prepared by introducing appropriate nucleotide changes into the DNA of a known antibody, or by peptide synthesis. Such variants include, for example, deletions from, and/or insertions into and/or substitutions of, residues within the amino acid sequences of the known antibody. Any combination of deletion, insertion, and substitution is made to arrive at the final construct, provided that the final construct possesses the desired characteristics. The amino acid changes also may alter post-translational processes of the antibody, such as changing the number or position of glycosylation sites.

An antibody of the invention may have diagnostic as well as therapeutic applications. In certain embodiments, an antibody of the invention is labeled. The various antibodies of the present disclosure can be used to detect or measure the expression of a variant HCV NS3 protease, and therefore, they are also useful in applications such as cell sorting and imaging (e.g., flow cytometry, and fluorescence activated cell sorting), for diagnostic or research purposes. As used herein, the terms "label" or "labeled" refers to incorporation of another molecule in the antibody. In one embodiment, the label is a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). In another embodiment, the label or marker can be therapeutic, e.g., a drug conjugate or toxin. Various methods of labeling polypeptides and glycoproteins are known in the art and may be used. Examples of labels for polypeptides include, but are not limited to, the following: radioisotopes or radionuclides (e.g., $^3$H, $^{14}$C, $^{15}$N, $^{35}$S, $^{90}$Y, $^{99}$Tc, $^{111}$In, $^{125}$I, $^{131}$I), fluorescent labels (e.g., FITC, rhodamine, lanthanide phosphors), enzymatic labels (e.g., horseradish peroxidase, beta-galactosidase, luciferase, alkaline phosphatase), chemiluminescent markers, biotinyl groups, predetermined polypeptide epitopes recognized by a secondary reporter (e.g., leucine zipper pair sequences, binding sites for secondary antibodies, metal binding domains, epitope tags), magnetic agents, such as gadolinium chelates, toxins such as pertussis toxin, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. In some embodiments, labels are attached by spacer arms of various lengths to reduce potential steric hindrance.

In certain aspects, kits for use in detecting the presence of an HCV viral, a variant HCV NS3 polynucleotide, or a variant HCV protease in a biological sample can also be prepared. Such kits may include an antibody that recognizes a variant HCV NS3 protease of the invention, as well as one or more ancillary reagents suitable for detecting the presence of a complex between the antibody and the variant protease or a portion thereof. Alternatively, such kits may include a probe or primer of the invention, such a probe or primer can hybridize with a variant HCV NS3 polynucleotide of the invention under stringent conditions. A probe or primer of the invention may be suitable for PCR or RT-PCR that can be employed to detect a subject of interest. Alternatively, such kits may be based on PCR or non-PCR based HCV diagnostic kits available commercially, e.g., Roche Cobas Amplicor system and Bayer Versant system, including RNA 3.0 assay (bDNA) and RNA Qualitative Assay (TMA). The AMPLICOR HCV MONITOR® Test, v2.0 is an in vitro nucleic acid amplification test for the quantification of HCV RNA in human serum or plasma. The VERSANT® HCV RNA 3.0 Assay (bDNA) is a viral load assay that has been proven to reliably detect a 2 log10 drop. The VERSANT® HCV RNA Qualitative Assay is based on state-of-the-art Transcription-Mediated Amplification (TMA) technology.

Pharmaceutical Compositions and Formulations

Another aspect of the invention provides pharmaceutical compositions or formulations including a compound of the invention, for example, a secondary compound that is identified as being able to rescue the activity of VX-950, or a compound that is identified as effective against an HCV variant (e.g., capable of reducing replication of the viral variant) and/or a variant HCV NS3 protease (e.g., capable of reducing the enzymatic activity of the variant protease).

Another aspect of the invention provides uses of a compound of the invention in the manufacture of a medicament, such as a medicament for treating an HCV infection in a patient.

Another aspect of the invention provides methods for treating an HCV infection in a patient. Such methods generally comprise administering to the patient a pharmaceutically or therapeutically effective amount of a compound of the invention alone or in combination (sequentially or contemporaneously) with another anti-viral agent. "Effective amount" of a compound or agent generally refers to those amounts effective to reproducibly reduce HCV NS3 protease expression or activity, HCV production, replication, or virulence, HCV infection, or produce an amelioration or alleviation of one or more of the symptoms of HCV infection in comparison to the levels of these parameters in the absence of such a compound or agent.

In another aspect, the methods and compositions of this invention include a protease inhibitor (e.g., VX-950) and another anti-viral agent, preferably an anti-HCV agent. Combination therapy targeting HCV is also described in U.S. Pat. Nos. 6,924,270; 6,849,254.

Another anti-viral agent may also be a protease inhibitor, particularly an HCV protease inhibitor. HCV protease inhibitors known in the art include VX-950 (FIG. 8), BILN 2061 (FIG. 8, see also PCT Publication No. WO 00/59929; U.S. Pat. No. 6,608,027), compound 1 (13), Inhibitors A, B, and C (PCT Publication No. WO 04/039970). Potential HCV protease inhibitors have also been described in PCT and U.S. patent application publication Nos. WO 97/43310, US 20020016294, WO 01/81325, WO 02/08198, WO 01/77113, WO 02/08187, WO 02/08256, WO 02/08244, WO 03/006490, WO 01/74768, WO 99/50230, WO 98/17679, WO 02/48157, US 20020177725, WO 02/060926, US 20030008828, WO 02/48116, WO 01/64678, WO 01/07407, WO 98/46630, WO 00/59929, WO 99/07733, WO 00/09588, US 20020016442, WO 00/09543, WO 99/07734, US 20020032175, US 20050080017, WO 98/22496, WO 02/079234, WO 00/31129, WO 99/38888, WO 99/64442, WO 2004072243, and WO 02/18369, and U.S. Pat. Nos. 6,018,020; 6,265,380; 6,608,027; 5,866,684; M. Llinas-Brunet et al., Bioorg. Med. Chem. Lett., 8, pp. 1713-18 (1998); W. Han et al., Bioorg. Med. Chem. Lett., 10, 711-13 (2000); R. Dunsdon et al., Bioorg. Med. Chem. Lett., 10, pp. 1571-79 (2000); M. Llinas-Brunet et al., Bioorg. Med. Chem. Lett., 10, pp. 2267-70 (2000); and S. LaPlante et al., Bioorg. Med. Chem. Lett., 10, pp. 2271-74 (2000). A number of NS3 protease inhibitors have also been developed by Schering Corp., Schering A.G., and other companies, and they are described in U.S. patent application publication Nos. 20050249702; 20050153900; 20050245458; 20050222047; 20050209164; 20050197301; 20050176648; 20050164921; 20050119168; 20050085425; 20050059606; 20030207861; 20020147139; 20050143439; 20050059606; 20050107304; 20050090450; 20040147483; 20040142876; 20040077600; 20040018986; 20030236242; 20030216325; 20030207861; U.S. Pat. Nos. 6,962,932; 6,914,122; 6,911,428; 6,846,802; 6,838,475.

Anti-viral agents may also include, but are not limited to, immunomodulatory agents, such as alpha-, beta-, and gamma-interferons, pegylated derivatized interferon-alpha compounds, and thymosin; other anti-viral agents, such as ribavirin, amantadine, and telbivudine; other inhibitors of hepatitis C proteases (NS2-NS3 inhibitors and NS3-NS4A inhibitors); inhibitors of other targets in the HCV life cycle, including helicase and polymerase inhibitors; inhibitors of internal ribosome entry; broad-spectrum viral inhibitors, such as IMPDH inhibitors (e.g., compounds of U.S. Pat. Nos. 5,807,876, 6,498,178, 6,344,465, 6,054,472, WO 97/40028, WO 98/40381, WO 00/56331, and mycophenolic acid and derivatives thereof, and including, but not limited to VX-497, VX-148, and/or VX-944); or combinations of any of the above. See also W. Markland et al., Antimicrobial & Antiviral Chemotherapy, 44, p. 859 (2000) and U.S. Pat. No. 6,541,496.

The following definitions are used herein:

"Peg-Intron" means PEG-Intron®, peginteferon alfa-2b, available from Schering Corporation, Kenilworth, N.J.; "Intron" means Intron-A®, interferon alpha-2b available from Schering Corporation, Kenilworth, N.J.; "ribavirin" means ribavirin (1-beta-D-ribofuranosyl-1H-1,2,4-triazole-3-carboxamide, available from ICN Pharmaceuticals, Inc., Costa Mesa, Calif.; described in the Merck Index, entry 8365, Twelfth Edition; also available as Rebetol® from Schering Corporation, Kenilworth, N.J., or as Copegus® from Hoffmann-La Roche, Nutley, N.J.; "Pagasys" means Pegasys®, peg-interferon alfa-2a available Hoffmann-La Roche, Nutley, N.J.; "Roferon" means Roferon®, recombinant interferon alpha-2a available from Hoffmann-La Roche, Nutley, N.J.; "Berofor" means Berofor®, interferon alpha-2 available from Boehringer Ingelheim Pharmaceutical, Inc., Ridgefield, Conn.; Sumiferon®, a purified blend of natural alpha interferons such as Sumiferon available from Sumitomo, Japan; Wellferon®, interferon alpha n1 available from Glaxo Wellcome Ltd., Great Britain; Alferon®, a mixture of natural alpha interferons made by Interferon Sciences, and available from Purdue Frederick Co., CT.

The term "interferon" as used herein means a member of a family of highly homologous species-specific proteins that inhibit viral replication and cellular proliferation, and modulate immune response, such as interferon alpha, interferon beta, or interferon gamma. The Merck Index, entry 5015, Twelfth Edition. According to one embodiment of the present invention, the interferon is alpha-interferon. According to another embodiment, a therapeutic combination of the present invention utilizes natural alpha interferon 2a. Alternatively, the therapeutic combination of the present invention utilizes natural alpha interferon 2b. In another embodiment, the therapeutic combination of the present invention utilizes recombinant alpha interferon 2a or 2b. In yet another embodiment, the interferon is pegylated alpha interferon 2a or 2b. Interferons suitable for the present invention include: (a) Intron (interferon-alpha 2B, Schering Plough), (b) Peg-Intron, (c) Pegasys, (d) Roferon, (e) Berofor, (f) Sumiferon, (g) Wellferon, (h) consensus alpha interferon available from Amgen, Inc., Newbury Park, Calif., (i) Alferon; (j) Viraferon®; (k) Infergen®.

A protease inhibitor can be administered orally, whereas Interferon is not typically administered orally. Nevertheless, nothing herein limits the methods or combinations of this invention to any specific dosage forms or regime. Thus, each component of a combination according to this invention may be administered separately, together, sequentially or simultaneously, or in any combination thereof.

In one embodiment, the protease inhibitor and interferon are administered in separate dosage forms. In one embodiment, any additional agent is administered as part of a single dosage form with the protease inhibitor or as a separate dosage form. As this invention involves a combination of compounds and/or agents, the specific amounts of each compound or agent may be dependent on the specific amounts of each other compound in the combination. Dosages of interferon are typically measured in IU (e.g., about 4 million IU to about 12 million IU).

Accordingly, agents (whether acting as an immunomodulatory agent or otherwise) that may be used in combination with a compound of this invention include, but are not limited to, interferon-alpha 2B (Intron A, Schering Plough); Rebatron (Schering Plough, Inteferon-alpha 2B+Ribavirin); pegylated interferon alpha (Reddy, K. R. et al. "Efficacy and Safety of Pegylated (40-kd) interferon alpha-2a compared with interferon alpha-2a in noncirrhotic patients with chronic hepatitis C," Hepatology, 33, pp. 433-438 (2001); consensus interferon (Kao, J. H., et al., "Efficacy of Consensus Interferon in the Treatment of Chronic Hepatitis," J. Gastroenterol. Hepatol. 15, pp. 1418-1423 (2000), interferon-alpha 2A (Roferon A; Roche), lymphoblastoid or "natural" interferon; interferon tau (Clayette, P. et al., "IFN-tau, A New Interferon Type I with Antiretroviral activity," Pathol. Biol. (Paris) 47, pp. 553-559 (1999); interleukin 2 (Davis, G. L. et al., "Future Options for the Management of Hepatitis C," Seminars in Liver Disease, 19, pp. 103-112 (1999); Interleukin 6 (Davis, G. L. et al., supra; interleukin 12 (Davis, G. L. et al., supra; Ribavirin; and compounds that enhance the development of type 1 helper T cell response (Davis, G. L., et al., supra. Interferons may ameliorate viral infections by exerting direct antiviral effects and/or by modifying the immune response to infection. The antiviral effects of interferons are often mediated through inhibition of viral penetration or uncoating, synthesis of viral RNA, translation of viral proteins, and/or viral assembly and release.

Compounds that stimulate the synthesis of interferon in cells (Tazulakhova, E. B. et al., "Russian Experience in Screening, analysis, and Clinical Application of Novel Interferon Inducers," J. Interferon Cytokine Res., 21 pp. 65-73) include, but are not limited to, double stranded RNA, alone or in combination with tobramycin, and Imiquimod (3M Pharmaceuticals; Sauder, D. N., "Immunomodulatory and Pharmacologic Properties of Imiquimod," J. Am. Acad. Dermatol., 43 pp. S6-11 (2000).

Other non-immunomodulatory or immunomodulatory compounds may be used in combination with a compound of this invention including, but not limited to, those specified in WO 02/18369, which is incorporated herein by reference (see, e.g., page 273, lines 9-22 and page 274, line 4 to page 276, line 11, which is incorporated herein by reference in its entirety).

Compounds that stimulate the synthesis of interferon in cells (Tazulakhova et al., J. Interferon Cytokine Res. 21, 65-73)) include, but are not limited to, double stranded RNA, alone or in combination with tobramycin and Imiquimod (3M Pharmaceuticals) (Sauder, J. Am. Arad. Dermatol. 43, S6-11 (2000)).

Other compounds known to have, or that may have, HCV antiviral activity include, but are not limited to, Ribavirin (ICN Pharmaceuticals); inosine 5'-monophosphate dehydrogenase inhibitors (VX-497 formula provided herein); amantadine and rimantadine (Younossi et al., In Seminars in Liver Disease 19, 95-102 (1999)); LY217896 (U.S. Pat. No. 4,835,168) (Colacino, et al., Antimicrobial Agents & Chemotherapy 34, 2156-2163 (1990)); and 9-Hydroxyimino-6-methoxy-1,4a-dimethyl 1,2,3,4,4a,9,10,10a-octahydro-phena-nthrene-1-carboxylic acid methyl ester; 6-Methoxy-1, 4a dimethyl-9-(4-methyl-piperazin-1-ylimino)-1,2,3,4,4a,9, 10,10a-octahydro-p-henanthrene-1carboxylic acid methyl ester-hydrochloride; 1-(2-Chloro-phenyl)-3-(2,2-Biphenyl-ethyl)-urea (U.S. Pat. No. 6,127,422).

Formulations, doses, and routes of administration for the foregoing molecules are either taught in the references cited below, or are well-known in the art as disclosed, for example, in F. G. Hayden, in Goodman & Gilman's The Pharmacological Basis of Therapeutics, Ninth Edition, Hardman et al., Eds., McGraw-Hill, New York (1996), Chapter 50, pp. 1191-1223, and the references cited therein. Alternatively, once a compound that exhibits HCV antiviral activity, particularly antiviral activity against a drug-resistant strain of HCV, has been identified, a pharmaceutically effective amount of that compound can be determined using techniques that are well-known to the skilled artisan. Note, for example, Benet et al., in Goodman & Gilman's The Pharmacological Basis of Therapeutics, Ninth Edition, Hardman et al., Eds., McGraw-Hill, New York (1996), Chapter 1, pp. 3-27, and the references cited therein. Thus, the appropriate formulations, dose(s) range, and dosing regimens, of such a compound can be easily determined by routine methods.

The compositions related to combination therapies of the present invention can be provided to a cell or cells, or to a human patient, either in separate pharmaceutically acceptable formulations administered simultaneously or sequentially, formulations containing more than one therapeutic agent, or by an assortment of single agent and multiple agent formulations. Regardless of the route of administration, these drug combinations form an anti-HCV effective amount of components of the pharmaceutically acceptable formulations.

A large number of other immunomodulators and immunostimulants that can be used in the methods of the present invention are currently available and include: AA-2G; adamantylamide dipeptide; adenosine deaminase, Enzon adjuvant, Alliance; adjuvants, Ribi; adjuvants, Vaxcel; Adjuvax; agelasphin-11; AIDS therapy, Chiron; algal glucan, SRI; alganunulin, Anutech; Anginlyc; anticellular factors, Yeda; Anticort; antigastrin-17 immunogen, Ap; antigen delivery system, Vac; antigen formulation, IDBC; antiGnRH immunogen, Aphton; Antiherpin; Arbidol; azarole; Bay-q-8939; Bay-r-1005; BCH-1393; Betafectin; Biostim; BL-001; BL-009; Broncostat; Cantastim; CDRI-84-246; cefodizime; chemokine inhibitors, ICOS; CMV peptides, City of Hope; CN-5888; cytokine-releasing agent, St; DHEAS, Paradigm; DISC TA-HSV; J07B; I01A; I01Z; ditiocarb sodium; ECA-10-142; ELS-1; endotoxin, Novartis; FCE-20696; FCE-24089; FCE-24578; FLT-3 ligand, Immunex; FR-900483; FR-900494; FR-901235; FTS-Zn; G-proteins, Cadus; gludapcin; glutaurine; glycophosphopeptical; GM-2; GM-53; GMDP; growth factor vaccine, EntreM; H-BIG, NABI; H-CIG, NABI; HAB439; *Helicobacter pylori* vaccine; herpes-specific immune factor; HIV therapy, United Biomed; HyperGAM+CF; ImmuMax; Immun BCG; immune therapy, Connective; immunomodulator, Evans; immunomodulators, Novacell; imreg-1; imreg-2; Indomune;

inosine pranobex; interferon, Dong-A (alpha2); interferon, Genentech (gamma); interferon, Novartis (alpha); interleukin-12, Genetics Ins; interleukin-15, Immunex; interleukin-16, Research Cor; ISCAR-1; J005X; L-644257; licomarasminic acid; LipoTher; LK-409, LK-410; LP-2307; LT (R1926); LW-50020; MAF, Shionogi; MDP derivatives, Merck; met-enkephalin, TNI; methylfurylbutyrolactones; MIMP; mirimostim; mixed bacterial vaccine, Tem, MM-1; moniliastat; MPLA, Ribi; MS-705; murabutide; marabutide, Vacsyn; muramyl dipeptide derivative; muramyl peptide derivatives myelopid; -563; NACOS-6; NH-765; NISV, Proteus; NPT-16416; NT-002; PA-485; PEFA-814; peptides, Scios; peptidoglycan, Pliva; Perthon, Advanced Plant; PGM derivative, Pliva; Pharmaprojects No. 1099; No. 1426; No. 1549; No. 1585; No. 1607; No. 1710; No. 1779; No. 2002; No. 2060; No. 2795; No. 3088; No. 3111; No. 3345; No. 3467; No. 3668; No. 3998; No. 3999; No. 4089; No. 4188; No. 4451; No. 4500; No. 4689; No. 4833; No. 494; No. 5217; No. 530; pidotimod; pimelautide; pinafide; PMD-589; podophyllotoxin, Conpharm; POL-509; poly-ICLC; poly-ICLC, Yamasa Shoyu; PolyA-PolyU; Polysaccharide A; protein A, Berlux Bioscience; PS34WO; Pseudomonas MAbs, Teijin; Psomaglobin; PTL-78419; Pyrexol; pyriferone; Retrogen; Retropep; RG-003; Rhinostat; rifamaxil; RM-06; Rollin; romurtide; RU-40555; RU-41821; Rubella antibodies, ResCo; S-27649; SB-73; SDZ-280-636; SDZ-MRL953; SK&F-107647; SL04; SL05; SM-4333; Solutein; SRI-62-834; SRL-172; ST-570; ST-789; staphage lysate; Stimulon; suppressin; T-150R1; T-LCEF; tabilautide; temurtide; Theradigm-HBV; Theradigm-HBV; Theradigm-HSV; THF, Pharm & Upjohn; THF, Yeda; thymalfasin; thymic hormone fractions; thymocartin; thymolymphotropin; thymopentin; thymopentin analogues; thymopentin, Peptech; thymosin fraction 5, Alpha; thymostimulin; thymotrinan; TMD-232; TO-115; transfer factor, Viragen; tuftsin, Selavo; ubenimex; Ulsastat; ANGG–; CD-4+; Collag+; COLSF+; COM+; DA-A+; GAST–; GF-TH+; GP-120–; IF+; IF-A+; IF-A-2+; IF-B+; IF-G+; IF-G-1B+; IL-2+; IL-12+; IL-15+; IM+; LHRH–; LIPCOR+L LYM-B+; LYM-NK+; LYM-T+; OPI+; PEP+; PHG-MA+; RNA-SYN–; SY-CW–; TH-A-I+; TH-5+; TNF+; UN.

Representative nucleoside and nucleotide compounds useful in the present invention include, but are not limited to: (+)-cis-5-fluoro-1-[2-(hydroxymethyl)-[1,3-oxathiolan-5yl]cytosine; (–)-2'-deoxy-3'-thiocytidine-5'-triphospbate (3TC); (–)-cis-5-fluoro-1-[2(hydroxy-methyl)-[1,3-oxathiolan-5-yl]cytosine (FTC); (–)2',3', dideoxy-3'-thiacytidine [(–)-SddC]; 1-(2'-deoxy-2'-fluoro-beta-D-arabinofuranosyl)-5-iodocytosine (FIAC); 1-(2'-deoxy-2'-fluoro-beta-D-arabinofuranosyl)-5-iodocytosine triphosphate (FIACTP); 1-(2'-deoxy-2'-fluoro-beta-D-arabinofuranosyl)-5-m-ethyluracil (FMAU); 1-beta-D-ribofuranosyl-1,2,4-triazole-3-carboxamide; 2',3'-dideoxy-3'-fluoro-5-methyl-dexocytidine (FddMeCyt); 2',3'-dideoxy-3'-chloro-5-methyl-dexocytidine (ClddMeCyt); 2',3'-dideoxy-3'-amino-5-methyl-dexocytidine (AddMeCyt); 2',3'-dideoxy-3'-fluoro-5-methyl-cytidine (FddMeCyt); 2',3'-dideoxy-3'-chloro-5-methyl-cytidine (ClddMeCyt); 2',3'-dideoxy-3'-amino-5-methyl-cytidine (AddMeCyt); 2',3'-dideoxy-3'-fluorothymidine (FddThd); 2',3'-dideoxy-beta-L-5-fluoroc-ytidine (beta-L-FddC) 2',3'-dideoxy-beta-L-5-thiacytidine; 2',3'-dideoxy-beta-L-5-cytidine (beta-L-ddC); 9-(1,3-dihydroxy-2-propoxym-ethyl)guanine; 2'-deoxy-3'-thia-5-fluorocytosine; 3'-amino-5-methyl-dexoc-ytidine (AddMeCyt); 2-amino-1,9-[(2-hydroxymethyl-1-(hydroxymethyl)ethoxy]methyl]-6H-purin-6-one (gancyclovir); 2-[2-(2-amino-9H-purin-9y)ethyl)-1,3-propandil diacetate(famciclovir); 2-amino-1,9-dihydro-9-[(2-hydro-xy-ethoxy)methyl]6H-purin-6-one (acyclovir); 9-(4-hydroxy-3-hydroxymethyl-but-1-yl)guanine (penciclovir); 9-(4-hydroxy-3-hydroxymethyl-but-1-yl)-6-deoxy-guanine diacetate(famciclovir); 3'-azido-3'-deoxythymidine (AZT); 3'-chloro-5-methyl-dexocytidine (ClddMeCyt); 9-(2-phosphonyl-methoxyethyl-)-2',6'-diaminopurine-2',3'-dideoxyriboside; 9-(2-phosphonylmethoxyethyl)-adenine (PMEA); acyclovir triphosphate (ACVTP); D-carbocyclic-2'-deoxyguan-osine (CdG); dideoxy-cytidine; dideoxy-cytosine (ddC); dideoxy-guanine (ddG); dideoxy-inosine (ddI); E-5-(2-bromovinyl)-2'-deoxyuridine triphosphate; fluoro-arabinofuranosyl-iodouracil; 1-(2'-deoxy-2'-fluoro-1-beta-D-arabinofuranosyl)-5-iodo-uracil (FIAU); stavudine; 9-beta-D-arabinofuranosyl-9H-purine-6-amine monohydrate (Ara-A); 9-beta-D-arabinofuranosyl-9H-purine-6-amine-5'-monophosphate monohydrate (Ara-AMP); 2-deoxy-3'-thia-5-fluorocytidine; 2',3'-dideoxy-guanine; and 2',3'-dideoxy-guanosine.

Synthetic methods for the preparation of nucleosides and nucleotides useful in the present invention are well known in the art as disclosed in Acta Biochim Pol., 43, 25-36 (1996); Swed. Nucleosides Nucleotides 15, 361-378 (1996); Synthesis 12, 1465-1479 (1995); Carbohyd. Chem. 27, 242-276 (1995); Chena Nucleosides Nucleotides 3, 421-535 (1994); Ann. Reports in Med. Chena, Academic Press; and Exp. Opin. Invest. Drugs 4, 95-115 (1995).

The chemical reactions described in the references cited above are generally disclosed in terms of their broadest application to the preparation of the compounds of this invention. Occasionally, the reactions may not be applicable as described to each compound included within the scope of compounds disclosed herein. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional will be applicable to the preparation of the corresponding compounds of this invention. In all preparative methods, all starting materials are known or readily preparable from known starting materials.

While nucleoside analogs are generally employed as antiviral agents as is, nucleotides (nucleoside phosphates) sometimes have to be converted to nucleosides in order to facilitate their transport across cell membranes. An example of a chemically modified nucleotide capable of entering cells is S-1-3-hydroxy-2-phosphonylmethoxypropyl cytosine (HPMPC, Gilead Sciences). Nucleoside and nucleotide compounds used in this invention that are acids can form salts. Examples include salts with alkali metals or alkaline earth metals, such as sodium, potassium, calcium, or magnesium, or with organic bases or basic quaternary ammonium salts.

The skilled artisan may also chose to administer a cytochrome P450 monooxygenase inhibitor. Such inhibitors may be useful in increasing liver concentrations and/or increasing blood levels of compounds that are inhibited by cytochrome P450. For an embodiment of this invention that involves a CYP inhibitor, any CYP inhibitor that improves the pharmacokinetics of the relevant NS3/4A protease may be included in a composition and/or used in a method of this invention. These CYP inhibitors include, but are not limited to, ritonavir (WO 94/14436), ketoconazole, troleandomycin, 4-methylpyrazole, cyclosporin, clomethiazole, cimetidine, itraconazole, fluconazole, miconazole, fluvoxamine, fluoxetine, nefazodone, sertraline, indinavir, nelfinavir, amprenavir, fosamprenavir, saquinavir, lopinavir, delavirdine, erythromycin, VX-944, and VX-497. Preferred CYP inhibitors include ritonavir, ketoconazole, troleandomycin, 4-methylpyrazole, cyclosporin, and clomethiazole. For preferred dosage forms of ritonavir, see U.S. Pat. No. 6,037,157, and the documents cited therein: U.S. Pat. No. 5,484,801, U.S. application Ser. No. 08/402,690, and International Applications WO 95/07696 and WO 95/09614).

Methods for measuring the ability of a compound to inhibit cytochrome P50 monooxygenase activity are known (see U.S. Pat. No. 6,037,157 and Yun, et al. Drug Metabolism & Disposition, vol. 21, pp. 403-407 (1993).

Immunomodulators, immunostimulants and other agents useful in the combination therapy methods of the present invention can be administered in amounts lower than those conventional in the art. For example, interferon alpha is typically administered to humans for the treatment of HCV infections in an amount of from about $1 \times 10^6$ units/person three times per week to about 10.times.106 units/person three times per week (Simon et al., Hepatology 25: 445-448 (1997)). In the methods and compositions of the present invention, this dose can be in the range of from about $0.1 \times 10^6$ units/person three times per week to about $7.5 \times 10^6$ units/person three times per week; more preferably from about $0.5 \times 10^6$ units/person three times per week to about $5 \times 10^6$ units/person three times per week; most preferably from about $1 \times 10^6$ units/person three times per week to about $3 \times 10^6$ units/person three times per week. Due to the enhanced hepatitis C virus antiviral effectiveness of immunomodulators, immunostimulants or other anti-HCV agent in the presence of the HCV serine protease inhibitors of the present invention, reduced amounts of these immunomodulators/immunostimulants can be employed in the treatment methods and compositions contemplated herein. Similarly, due to the enhanced hepatitis C virus antiviral effectiveness of the present HCV serine protease inhibitors in the presence of immunomodulators and immunostimulants, reduced amounts of these HCV serine protease inhibitors can be employed in the methods and compositions contemplated herein. Such reduced amounts can be determined by routine monitoring of hepatitis C virus titers in infected patients undergoing therapy. This can be carried out by, for example, monitoring HCV RNA in patients' serum by slot-blot, dot-blot, or RT-PCR techniques, or by measurement of HCV surface or other antigens. Patients can be similarly monitored during combination therapy employing the HCV serine protease inhibitors disclosed herein and other compounds having anti-HCV activity, for example nucleoside and/or nucleotide anti-viral agents, to determine the lowest effective doses of each when used in combination.

In the methods of combination therapy disclosed herein, nucleoside or nucleotide antiviral compounds, or mixtures thereof, can be administered to humans in an amount in the range of from about 0.1 mg/person/day to about 500 mg/person/day; preferably from about 10 mg/person/day to about 300 mg/person/day; more preferably from about 25 mg/person/day to about 200 mg/person/day; even more preferably from about 50 mg/person/day to about 150 mg/person/day; and most preferably in the range of from about 1 mg/person/day to about 50 mg/person/day.

Doses of compounds can be administered to a patient in a single dose or in proportionate doses. In the latter case, dosage unit compositions can contain such amounts of submultiples thereof to make up the daily dose. Multiple doses per day can also increase the total daily dose should this be desired by the person prescribing the drug.

The regimen for treating a patient suffering from a HCV infection with the compounds and/or compositions of the present invention is selected in accordance with a variety of factors, including the age, weight, sex, diet, and medical condition of the patient, the severity of the infection, the route of administration, pharmacological considerations such as the activity, efficacy, pharmacokinetic, and toxicology profiles of the particular compounds employed, and whether a drug delivery system is utilized. Administration of the drug combinations disclosed herein should generally be continued over a period of several weeks to several months or years until virus titers reach acceptable levels, indicating that infection has been controlled or eradicated. Patients undergoing treatment with the drug combinations disclosed herein can be routinely monitored by measuring hepatitis viral RNA in patients' serum by slot-blot, dot-blot, or RT-PCR techniques, or by measurement of hepatitis C viral antigens, such as surface antigens, in serum to determine the effectiveness of therapy. Continuous analysis of the data obtained by these methods permits modification of the treatment regimen during therapy so that optimal amounts of each component in the combination are administered, and so that the duration of treatment can be determined as well. Thus, the treatment regimen/dosing schedule can be rationally modified over the course of therapy so that the lowest amounts of each of the antiviral compounds used in combination which together exhibit satisfactory anti-hepatitis C virus effectiveness are administered, and so that administration of such antiviral compounds in combination is continued only so long as is necessary to successfully treat the infection.

The present invention encompasses the use of the HCV serine protease inhibitors disclosed herein in various combinations with the foregoing and similar types of compounds having anti-HCV activity to treat or prevent HCV infections in patients, particularly those patients that have HCV infections that have developed resistance to treatment by VX-950 and other standard protease inhibitors. For example, one or more HCV serine protease inhibitors can be used in combination with: one or more interferons or interferon derivatives having anti-HCV activity; one or more non-interferon compounds having anti-HCV activity; or one or more interferons or interferon derivatives having anti-HCV activity and one or more non-interferon compounds having anti-HCV activity. When used in combination to treat or prevent HCV infection in a human patient, any of the presently disclosed HCV serine protease inhibitors and foregoing compounds having anti-HCV activity can be present in a pharmaceutically or anti-HCV effective amount. By virtue of their additive or synergistic effects, when used in the combinations described above, each can also be present in a subclinical pharmaceutically effective or anti-HCV effective amount, i.e., an amount that, if used alone, provides reduced pharmaceutical effectiveness in completely inhibiting or reducing the accumulation of HCV virions and/or reducing or ameliorating conditions or symptoms associated with HCV infection or pathogenesis in patients compared to such HCV serine protease inhibitors and compounds having anti-HCV activity when used in pharmaceutically effective amounts. In addition, the present invention encompasses the use of combinations of HCV serine protease inhibitors and compounds having anti-HCV activity as described above to treat or prevent HCV infections, where one or more of these inhibitors or compounds is present in a pharmaceutically effective amount, and the other(s) is(are) present in a subclinical pharmaceutically-effective or anti-HCV effective amount(s) owing to their additive or synergistic effects. As used herein, the term "additive effect" describes the combined effect of two (or more) pharmaceutically active agents that is equal to the sum of the effect of each agent given alone. A "synergistic effect" is one in which the combined effect of two (or more) pharmaceutically active agents is greater than the sum of the effect of each agent given alone.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence of disease symptoms.

A specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of active ingredients will also depend upon the particular described compound and the presence or absence and the nature of the additional anti-viral agent in the composition.

Accordingly, the agents of the present application useful for therapeutic treatment can be administered alone, in a composition with a suitable pharmaceutical carrier, or in combination with other therapeutic agents. An effective amount of the agents to be administered can be determined on a case-by-case basis. Factors to be considered usually include age, body weight, stage of the condition, other disease conditions, duration of the treatment, and the response to the initial treatment. Typically, the agents are prepared as an injectable, either as a liquid solution or suspension. However, solid forms suitable for solution in, or suspension in, liquid vehicles prior to injection can also be prepared. The agent can also be formulated into an enteric-coated tablet or gel capsule according to known methods in the art. The agents of the present application may be administered in any way which is medically acceptable which may depend on the identity of the agent and/or on the disease condition or injury being treated. Possible administration routes include injections, by parenteral routes such as intravascular, intravenous, intraepidural or others, as well as oral, nasal, ophthalmic, rectal, topical, or pulmonary, e.g., by inhalation, aerosolization or nebulization. The agents may also be directly applied to tissue surfaces, e.g., during surgery. Sustained release administration is also specifically included in the application, by such means as depot injections, transdermal patches, or erodible implants.

According to another embodiment, the invention provides a method for treating a patient infected with or preventing infection by a virus characterized by a virally encoded serine protease that is necessary for the life cycle of the virus by administering to said patient a pharmaceutically acceptable composition of this invention. Preferably, the methods of this invention are used to treat a patient suffering from a HCV infection. Such treatment may completely eradicate the viral infection or reduce the severity thereof. More preferably, the patient is a human being.

The term "treating" includes prophylactic (e.g., preventing) and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

In an alternate embodiment, the methods of this invention additionally comprise the step of administering to said patient an anti-viral agent preferably an anti-HCV agent. Such antiviral agents include, but are not limited to, immunomodulatory agents, such as alpha-, beta-, and gamma-interferons, pegylated derivatized interferon-alpha compounds, and thymosin; other anti-viral agents, such as ribavirin and amantadine; other inhibitors of hepatitis C proteases (NS2-NS3 inhibitors and NS3-NS4A inhibitors); inhibitors of other targets in the HCV life cycle, including helicase and polymerase inhibitors; inhibitors of internal ribosome entry; broad-spectrum viral inhibitors, such as XIPDH inhibitors (e.g., VX497 and other IMPDH inhibitors disclosed in U.S. Pat. No. 5,807,876, mycophenolic acid and derivatives thereof); or combinations of any of the above.

Such additional agent may be administered to said patient as part of a single dosage form comprising both a compound of this invention and an additional anti-viral agent. Alternatively the additional agent may be administered separately from the compound of this invention, as part of a multiple dosage form, wherein said additional agent is administered prior to, together with or following a composition comprising a compound of this invention.

In yet another embodiment the present invention provides a method of pre-treating a biological substance intended for administration to a patient comprising the step of contacting said biological substance with a pharmaceutically acceptable composition comprising a compound of this invention. Such biological substances include, but are not limited to, blood and components thereof such as plasma, platelets, subpopulations of blood cells and the like; organs such as kidney, liver, heart, lung, etc; sperm and ova; bone marrow and components thereof, and other fluids to be infused into a patient such as saline, dextrose, etc.

According to another embodiment the invention provides methods of treating materials that may potentially come into contact with a virus characterized by a virally encoded serine protease necessary for its life cycle. This method comprises the step of contacting said material with a compound according to the invention. Such materials include, but are not limited to, surgical instruments and garments; laboratory instruments and garments; blood collection apparatuses and materials; and invasive devices, such as shunts, stents, etc.

In another embodiment, the compounds of this invention may be used as laboratory tools to aid in the isolation of a virally encoded serine protease. This method comprises the steps of providing a compound of this invention attached to a solid support; contacting said solid support with a sample containing a viral serine protease under conditions that cause said protease to bind to said solid support; and eluting said serine protease from said solid support. Preferably, the viral serine protease isolated by this method is HCV NS3 protease. More particularly, it is a mutant HCV NS3 protease that is resistant to treatment by VX-905 and/or BILN 2061 as described herein. Exemplary such proteases includes those described herein as having mutant (i.e., non-wild-type) residues at positions 36, 41, 43, 54, 148, 155, and/or 156 of a protein of SEQ ID NO:2.

EXEMPLIFICATION

The disclosure now being generally described, it will be more readily understood by reference to the following examples, which are included merely for purposes of illustration of certain aspects and embodiments of the present disclosure, and are not intended to limit the disclosure.

Example 1

Patient Population and Study Design

Thirty four patients infected with genotype 1 HCV who were enrolled in a phase 1b randomized, blinded, dose-escalation clinical trial for VX-950 (Study VX04-950-101) were subjects of the study. All patients were between 18 and 65 years of age, had baseline HCV RNA levels of at least $10^5$ IU/mL, and were hepatitis B virus (HBV) and HIV negative. Patients were divided into 3 groups receiving 450 (q8h), 750 (q8h), or 1250 (q12h) mg VX-950 for 14 consecutive days, with 2 placebo patients in each dosing group. Four milliliter (mL) blood samples were collected from study patients at 3 time points: the day before dosing (baseline samples), at day 14 of dosing or end of treatment (ETR sample), and 7 to 10 days after the last dose of study drug (follow-up sample). Blood was collected by venipuncture of a forearm vein into tubes containing EDTA ($K_2$) anticoagulant. Plasma was separated by 10 min centrifugation, frozen, and stored at −80° C. for less than 6 months. Virions were isolated from this plasma for sequence analysis.

Example 2

Amplification and Sequencing of the HCVNS3 Protease from Patient Plasma

Sequence analysis of HCV was done by semi-nested reverse-transcriptase polymerase chain reaction (RT-PCR) amplification of a HCV RNA fragment containing the full 534 base pair (bp) NS3 serine protease region from plasma virus. The virions were lysed under denaturing conditions, and the HCV RNA was isolated using a standard commercial silica-gel membrane—binding method (QIAamp Viral RNA Minikit; Qiagen, Valencia, CA). A complementary DNA (cDNA) fragment containing the NS3 serine protease region was synthesized from viral RNA and amplified using a commercial 1-step reverse transcriptase PCR (Superscript III RNase H-Reverse Transcriptase with High Fidelity Platinum Taq DNA Polymerase; Invitrogen Corp, Carlsbad, CA). A 912 bp coding region of N53 was amplified using primers flanking the NS3 region (NS3-1b-1s: GGCGTGTGGGGA-CATCATC (SEQ ID NO: 3); and NS3-1b-3a: GGTGGAG-TACGTGATGGGGC (SEQ ID NO: 4)). Two rounds of nest PCR were performed for each sample at a final concentration of 0.5 µM primer (Invitrogen Custom Primers), 0.2 mM dNTPs (Invitrogen Corp), 1.2 mM MgSO4, and 34.8 units of RNA guard (Porcine RNase Inhibitor, Amersham Biosciences) in 1x proprietary reaction buffer. Reaction mixtures were initially incubated for a 30 min reverse transcription reaction at 47 □C followed by a 3 min denaturation step at 94° C. and then 30 cycles of 94° C. for 30 sec, 51° C. for 30 sec, and 68° C. for 45 sec. The first PCR product was diluted 1:10 and used in another semi-nested reaction using 1.25 units of AccuPrime Pfx DNA polymerase, 0.5 µmM primer (NS3-1b-1s and NS3-1b-4a; CATATACGCTCCAAAGCCCA (SEQ ID NO: 5)), 0.3 mM dNTPs, 1 mM MgSO4, and 1x reaction buffer. The DNA products from the outer PCR were denatured for 3 min at 94° C. and amplified with 30 cycles of 94° C. for 30s, 53° C. for 30s, and 68° C. for 30s. The DNA from this PCR was then separated on a 1% agarose gel, and the appropriately sized product (830 bp) was purified using the QIAquick Gel Extraction Kit (Qiagen). Isolated DNA was then cloned using the Zero Blunt TOPO PCR Cloning Kit (Invitrogen Corp). Cloning plates were sent to Seq Wright (Houston, TX) where 96 clones were amplified and sequenced per patient per time point.

Example 3

Sequence Alignment and Phylogenetic Analysis

Sequences were aligned and analyzed for mutations using the software Mutational Surveyor (SoftGenetics, State College, Pa.). The N-terminal 543 nucleotides (181 amino acids) of NS3 protease were analyzed. A consensus sequence for each patient was developed from an average of 84 baseline sequences, and an average of 81 sequences were obtained for each patient at Day 14 and at follow-up (7 to 10 days after the last dose of study drug). Phylogenetic trees were made using PHYLIP (Felsenstein, J. 1993. PHYLIP (Phylogeny Inference Package) version 3.5c. Distributed by the author. Department of Genetics, University of Washington, Seattle, Wash.) Dnadist and Quick Tree.

Example 4

Expression and Purification of Recombinant NS3 Protease Proteins

A DNA fragment encoding $Met^1$-Ser181 of the HCV NS3 protease was amplified from selected plasmid clones of patient isolates using oligonucleotides specific for each HCV variant. The DNA fragment was cloned into the *Escherichia coli* expression plasmid pBEV11 leading to a 181-residue HCV NS3 protease domain followed by a C-terminal hexahistidine tag (SEQ ID NO: 6). Recombinant 6X His-tagged (SEQ ID NO: 6) NS3 proteases were then expressed in *E. coli* using a leaky expression method as previously published (4). Five to seven isolated colonies of *E. coli* BL21 (DE3) freshly transformed with the NS3 protease expression plasmids were used to inoculate a 5 mL LB medium with 100 µg/mL carbenicillin. These seed cultures were incubated at 37° C. with shaking (250 rpm) until reaching an OD620 between 0.3 and 1, then used to inoculate 50 mL 4×TY broth (32 g/L tryptone, 20 g/L, yeast extract, 5 g/L NaCl) containing 100 µg/mL carbenicillin in 250 mL Erlenmeyer flasks at an initial OD620 of ~0.010. The expression cultures were incubated for 24 hours at ambient temperature (~25° C.) with shaking at 250 rpm. The cells were harvested by centrifugation at 3000× g for 30 min, the pellets were rapidly frozen in an −80° C. ethanol bath and stored at −80° C. until the protease was purified.

Recombinant proteases were purified from *E. coli* using a modification of a published method (7). Frozen cell pellets were thawed and re-suspended in 6.8 mL of cold Buffer A (50 mM N-2-Hydroxyethyl piperizine-N'-ethanesulfonic acid [HEPES, pH 8.0]; 1 M NaCl; 10% [vol/vol] glycerol; 5 mM imidazole; 5 mM β-mercaptoethanol; 0.1% Octyl β-D-glucopyranoside [Sigma, Saint Louis, Mo.]; 2 µg/mL Leupeptin [Sigma, Saint Louis, Mo.]; 1 µg/mL E-64 [Sigma, Saint Louis, Mo.]; 2 µg/mL Pepstatin A [Sigma, Saint Louis, Mo.]). The cells were lysed by the addition of 0.8 mL 10× BugBuster reagent (Novogen/EMD Biosciences, Madison, Wis.) and 8 µL of 1000× Benzonuclease (Novogen/EMD Biosciences, Madison, Wis.) followed by gentle rocking at 4° C. for 30 min. Cell lysates were centrifuged at 16,000×g to remove insoluble material. Each supernatant was applied to a 0.25 mL bed volume of TALON metal affinity resin (BD Biosciences, Palo Alto, Calif.) equilibrated to Buffer A in disposable polypropylene columns (Biorad, Hercules, Calif.). The lysate/resin slurries were rocked at 4° C. for 30 min. The lysates were drained from the column and the resin washed with 3-5 mL volumes of Buffer A. Two aliquots (0.25 mL each) of Buffer B (50 mM HEPES [pH 8.0]; 1 M NaCl; 25% [vol/vol] glycerol; 300 mM imidazole; 5 mM β-mercaptoethanol; 0.1% Octyl β-D-glucopyranoside; 2 µg/mL Leupeptin; 1 µg/mL E-64; 2 µg/mL Pepstatin A]) were used to elute protein bound to the column, the two fractions were pooled, divided into small aliquots and stored at −80° C. The concentration of the eluted protein was determined using a Coomassie protein assay (Biorad, Hercules, Calif.) according to the manufacturers instructions with a bovine serum albumin standard. Purity of the protease was estimated using 1D Image Analysis Software (Kodak, Rochester, N.Y.) from protein samples resolved on denaturing acrylamide gels (SDS-PAGE) stained with Biosafe Coomassie Blue (Biorad, Hercules, Calif.).

Example 5

Enzymatic Assay for the HCV NS3 Serine Protease Domain

In vitro protease activity was assayed as published (7) in 96-well microtiter plates (Corning NBS 3990) with both VX-950 and BILN 2061 protease inhibitors. BILN 2061 is a HCV NS3•4A protease inhibitor discovered by Boehringher Ingelheim, Laval, Quebec, Canada. Briefly, protease was incubated with 5 µM co-factor KK4A at 25° C. for 10 min and at 30° C. for 10 min. Protease inhibitor (VX-950 or BILN 2061), serially diluted in DMSO, was added and incubated for an additional 15 min at 30° C. The reaction was initiated by the addition of 5 µM RET-S1 (Anaspec Inc. San Jose, Calif.), an internally quenched fluorogenic depsipeptide substrate, and incubated at 30° C. Product release was monitored for 20 min (excitation at 360 nm and emission at 500 nm) in a Tecan SpectraFluorPlus plate reader. Data were fitted with a simple $IC_{50}$ equation: $Y=V_0/(1+(X/IC_{50}))$.

Example 6

$K_m$ Determination of HCV NS3 Serine Protease Domain Proteins

Substrate kinetic parameters were determined with an internally quenched fluorogenic depsipeptide substrate, RET-S1 (Ac-DED(EDANS)EEαAbuψ[COO]ASK (DABCYL)-NH2) (Taliani et al., (1996) Anal. Biochem. 240(1), 60-67). Protease was pre-incubated with 5 µM co-factor peptide KK4A (KKGSVVIVGRIVLSGK) (SEQ ID NO: 8)) (Landro et al., (1997) Biochemistry 36(31), 9340-9348) in 50 mM HEPES (pH 7.8), 100 mM NaCl, 20% glycerol, 5 mM dithiothreitol at 25° C. for 10 min and at 30° C. for 10 min. The reaction was initiated by the addition of the RET-S1 substrate (Anaspec Incorporated, San Jose, Calif.) and incubated for 10 min at 30° C. Total assay volume was 100 µL. The reaction was quenched by the addition of 25 µL 10% trifluoroacetic acid (TFA). Reaction products were separated on a reverse phase microbore high performance liquid chromatography column (Penomenex Jupiter 5µ C18 300 A column, 150×2.0 mm), which was heated to 40° C. The flow rate was 0.2 ml/min, with H2O/0.1% TFA (solvent A) and acetonitrile/0.1% TFA (solvent B). A linear gradient was used as follows: 5% to 30% solvent B over 1 min, 30% to 40% solvent B over 15 min, then 40% to 100% solvent B over 1 min, 3 min isocratic, followed by 100% to 5% B in 1 min, and equilibration at 5% B for 10 min. The DABCYL-peptide product was detected at 500 nm and typically eluted around 17 min. $K_m$ was determined by fitting the data to the Michaelis-Menten equation with GraphPrism software.

Example 7

Determination of Telaprevir (VX-950) $K_{i(app,\,1\,h)}$ of the HCV NS3 Serine Protease Domain Variants Sensitivity of the NS3 protease domain variants to telaprevir was determined in 96-well microtiter plates (Corning NBS 3990; Corning, N.Y.) as published previously (Lin et al., (2004) J. Biol. Chem. 279(17), 17508-17514). Briefly, the NS3 protease domain was pre-incubated with 5 µM KK4A peptide in 50 mM HEPES (pH 7.8), 100 mM NaCl, 20% glycerol, 5 mM dithiothreitol at 25° C. for 10 min and at 30° C. for 10 min. Telaprevir, serially diluted in DMSO, was added to the protease mixture and incubated for an additional 60 min at 30° C. The reaction was started by the addition of 5 µM RET-S1 substrate and incubated at 30° C. Product release was monitored for 20 min (excitation at 360 nm and emission at 500 nm) in a Tecan SpectraFluorPlus plate reader (Tecan US, Durham, N.C.). Total assay volume was 100 µl. Protease concentration was chosen such that 10-20% of the substrate was turned over during the course of the assay. To calculate apparent inhibition constant ($K_{i(app,\,1\,h)}$) values, data were fit to the integrated form of Morrison's equation for tight binding inhibition (38) using the GraphPrism software. Steady-state assays showed that the wild type enzyme and all R155K/T/I/S variants had a $K_m$ for RET-S1 that was higher than the limit of detection (100 µM). Thus, the $K_m$ was set to 100 µM for calculating $K_{i(app,\,1\,h)}$ values. Inhibitor studies were carried out at a substrate concentration (5 µM) that is significantly below the $K_m$. Therefore, the deviation between the true $K_m$ and the $K_m$ used in calculations should have a negligible effect in the calculation of $K_{i(app,1h)}$.

Example 8

Sequence Analysis of Baseline Samples

The consensus sequence for each patient's HCV population was derived from an average of 84 independent plasmid clones containing HCV cDNA. Phylogenetic analysis of the consensus sequences indicated that sequences were patient specific (FIG. 1). The average intra-patient amino acid quasispecies complexity (Shannon entropy) and diversity (Hamming distance) were low (0.332±0.109 and 0.421±0.195, respectively), and no correlation of quasispecies heterogeneity with HCV RNA plasma concentration at baseline was observed. The inter-patient amino acid diversity (individual consensus compared to genotype 1a or 1b consensus sequence of the patients in this trial) was 1.3% for genotype 1a and 2% for genotype 1b. Structural modeling analysis predicted that amino acid differences observed between consensus sequences of all patients within a subtype would have little or no impact on VX-950 binding.

Patient-specific protease clones were then expressed and tested for inhibition by VX-950. In agreement with the modeling observation, there were no significant differences in the enzymatic $IC_{50}$ values of these proteases derived from different patient isolates within a specific subtype. However, the average $IC_{50}$ for genotype 1b patients was slightly higher than for genotype 1a patients (FIG. 2). This finding is consistent with previous in vitro results measuring the $K_i$ value for HCV-H (1a) and HCV Con1 (1b) (7). Modeling analysis of 1a versus 1b genotypes suggested that the key difference that may affect the inhibitor/substrate binding is at the residue position 132, whereas other differences are located outside the binding pocket. The Val$^{132}$ side-chain of the genotype 1b protease makes only one van der Waals contact with the P3 terbutyl-glycine group of VX-950, while the Ile$^{132}$ side-chain of the genotype 1a protease makes 2 contacts. This structural difference in interactions is consistent with the experimental data that shows a lower enzyme IC$_{50}$ of VX-950 with the genotype 1a proteases compared to the genotype 1b proteases. Although there is a slight difference between subtypes, both subtypes are still clearly sensitive to VX-950. In conclusion, despite the observed sequence diversity in the HCV NS3 serine protease, genotype 1 patients are expected to be responsive to treatment with the protease inhibitor VX-950. The clinical data supports this finding as no significant difference in viral response to VX-950 was observed.

Example 9

Genotypic Data: Sequence Analysis of ETR and Follow-up Samples

The HCV NS3 protease sequences at end of treatment (ETR) were compared to the consensus sequences at baseline for each patient to identify potential resistance mutations. An average of 80 sequences was obtained for each ETR sample, and the percent of variants at each of 181 positions was calculated. Initially, an increase in frequency of 5% or greater at any single amino acid position of the ETR sample compared to the baseline was considered to be a potential resistance mutation. The 5% cut off value was used because this was the lower level of sensitivity of our sequencing protocol, based on the number of clones analyzed and the error rate of the PCR. Changes at sites that were polymorphic at baseline were not considered resistance mutations. Changes at sites which were only present at end of dosing and that were observed in multiple patients were considered potential resistance mutations and these were then analyzed in all the patients.

For analysis, patients were split into groups based on viral load (plasma HCV RNA levels) response to VX-950. Patients were grouped into "initial responders" or "continued responders" in the viral dynamic analysis. In viral sequence analysis, the "initial responder" group was further divided into two groups based on the increase in plasma HCV RNA after the initial decline. Patients who had less than a 0.75 log$_{10}$ increase from the lowest measured HCV RNA level to end of dosing (Day 14) were categorized as patients with an HCV RNA "plateau". Those who had greater than a 0.75 log$_{10}$ increase in plasma HCV RNA were categorized as patients with HCV RNA "rebound". Normal fluctuation in HCV RNA in an untreated patient is about 0.5 log$_{10}$, and these groupings were based on antiviral response as well as viral mutational pattern. There were 2 patients for whom these categories were inconsistent between the 2 types of analyses. Patient 12308 had an increase of 0.05 log$_{10}$ from nadir to end of dosing (Day 14) and was categorized as "plateau" for the sequence analysis, while for the viral dynamic analysis 12308 was placed in the "continued responders" group. Patient 3112 had undetectable plasma HCV RNA (<10 IU/ml) at Day 11, but detectable plasma HCV RNA of 35 IU/ml at end of dosing (Day 14).

This increase in HCV RNA caused the patient to be placed in "initial responders" group for viral dynamic analysis; however, in the sequence analysis the level of HCV RNA remained undetectable by the sequencing assay and the patient was therefore grouped into the "continued responders" group.

Sequence analysis grouped patients by: no response (placebo); decline followed by rebound during dosing (rebound); decline followed by plateau during dosing (plateau); and continued decline throughout dosing (continued responders) (FIG. 3). Additionally, within these groups, patients were analyzed by dose group and genotype subgroup (1a or 1b). Lastly, mutations were analyzed in follow-up samples collected 7 to 10 days after withdrawal of VX-950 to monitor the persistence of any mutations as well as any shift from baseline variants. An average of 81 clones were analyzed for each follow-up sample. Complete sequence analysis is available for 28 of the patients, and analysis of the remaining 6 patients is currently in progress. Analysis is ongoing for 2 patients with rebound, 3 with plateau, and 1 with continued decline. In the first group of placebo patients (n=6), there were no significant changes from baseline at any position in any patient.

Example 10

Patients with HCV RNA Rebound During Dosing

There were 13 patients who initially responded to VX-950 with a greater than 2 log$_{10}$ drop in HCV RNA, but eventually began to rebound while still being dosed with VX-950. Of these 13 patients, 6 were in the 450 mg q8h dose group, 1 was in the 750 mg q8h dose group, and 6 were in the 1250 mg q12h dose group. Complete sequence analysis is available for 11 of these patients at Day 14 (Table 1). All of these patients had a significant increase in mutations at position 36. At position 36, the wild-type valine was mutated to an alanine (V36A) in genotype 1b patients (mean 60%, range 31%-86%) and to either an alanine or a methionine (V36M) in genotype 1a patients (mean 62%, range 18%-90%). The absence of V36M in subtype 1b is likely due to the requirement of 2 nucleotide substitutions in subtype 1b versus only a single change in subtype 1a. The V36A mutation requires a single nucleotide change in either subtype 1a or 1b. Mutation to glycine at position 36 (V36G) was also seen in genotype 1b patients and to a leucine (V36L) in 1a patients, but at a much lower frequency. Three patients also had a mutation at position 54 from a threonine to an alanine (T54A) (mean 35%, range 8%-67%) and less frequently to a serine (T54S). Interestingly, the mutations at positions 36 and 54 appear to be mutually exclusive. Additionally, all patients in this group who were genotype 1a contained a mutation at position 155 from an arginine to either lysine (R155K) or threonine (R155T) (mean 60%, range 22%-99%), and less frequently to isoleucine (R155I), serine (R155S), methionine (R155M), or glycine (R155G). The observation that these mutations at R155 is restricted to subtype 1a patients is again likely due to the requirement for 2 nucleotide changes from baseline in the 1b patients versus a single nucleotide change in 1a patients. In follow-up samples from this group, wild-type virus began to re-emerge, but all mutations seen at ETR were still present, although at different frequencies potentially due to differences in viral fitness. No sequencing samples are available for the time point at which rebound was first observed for each patient, so it is not clear if other mutations were present earlier.

Example 11

Patients with Plateaued HCV RNA Response During Dosing

In the next group (n=8), patients responded to VX-950 initially, but their HCV RNA response stabilized and did not continue to decline, although no increase in HCV RNA was seen. Two of these patients were in the 450 mg q8h dose group, 2 were in the 750 mg q8h dose group, and 4 were in the 1250 mg q12h dose group. Analysis is complete for 5 of these patients at Day 14 (Table 1). All patients developed a mutation at position 156 from an alanine to either valine (A156V) or threonine (A156T), and very infrequently to a serine (A156S) or isoleucine (A156I). The A156V/T mutation was seen at a very high frequency in 3 of the patients in this group (100%), and no other mutation was seen in these patients. The other 2 patients (02104 and 12308) only had 8% A156T and 30% A156V mutant virus, respectively, but these patients also had mutations at other positions (47% V36A/M and 36% R155K/T for patient 02104; 68% T54A for patient 12308). One patient from the rebound group, 02102, also had a similar frequency of mutations (11%) at position 156. At follow-up time points, the mutation at position 156 was almost completely replaced by either wild-type virus or virus with mutations at positions 36, 54, and/or 155. A change to serine at position 156 (A156S) was the dominant mutation seen during in vitro resistance studies of VX-950 (7). The A156V/T mutations were also identified as cross-resistant to both VX-950 and BILN 2061 in an in vitro study (7).

Example 12

Patients with Continued Response During Dosing

The remaining 7 patients responded to VX-950 with a continuous decline in HCV RNA levels throughout the 14-day dosing period. Five of these patients were in the 750 mg q8h dose group and 2 were in the 450 mg q8h dose group. These patients had very low levels of HCV RNA at Day 14 (64 IU/mL to undetectable (<10 IU/mL)), and sequencing data could not be obtained at this time point. However, HCV cDNA was successfully amplified from the follow-up samples for these patients, and analysis is complete for 6 of these 7 patients (Table 1). The genotype 1a patient (03205) who had reached undetectable levels by Day 14 had 3 mutations, V36A/M (67%), T54A (11%), and R155K/T (26%), at the follow-up time point. Two genotype 1b patients had the V36A (21% and 25%) and T54A mutations (54% and 20%), and another two 1b patients had only low levels of the V36A (3% and 9%) and the T54A (6% and 1%) mutations at follow up. In the last 1b patient who had undetectable HCV RNA levels at Day 14 (<10 IU/mL), no mutations were detected at follow up.

Example 13

Frequency of Double Mutations

Frequency of double mutations that were found in patients were also analyzed. The mutations at position 36 were found in combination with mutations at both positions 155 (36/155 double mutation) and 156 (36/156 double mutation). Only genotype 1a patients had the 36/155 double mutation, which was seen in all eight 1a patients analyzed in the rebound group (mean 27.6%, range 10%-77%) and in one of two 1a patients in the plateau group (9%) at Day 14 ETR. The 36/156 double mutation was much less frequent, and found in 3 patients in the rebound group (3%, range 1%-5%) and in 2 patients in the plateau group (1% and 4%) at Day 14 ETR. Double mutations were also found in the follow-up samples at a similar frequency for 36/155 but at a lower frequency for 36/156 as compared with the ETR samples. For the group of patients that continued to decline, only 1 patient had the 36/155 double mutation, which was present at 5%.

The frequency of mutations found either alone or in combination is shown in FIG. 4. A summary of the resistance patterns is shown in FIG. 5, which depicts the average percent of mutated amino acids for each patient group.

Example 14

Phenotypic Data: Enzymatic $IC_{50}$ Analysis of Resistance Mutations

Since an average of 82 independent sequencing clones were subjected to genotypic analysis, there was a mixture of virions in each patient, as shown in Table 1. The enzyme $IC_{50}$ of all mutants seen in the above sequence analysis (V36A/M/G, T54A/S, R155K/T/M/G/S, and A156T/V/S) as well as any observed combinations of these mutations found in vivo were determined in at least 2 different patient-specific genetic backgrounds. The baseline $IC_{50}$ for all patients within a genotype were similar, as reported in Example 6. Enzyme $IC_{50}$ values of resistant proteases are reported as fold change compared to the genotype 1a HCV-H reference strain. The $IC_{50}$ of this reference strain was found to be 64 nM in this enzyme assay.

FIG. 5 shows the enzyme $IC_{50}$ values and the fold change over the reference strain for single mutants. The values that are similar for any amino acid change at a given position are grouped together in boxes in this figure. A single mutation at position 36 confers low levels of resistance to VX-950. The V36A/M/L mutations show about a 1.5- to 10-fold increase in enzyme $IC_{50}$, regardless of the specific amino acid change. The substitution at position 54 from a threonine to a serine (T54S) does not significantly increase $IC_{50}$. However the T54A mutation gives about a 10-fold increase in enzyme $IC_{50}$. The substitution at position 155 also confers fairly low levels of resistance (about a 5- to 15-fold increase in $IC_{50}$), for any of the changes from an arginine to a threonine (R155T), lysine (R155K), methionine (R155M), or serine (R155S). The mutation at position 156 from an alanine to a valine (A156V), threonine (A156T), or isoleucine (A156I) confers high levels of resistance (about a 400- to 500-fold increase in enzyme $IC_{50}$). Interestingly, the A156S mutation is much less resistant to VX-950 (only a 22-fold increase in $IC_{50}$) than the other amino acid changes at this position, which is consistent with the in vitro resistance studies (6, 7).

FIG. 6 shows the actual enzyme $IC_{50}$ values as well as the fold change over the reference strain for double mutants. Double mutations at these positions give higher levels of resistance than any single mutation. A mutation at position 36 combined with either a mutation at position 155 or 156 gives about an additional 10-fold increase in resistance over the respective single mutants. Table 2 lists the actual $IC_{50}$ values for all mutants tested against both VX-950 as well as another HCV protease inhibitor, BILN 2061. The mutations at positions 36 and 54 affect susceptibility to VX-950 much more than BILN 2061, whereas the mutation at residue 155 confers much higher levels of resistance to BILN 2061. The mutations at position 156 as well as the double mutations all confer high levels of resistance against both inhibitors. However, the A156S mutant is more resistant to VX-950, which has been shown previously in vitro (7). Table 3 shows the mean and standard deviation values of the enzyme $IC_{50}$ and fold change over the reference strain of all mutations at a given position.

Example 15

Average Phenotypes for Each Patient

The genotypic analyses performed here allowed a detailed examination of the relative proportion of different resistant mutants within each patient. To better understand the level of phenotypic resistance conferred by these viral mixtures, exploratory analyses were done to obtain an average phenotype for each patient. The percent of virions with a given single or double mutation was multiplied by the average fold change in enzyme $IC_{50}$ for that given mutant (Table 3), and then all values were added for each patient. The relative number (value divided by 100) is shown in the last column of Table 1. The mean value for the rebound group of patients was 27 at Day 14 (range 6-70) and 15 at follow-up (range 3-29). The mean value for the plateau group of patients was 272 at Day 14 (range 26-466) and 32 at follow-up (range 1-126). The last group of patients that continued to decline had a mean value of 4 at follow-up (range 0-10). From these very preliminary calculations, it seems that the level of resistance in all groups of-patients declines after the last dose (from Day 14 to follow-up), which is not unexpected, as the drug pressure is no longer present for selection of resistant virions. It also appears that the rebound group of patients has lower levels of resistance than the patients that plateaued. An analysis correlating pharmacokinetic data with resistance patterns is currently underway.

Example 16

Fitness Analysis of Resistance Mutations

Another important aspect of these viral variants in addition to their resistance profile is the level of fitness. The viral fitness of single and double mutants was calculated (Table 4). The absolute number of infectious units (IU/mL) of each HCV variant in an individual patient at a given time point was determined. For example, the absolute number of infectious units of variants with the A156V/T mutation in Patient 03201 at Day 14 was calculated as: $VL_{d14\ (A156V/T,\ 3201)} = VL_{d14\ (whole,\ 3201)} \times \%\ A156V/T_{d14\ (3201)}$. Total HCV RNA at either end-of-dosing (Day 14, $VL_{d14\ (whole,\ 3201)}$) or follow-up (Day 21, $VL_{d21\ (whole,\ 3201)}$) was taken from the analysis of plasma HCV RNA levels, as determined by the Roche COBAS Taqman HCV assay. Undetectable levels of HCV RNA were considered to be 5 IU/mL. The percentage of each individual variant group (e.g., A156V/T) at either end-of-dosing (Day 14, $\%\ A156V/T_{d14\ (3201)}$) or follow-up (Day 21, $\%\ A156V/T_{d21\ (3201)}$) was taken from the sequence analysis described above (Table 1). Next, the fold of net increase in plasma HCV viral load (NVL) for each HCV variant and the whole population of HCV in the plasma in the individual patient after dosing (Day 14 to Day 21) was determined. For example:

$$NVL_{(A156V/T,\ 3201)} = VL_{d21\ (A156V/T,\ 3201)} / VL_{d14\ (A156V/T,\ 3201)}$$

$$NVL_{(whole,\ 3201)} = VL_{d21\ (whole,\ 3201)} / VL_{d14\ (whole,\ 3201)}$$

The NVL of each HCV variant was normalized to that of the whole plasma HCV population in each patient: $\%\ NVL_{(A156V/T,\ 3201)} = NVL_{(A156V/T,\ 3201)} / NVL_{(whole,\ 3201)}$.

The normalized fold of net increase in viral load of each HCV variant in individual patients were then converted into $\log_{10}$-converted values: $Log_{10}[\%\ NVL_{(A156V/T,\ 3201)}]$, and the average value for a variant was determined from all patients. The fitness of the HCV mutant was then calculated: Fitness for A156V/T mutation$=10_{Log(fitness,\ A156V/T)}$. This relative fitness score was analyzed with the resistance level of each mutant. As shown in FIG. 7, all mutants were less fit than wild-type and, in general, using this analysis there is an inverse correlation between fitness and resistance of single mutants. The double mutant 36/155, however, has a significant increase in resistance with less impact on fitness. This may be due to interaction of the mutations compensating for the loss of fitness, while still conferring resistance.

Example 17

X-ray Structure of the R155K Variant Protease

Purified R155K variant of the HCV-H strain protease domain, in a complex with an NS4A peptide co-factor (Kim et al., (1996) Cell 87(2), 343-355), at a concentration of 8.0 mg/ml was used for crystallization trials. The protein crystals were grown over a reservoir liquid of 0.1 M MES (pH 6.2), 1.4 M NaCl, 0.3 M $KH_2PO4$, and 10 mM β-mercaptoethanol. Single crystals were obtained in the hanging droplets after equilibrating over two days. A single crystal with dimensions of 0.15×0.15×0.35 mm was transferred into cryo-protectant solution of mother liquid with 25% glycerol added shortly prior to be flush-cooled to 100K in nitrogen gas stream. The diffraction images were collected using a CCD4 image plate instrument mounted on an ALS beam line 5,01. Data at 2.5-Å resolution was indexed and integrated using HKL (2000, HKL Incorporated, Charlottesville, Va.) and CCP4 software. The crystals belong to space group R32 with unit cell dimensions of a=225.31 Å, b=225.31 Å, c=75.66 Å, α=90.00°, β=90.00° and γ=120.00°. There are 5% of data assigned for testing free R-factor in the later refinements. The crystals of the R155K variant studied here have an identical crystallographic lattice to that of the wild-type protease NS3-4A published previously (Kim et al., supra). The published NS3-4A protease domain (PDB code: 1A1R) was used to perform the initial rigid-body and positional refinement of the model. The difference in the side chains of residue 155 was confirmed to be a Lys instead of Arg in the electron density map. The protein molecule was visually inspected against the electron density map using QUANTA programs. Further inclusion of solvent molecules in the refinement and individual B-factor refinement at a resolution range of 20.0 to 2.5 Å reduced the R-factor and free R-factor to 22.0% and 24.7%, respectively. Residues included in the refined model range from amino acids 1 to 181 of the NS3 protease domain and residues 21 to 39 of the NS4A cofactor for crystallographic independent molecule and two Zn metal ions.

Example 18

Computational Modeling

Telaprevir was modeled into the active site of the R155K variant NS3 protease domain using the X-ray crystal structure of the R155K variant apo-enzyme in a complex with an NS4A cofactor peptide, following the procedure described previously (Lin et al., supra). The ketoamide group of telaprevir was modeled to form a covalent adduct with the Ser$^{139}$ side-chain with a si-face attachment. This binding mode was observed for analogous ketoamide inhibitors (Perni et al., (2004) Bioorg. Med. Chem. Lett. 14(6), 1441-1446) and ketoacid inhibitors (Di Marco et al., (2000) J. Biol. Chem. 275(10), 7152-7157.). The main-chain of the inhibitor was overlaid with the analogous main-chain of these ketoamide and ketoacid inhibitors such that the telaprevir main-chain makes all the following backbone hydrogen bonds: P1 NH with Lys$^{155}$ carbonyl, P3 carbonyl with Ala$^{157}$ NH, P3 NH with Ala$^{157}$ carbonyl, and P4 cap carbonyl with NH of Cys$^{159}$. In this binding mode, the P2 group of telaprevir was placed in the S2 pocket without any need to move the Lys$^{155}$ side-chain. The t-butyl and the cyclohexyl groups of telaprevir were placed in the S3 and S4 pockets, respectively. The inhibitor was energy minimized in two stages. In the first stage, only the inhibitor and the side-chain atoms of Arg$^{123}$, Lys$^{155}$, and Asp$^{168}$ of the protease were allowed to move during energy minimization for 1000 steps. In the second stage, all the side-chain atoms of the protease were allowed to move along with the inhibitor for 1000 additional steps. This modeled structure closely mimics the telaprevir model in the active site of the wild-type NS3 protease described previously (Lin et al., supra). No significant shifts in the positions of Lys$^{155}$ side-chain or the other active residue side-chains were observed. The same procedure was repeated for docking telaprevir into the active site of the R155T variant of the NS3 protease domain. However, the enzyme structure in this case is not the X-ray crystal structure, but a model built using the R155K variant crystal structure. The Lys$^{155}$ residue was replaced with Thr side-chain and was minimized by holding all the atoms of the enzyme fixed except for the Thr$^{155}$ side-chain. In this model, the hydroxyl group of the Thr$^{155}$ side-chain forms a hydrogen bond with the side-chain of Asp$^{81}$. All modeling and minimization procedures were carried out using the QUANTA molecular modeling software (Accelrys Incorporated, San Diego, Calif.).

Example 19

Study Results

Results from enzymatic assays and structural studies are presented here, in addition to the discussions above for certain variants of the invention.

1) Substitutions at Arg$^{155}$ of the NS3 Protease Confer Low-level Resistance to Telaprevir in HCV Replicon Cells To determine whether the observed substitutions of Arg$^{155}$ of the HCV NS3 protease domain are sufficient to confer resistance to telaprevir (VX-950), several substitutions at NS3 residue 155 (R155K, R155T, R155S, R155, R155M, or R155G) were introduced into a high-efficiency subgenomic replicon plasmid (Con1-mADE). Stable HCV replicon cells were generated for each of these variants, indicating that replacement of NS3 Arg$^{155}$ with a different residue did not abolish HCV RNA replication in cells. The average 48-h IC$_{50}$ value of telaprevir in the wild-type HCV replicon Con1-mADE cells was 0.485±0.108 µM, which is slightly higher than what had been determined previously (0.354 µM) in Con1-based HCV replicon cells with a different set of adaptive mutations (24-2) (25,41). Two major Arg$^{155}$ variants, R155K and R155T, which were observed in a phase 1b trial of telaprevir alone, had average 48-h telaprevir IC$_{50}$ values of 3.59±0.28 µM for R155K and 9.60±0.87 µM for R155T. This corresponds to a 7.4- or 20-fold increase, respectively, compared to the wild-type Con1-mADE replicons (Table I). Similar decreases in sensitivity to telaprevir were observed in HCV replicon cells containing the other four minor variants at Arg$^{155}$: R155S, R155I, R155M, or R155G; Table I. These 4 variants were found at much lower frequency than R155K/T in the telaprevir phase 1b trial. The replicon 48-h IC$_{50}$ values for these four variants were 1.97±0.21 µM (R155S), 11.7±2.5 µM (R155I), 2.68±0.21 µM (R155M), and 3.58±0.24 µM (R155G), which corresponds to a 4.1-, 24-, 5.5-, and 7.4-fold, respectively, loss of sensitivity to telaprevir (Table I). These results indicate that substitutions of NS3 Arg$^{155}$ led to low-level (<25-fold) resistance to telaprevir in HCV replicon cells, independent of the physical properties of the substituted residue, which include a positive charged residue (Lys), a hydrophilic residue (Thr or Ser), a hydrophobic residue (Ile or Met), or a residue that lacks a side chain (Gly).

TABLE I

Demonstration of Resistance in HCV Replicon Cell assays

| Variants | Replicon IC$_{50}$ of telaprevir (µM) | Fold change |
| --- | --- | --- |
| Wild-type | 0.485 ± 0.108 | 1.0 ± 0.2 |
| R155K | 3.59 ± 0.28 | 7.4 ± 0.6 |
| R155T | 9.60 ± 0.87 | 20 ± 2 |
| R155S | 1.97 ± 0.21 | 4.1 ± 0.4 |
| R155I | 11.7 ± 2.5 | 24.0 ± 5.2 |
| R155M | 2.68 ± 0.21 | 5.5 ± 0.4 |
| R155G | 3.58 ± 0.24 | 7.4 ± 0.5 |

The stable wild-type (mADE) and variant HCV sub-genomic replicon cell lines were generated using the T7 RNA runoff transcripts from the corresponding high efficiency Con1 replicon plasmids. The average IC$_{50}$ values and SD of telaprevir were determined for the HCV replicon cell lines in the 48-h assay in three independent experiments. Fold change was determined by dividing the IC$_{50}$ of a given variant by that of the wild-type HCV replicon.

2) Substitutions at Arg$^{155}$ of the HCV NS3 Protease Resulted in a Decreased Sensitivity to Telaprevir in Enzyme Assays To confirm whether substitutions at Arg$^{155}$ in the HCV NS3 protease domain are sufficient to cause a loss of sensitivity to telaprevir at the enzyme level, Arg$^{155}$ was replaced with Lys, Thr, Ser, or Ile in an NS3 protease domain (genotype 1a) from which the sequences were derived from HCV samples in a patient prior to dosing with telaprevir. The NS3 serine protease domain proteins containing R155K, R155T, R155S, or R155I mutations were expressed in *E. coli* and purified prior to determination of enzyme sensitivity to telaprevir. Resistance to telaprevir was defined by the fold-change in K$_{i(app,\,1\,h)}$, which is the apparent K$_i$ measured after a 1-h pre-incubation with telaprevir.

A comparison of the sensitivity of telaprevir for the wild-type HCV protease domain co-complexed with the KK4A cofactor peptide versus variants with substitutions at Arg$^{155}$ is shown in Table II. The average K$_{i(app,\,1\,h)}$ value of telaprevir against the wild-type genotype 1a patient NS3 protease domain complexed with the KK4A peptide was 0.044±0.033 µM (Table II). In contrast, the average K$_{i(app,\,1\,h)}$ values of telaprevir were about 11-fold higher for the R155K protease and 9-fold higher for the R155T protease (Table II), the two major variants observed in the phase 1b trial of telaprevir alone. R155S and R155I, two of the minor Arg$^{155}$ variants observed in the telaprevir phase 1b trial, showed 22-fold and 16-fold increases in K$_{i(app,\,1\,h)}$ values, respectively, compared to that of wild-type protease (Table II). These data indicate that substitutions of Arg$^{155}$ with different amino acids, including a conservative substitution of another positively charged residue (Lys), results in a decreased sensitivity to telaprevir.

TABLE II

Demonstration of Resistance in HCV NS3 Protease Enzyme Assays

| Variants | $K_{i(app,1h)}$ of telaprevir (µM) | Fold change |
|---|---|---|
| Wild-type (n = 5) | 0.044 ± 0.033 | 1.0 ± 0.8 |
| R155K (n = 4) | 0.49 ± 0.22 | 11 ± 5 |
| R155T (n = 5) | 0.38 ± 0.18 | 8.7 ± 4.2 |
| R155S (n = 3) | 0.97 ± 0.70 | 22 ± 16 |
| R155I (n = 3) | 0.71 ± 0.35 | 16 ± 8 |

The average $K_{i(app,\,1\,h)}$ values and SD of telaprevir were determined for the purified wild-type and for four variant HCV NS3 serine protease domains using the KK4A cofactor peptide and the FRET substrate in three to five independent experiments. Fold change was determined by dividing the $K_{i(app,\,1\,h)}$ of a given variant by that of the wild-type protease.

3) X-ray Structure of the R155K HCV NS3 Protease

To understand why substitution of $Arg^{155}$ with another residue, including a positively charged amino acid (Lys), results in a loss of sensitivity to telaprevir, the X-ray crystal structure of the R155K NS3 protease was determined. The R155K mutation was engineered into a T7-tag fused HCV-H protease construct that had previously been used to determinate the structure of the wild-type protease co-complexed with NS4A cofactor peptide. The ensemble structure of the R155K protease domain co-complexed with NS4A cofactor peptide, with a resolution of 2.5 Å, is very similar to that of wild-type HCV-H strain protease complex described previously (Kim et al., supra). Briefly, one molecule of NS3 protease domain (residues 1 to 181) and one molecule of the co-factor NS4A (residues 21 to 39) form the globular entity, which, in turn, forms the homodimer with another globular entity in the asymmetrical unit. One globular unit of the $Lys^{155}$ variant protease in complex with the NS4A cofactor was superimposed with the wild-type $Arg^{155}$ co-complex. Because the rms deviation of Cα atoms was only 0.314 Å, there is little difference in structure of these two proteases.

Figure 25:
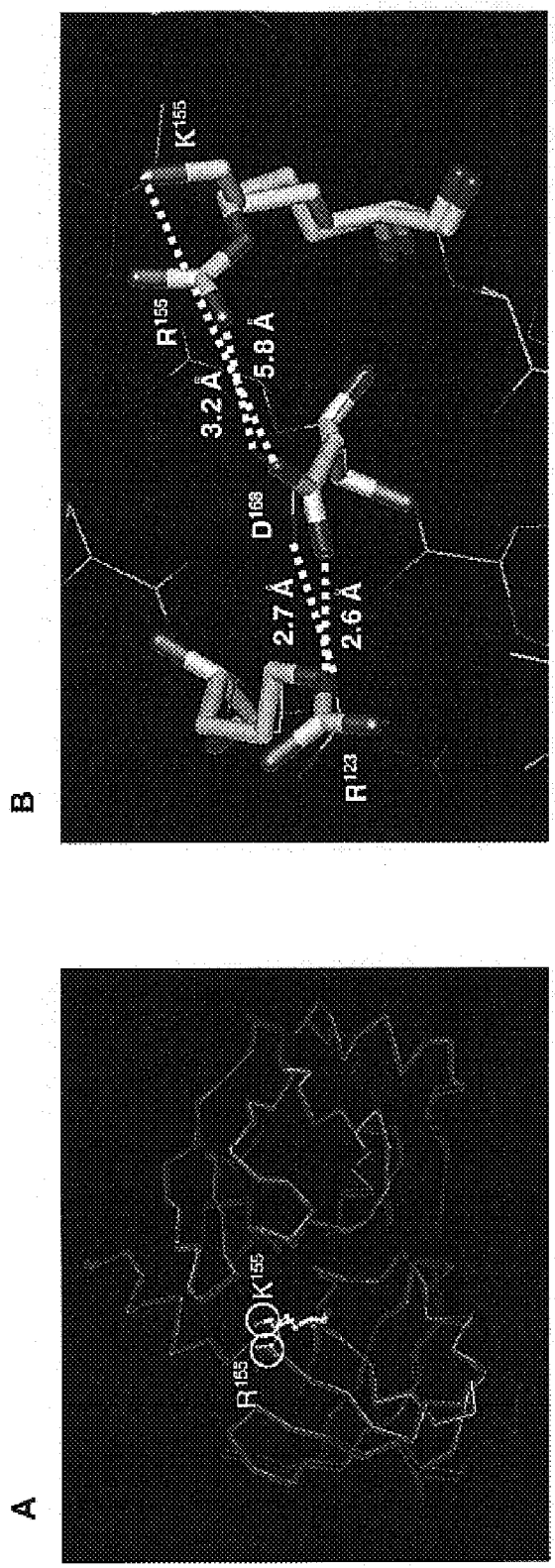
FIG. 25 shows results of structural studies: (A) Superimposition of the X-ray structure of the $Lys^{155}$ variant and the $Arg^{155}$ wild-type NS3 protease domain in a complex with the NS4A co-factor. The Cα atom traces of both the wild-type (in blue) and the R155K variant (in red) proteases are shown as lines. The residue 155 is highlighted with either ball and stick model ($Arg^{155}$) or Liquorice model ($Lys^{155}$) with nitrogens in blue and oxygens in red. (B) Superposition of side chains of $Arg^{155}$, $Asp^{168}$ and $Arg^{123}$ in the wild type NS3-4A with that of corresponding $Lys^{155}$, $Asp^{168}$ and $Arg^{123}$ in the R155K variant. Three residues of the R155K variant protease ($Arg^{123}$, $Asp^{168}$, and $Lys^{155}$) are shown in the Liquorice model, so is the $Arg^{155}$ of the wild-type protease. The $Arg^{123}$ and $Asp^{168}$ residues of the wild-type protease are shown as thin lines. All nitrogens are colored in blue and oxygens in red.

A close-up view of the side chains of NS3 protease residues 123, 168 and 155 in the S2 and S4 pockets is shown in FIG. 25(B). The overall shift of residue 155 side-chain ($Lys^{155}$ versus $Arg^{155}$) is small as evidenced by the distance between the Cδ of residue 155 and the Cβ of the $Asp^{81}$, one of the catalytic triad residues: 4.26 Å for $Lys^{155}$ and 4.24 Å for $Arg^{155}$. In the R155K protease, the distance between the terminal amine (Nz) of $Lys^{155}$ and the Cβ of $Asp^{81}$ is 3.5 Å, and the distance between the Cδ of $Lys^{155}$ and the Cβ of $Asp^{81}$ is 3.6 Å. In the wild-type protease, the NH1 and Nz of $Arg^{155}$ are 5.6 Å and 5.3 Å, respectively, away from the Cβ of its $Asp^{81}$. Thus, the terminal amine group of $Lys^{155}$ in the R155K protease is closer to the carboxyl group of $Asp^{81}$ than the comparative terminal azide group of $Arg^{155}$. In contrast, the distance between Nz of $Lys^{155}$ and the carboxyl atom Oε2 of $Asp^{168}$ is 5.8 Å in the R155K protease compared to 3.2 Å between the corresponding pair of the terminal NH2 of $Arg^{155}$ and the Oε2 of $Asp^{168}$ in the wild-type protease. Thus, the terminal amine group of $Lys^{155}$ in the R155K protease is further away from the carboxyl group of $Asp^{168}$ than the comparative terminal azide group of $Arg^{155}$. Therefore, substitution of Arg with Lys at residue 155 alters the shape of the S2 binding pocket such that the positive charge at the Nz atom of $Lys^{155}$ can not be neutralized by the adjacent side-chain of $Asp^{168}$ as is the case of the wild-type $Arg^{155}$ and $Asp^{168}$ pair.

4) Mechanism of Resistance of R155K or R155T Variant to Telaprevir

Figure 26:
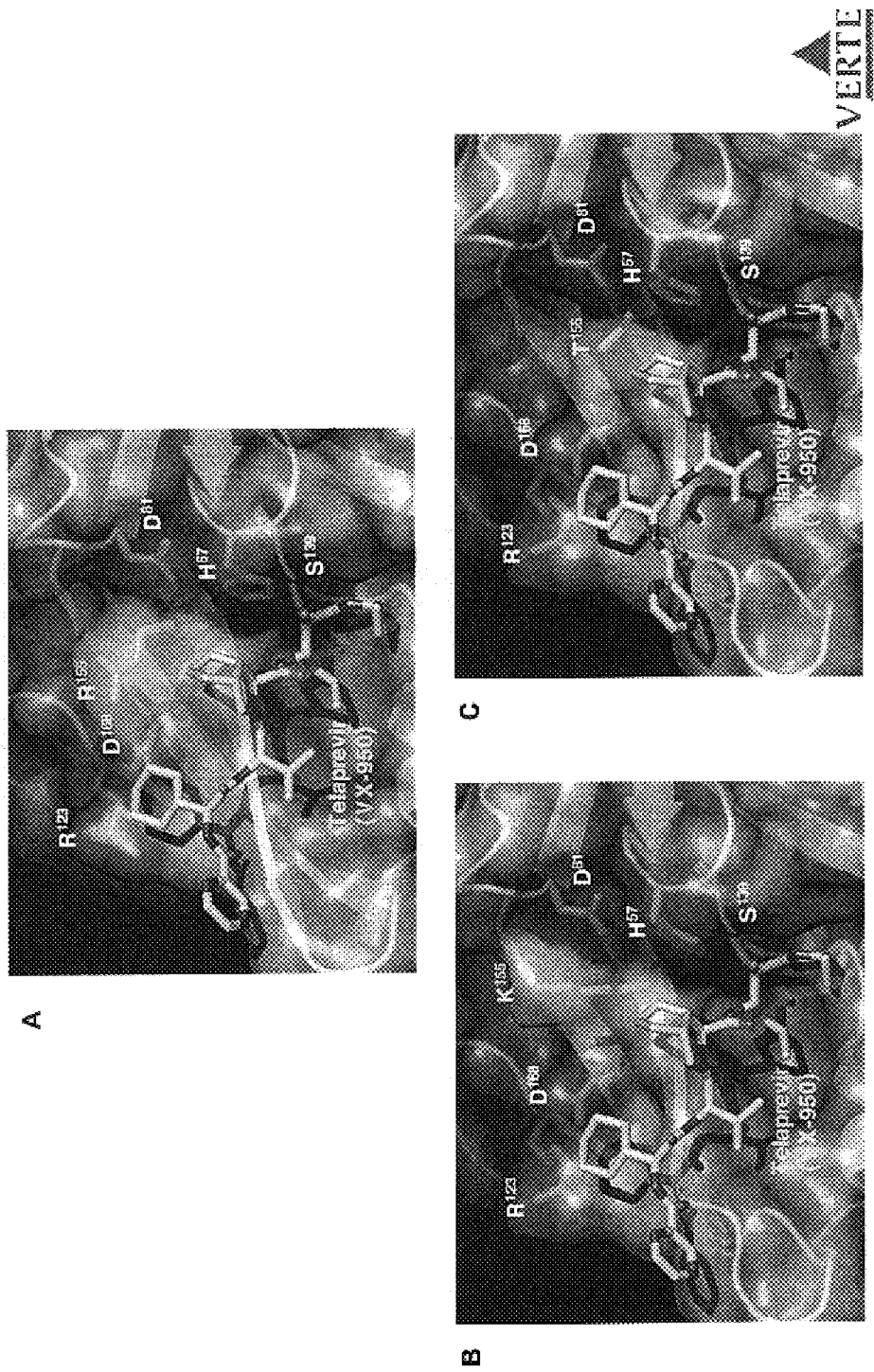
FIG. 26 shows computational models of a co-complex of telaprevir with the HCV NS3 protease domains in a complex with an NS4A cofactor. In all three models, including the wild-type (A), R155K (B) or R155T (C) variant proteases, telaprevir is shown in a stick diagram colored in light blue with nitrogens in blue and oxygens in red. The active site residues ($His^{57}$, $Asp^{81}$, and $Ser^{139}$) are shown as gray sticks. The $Arg^{123}$ and $Asp^{168}$ residues are colored in purple, while residue 155 side-chain is colored in yellow. The $Lys^{155}$ or $Thr^{155}$ side-chain remains in the extended conformation making minimal contacts with the P2 group of telaprevir.
Figure 27:
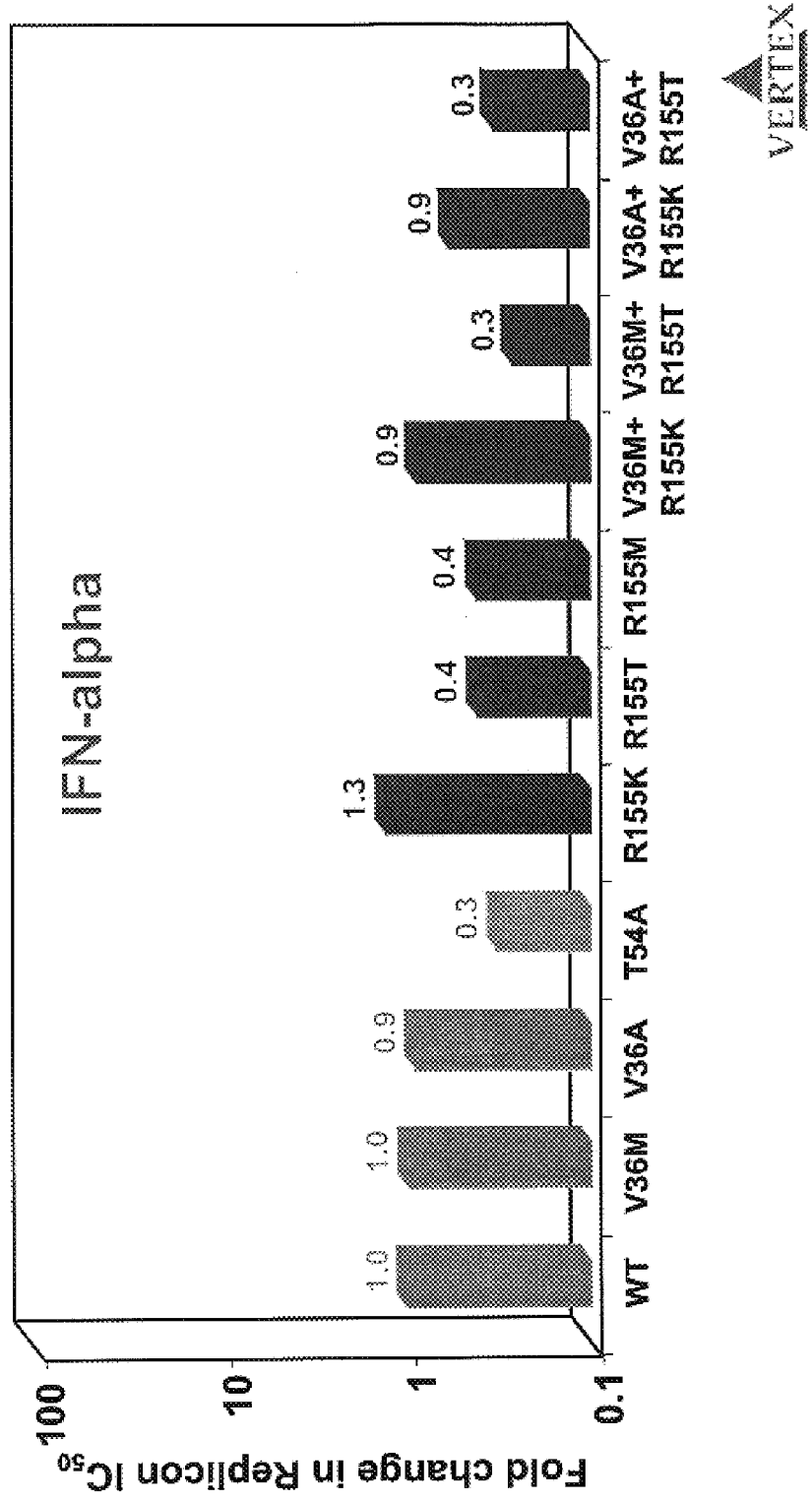
FIG. 27 shows that the VX-950 resistant replicon variants remain fully sensitive to IFN-alpha.
Figure 29:
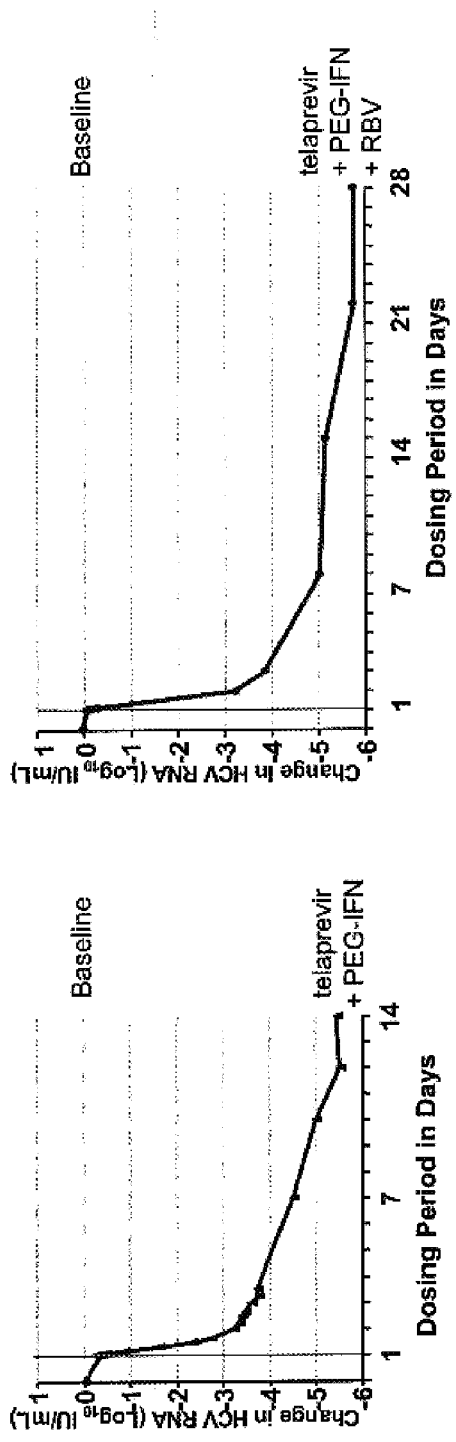
FIG. 29 shows that VX-950 combination therapy suppressed emergence of viral resistance and prevented viral breakthrough during dosing.

A structural model of the interactions between telaprevir and NS3 protease has previously been described (e.g., Lin et al., supra). In a model of the co-complex of telaprevir with the R155K enzyme, the same interactions were maintained except for differences at the side-chain of residue 155. In the wild-type protease structure, the $Arg^{155}$ side-chain bends over the bicyclic P2 group of telaprevir to make several direct van der Waals contacts, and provides a hydrophobic environment for the P2 group of telaprevir (FIG. 26(A)). However, the $Lys^{155}$ side-chain of the R155K enzyme has an extended conformation and makes only one or two direct contacts with the P2 group, thus leaving the P2 group of telaprevir more exposed to the solvent (FIG. 26(B)). This observation is consistent with the R155K enzyme being less sensitive to telaprevir, as shown with in vitro enzyme assays. It is reasonable to assume that the R155M variant will have an extended conformation of $Met^{155}$ side-chain, and therefore similarly fewer interactions with the P2 group of telaprevir, consistent with observed decrease in binding of the inhibitor.

To understand the mechanism of binding of telaprevir to variants with residues with shorter side-chains at position 155, the model of R155T variant enzyme complexed with telaprevir was used. It is obvious from the model that $Thr^{155}$ side-chain is too short to provide a hydrophobic cover for the P2 group of the inhibitor (FIG. 26(C)). Other shorter side-chains like Ile, Ser and Gly are similar or even shorter in size and are expected to lose interactions with the P2 group and have a decreased binding affinity to the telaprevir.

5) HCV Variant Replicons with Substitutions at $Arg^{155}$ of the NS3 Protease Remain Fully Sensitive to IFN-α

Whether the telaprevir-resistant variant replicon cells with substitution at NS3 residue 155 remain sensitive to IFN-α or ribavirin was also determined. As shown in Table III, the $IC_{50}$ of either IFN-α or ribavirin remained virtually the same for HCV replicon cells containing R155K, R155T, or R155M mutations compared to the wild-type replicon cells. These results suggest that combination with IFN-α with or without ribavirin could be a potential therapeutic strategy to suppress the emergence of HCV variants with substitutions at NS3 protease residue 155.

TABLE III

Lack of Resistance to Other Anti-HCV Agents in HCV Replicon Cells

| | Replicon $IC_{50}$ | | | |
|---|---|---|---|---|
| Variants | IFN-α (U/ml) | Fold change | Ribavirin (µM) | Fold change |
| Wild-type | 11.6 ± 1.1 | 1.0 ± 0.1 | 58 ± 18 | 1.0 ± 0.3 |
| R155K | 15.2 ± 12.3 | 1.3 ± 1.1 | 37 ± 17 | 0.6 ± 0.3 |
| R155T | 4.8 ± 3.3 | 0.4 ± 0.3 | 32 ± 18 | 0.6 ± 0.3 |
| R155M | 4.9 ± 1.0 | 0.4 ± 0.1 | 39 ± 5 | 0.7 ± 0.1 |

The stable wild-type and variant HCV sub-genomic replicon cell lines were generated using the T7 RNA runoff transcripts from the corresponding high efficiency Con1 replicon plasmids. The average $IC_{50}$ values and SD of IFN-α and ribavirin were determined for the HCV replicon cell lines in the 48-h assay in three independent experiments. Fold change was determined by dividing the $IC_{50}$ of a given variant by that of the wild-type HCV replicon.

Example 20

Summary of the Study Results

One study was to monitor the possible emergence of drug resistant mutations to VX-950 monotherapy by sequence analysis of the HCV protease NS3-4A region in subjects with genotype 1 hepatitis C who were dosed with VX-950 for 14 days. Traditionally, resistance genotyping has been done by population-based sequencing, which detects the dominant sequence in the plasma virus. Any sequences that constitute less than 20% of the viral population will not be detected by this method. Because drug-resistance mutations may take longer than 14 days to accumulate to this measurable level, a new method was developed to detect minor populations of variants. Sequences were obtained from about 80-85 individual viral clones per subject per time point, so that resistant mutations that may emerge in 14 days of dosing with VX-950 with a sensitivity of down to about 5% of the population can be identified.

In subjects grouped by viral response to VX-950, distinct mutational patterns were observed. In the first group of subjects whose HCV RNA rebounded during the dosing period, wild-type virus was almost completely replaced by 1 of 3 viral variants containing a mutation at position 36, 54, or 155 at ETR and follow up. A V36A mutation was found in genotype 1b subjects, whereas a V36A/M or R155K/T was seen in the genotype 1a subjects. Some variants also contained a double mutation at positions 36 and 155 in 1a subjects. A T54A mutation was seen in both 1a and 1b subtypes. The mutations at positions 36 and 54 appear to be mutually exclusive as they were rarely found together in the same genome. A second group of subjects had an initial HCV RNA decline that leveled off at the end of the 14-day dosing period. These subjects harbored virus that contained a mutation at position 156 from an alanine to either a valine (A156V) or threonine (A156T). This mutation at position 156 has previously been shown to develop in vitro in the presence of VX-950 (6, 7). Some subjects harbored a few variants that also contained a double mutation at positions 36 and 156.

Subject-specific protease clones were expressed and tested for inhibition by VX-950. There were no significant differences in the enzyme $IC_{50}$ values of the baseline proteases derived from different subject isolates within a subtype. However, the IC50 values of the mutant proteases indicate varying degrees of decreased sensitivity to VX-950. HCV RNA in the last group of subjects continued to decline throughout the dosing period, and some reached levels below the limit of detection of the current assay (10 IU/mL). Due to the limit of sensitivity of our sequencing assay (>100 IU/mL), no viral sequence data are available for these subjects at Day 14 of dosing. However, samples taken 7 to 10 days after the last dose of VX-950 were successfully sequenced for all subjects. In the follow-up samples from the first two response groups, resistant mutations were found to persist in the plasma of all subjects. However, in many cases, the frequency of mutation at position 156 was significantly decreased, as the wild-type as well as the mutations at position 36 or 54 began to increase in proportion. The proportion of virions with a mutation at position 155 remained relatively constant. These shifts in mutation patterns are likely due to fitness differences between variants in the absence of drug selective pressure. It appears that viruses with mutation at positions 36, 54, or 155, although less fit than wild-type, are still reasonably fit, whereas the residue 156 mutants are quite unfit in the absence of drug. From these data, there seems to be an inverse correlation between the level of resistance and the fitness for different single mutants. The data derived from the group of subjects with a plateau in plasma HCV RNA indicated the influences of virologic resistance and fitness in producing a given clinical response. Thus, the clinical response cannot, itself, indicate the underlying virology.

Analysis of the last group of subjects who had continued HCV RNA decline during dosing and reached low levels of HCV RNA reveals that virus present at follow-up consisted of mostly low level resistance mutations at positions 36 and 54, and 3 of the subjects harbored few mutations but were mostly or completely wild-type. Although it is unknown what variants, if any, were present at Day 14, this result suggests that with an optimal response to VX-950, it may be possible to avoid clinical resistance with monotherapy or by the addition of other antiviral compounds such as Peg-IFN. Optimizing dosing regimens may extend this response to a greater number of patients.

In summary, these results indicate that the dosing regimen of VX-950 in this study can result in the selection of different mutations in the NS3 protease with varying levels of drug resistance. Increased concentrations of VX-950 are expected to prevent emergence of virus with low level resistance (at positions 36, 54, and 155). The remaining high level resistant virus (at position 156) may be overcome through different treatment options, including combination therapy. Higher drug concentrations may inhibit viral replication more completely, causing a steeper slope of initial decline; thus reducing the chance that resistant mutations will be selected and cause clinical resistance. The addition of Peg-IFN to VX-950 treatment may enhance immune-mediated clearance of the virus, and the effectiveness of immune-mediated clearance should not be affected by the presence of resistant variants. Although the mutation at position 156 confers high levels of resistance, it appears to come with significant fitness costs, as measured by its relative rate of replication in the absence of VX-950. There is increasing evidence that antiviral drug resistance is associated with impaired viral fitness, which can translate into a clinical benefit (1-3, 9). Resistant virus replicating at such a low level may not accumulate compensatory fitness mutations immediately, allowing the host immune system or other drugs, such as Peg-IFN, to clear the remaining virus.

REFERENCES

1. Brenner, B. G., D. Turner, and M. A. Wainberg. 2002. HIV-1 drug resistance: can we overcome? Expert Opin. Biol. Ther. 2:751-61.
2. Buckheit, R. W., Jr. 2004. Understanding HIV resistance, fitness, replication capacity and compensation: targeting viral fitness as a therapeutic strategy. Expert Opin. Investig. Drugs 13:933-58.
3. Gilbert, C., J. Bestman-Smith, and G. Boivin. 2002. Resistance of herpesviruses to antiviral drugs: clinical impacts and molecular mechanisms. Drug Resist. Updat. 5:88-114.
4. Grossman, T. H., E. S. Kawasaki, S. R. Punreddy, and M. S. Osburne. 1998. Spontaneous cAMP-dependent derepression of gene expression in stationary phase plays a role in recombinant expression instability. Gene 209:95-103.
5. Johnson, V. A., F. Brun-Vezinet, B. Clotet, B. Conway, R. T. D'Aquila, L. M. Demeter, D. R. Kuritzkes, D. Pillay, J. M.

Schapiro, A. Telenti, and D. D. Richman. 2004. Update of the drug resistance mutations in HIV-1: 2004. Top. HIV Med. 12:119-24.

6. Lin, C., C. A. Gates, B. G. Rao, D. L. Brennan, J. R. Fulghum, Y.-P. Luong, J. D. Frantz, K. Lin, S. Ma, Y.-Y. Wei, R. B. Perni, and A. D. Kwong. 2005. In vitro studies of cross-resistance mutations against two hepatitis C virus serine protease inhibitors, VX-950 and BILN 2061. J. Biol. Chem. 280:36784-36791.

7. Lin, C., K. Lin, Y. P. Luong, B. G. Rao, Y. Y. Wei, D. L. Brennan, J. R. Fulghum, H. M. Hsiao, S. Ma, J. P. Maxwell, K. M. Cottrell, R. B. Perni, C. A. Gates, and A. D. Kwong. 2004. In vitro resistance studies of hepatitis C virus serine protease inhibitors, VX-950 and BILN 2061: Structural analysis indicates different resistance mechanisms. J. Biol. Chem. 279:17508-17514.

8. Lu, L., T. J. Pilot-Matias, K. D. Stewart, J. T. Randolph, R. Pithawalla, W. He, P. P. Huang, L. L. Klein, H. Mo, and A. Molla. 2004. Mutations conferring resistance to a potent hepatitis C virus serine protease inhibitor in vitro. Antimicrob. Agents Chemother. 48:2260-6.

9. Maisnier-Patin, S., and D. I. Andersson. 2004. Adaptation to the deleterious effects of antimicrobial drug resistance mutations by compensatory evolution. Res. Microbiol. 155:360-9.

10. Pawlotsky, J. M., and J. G. McHutchison. 2004. Hepatitis C. Development of new drugs and clinical trials: promises and pitfalls. Summary of an AASLD hepatitis single topic conference, Chicago, Ill., Feb. 27-Mar. 1, 2003. Hepatology 39:554-67.

11. Simmonds, P. 2004. Genetic diversity and evolution of hepatitis C virus—15 years on. J. Gen. Virol. 85:3173-88.

12. Strader, D. B., T. Wright, D. L. Thomas, and L. B. Seeff. 2004. Diagnosis, management, and treatment of hepatitis C. Hepatology 39:1147-71.

13. Trozzi, C., L. Bartholomew, A. Ceccacci, G. Biasiol, L. Pacini, S. Altamura, F. Narjes, E. Muraglia, G. Paonessa, U. Koch, R. De Francesco, C. Steinkuhler, and G. Migliaccio. 2003. In vitro selection and characterization of hepatitis C virus serine protease variants resistant to an active-site peptide inhibitor. J. Virol. 77:3669-79.

TABLE 1

Mutations in the HCV Protease Alone or in Combination Found After Dosing with VX-950

| Subject Group | Subj ID | VX-950 Dose | Genotype | Δ in VL[a] | Time Point[b] | % Single[c] | | | | % Double[c] | | Average Phenotyped[d] |
|---|---|---|---|---|---|---|---|---|---|---|---|---|
| | | | | | | V36 | T54 | R155 | A156 | 36/155 | 36/156 | |
| Rebound | 2101 | 450 | 1a | 2.56 | ETR[e] | 9 | 4 | 13 | 0 | 77 | 0 | 36.70 |
| | | | | | FU[f] | 23.5 | 0 | 11.5 | 0 | 60.5 | 0 | 29.43 |
| | 2102 | 450 | 1a | 1.84 | ETR | 35 | 3 | 32 | 8 | 12 | 3 | 69.69 |
| | | | | | FU | 31 | 0 | 26 | 0 | 26 | 0 | 14.81 |
| | 2105 | 450 | 1b | 1.06 | ETR | 86 | 0 | 0 | 5 | 0 | 0 | 26.31 |
| | | | | | FU | 45 | 32 | 0 | 6 | 0 | 0 | 28.94 |
| | 2107 | 450 | 1b | 2.09 | ETR | n/a[g] | n/a | n/a | n/a | n/a | n/a | n/a |
| | | | | | FU | n/a | n/a | n/a | n/a | n/a | n/a | n/a |
| | 3108 | 450 | 1b | 2.08 | ETR | 66 | 31 | 0 | 0 | 0 | 0 | 6.03 |
| | | | | | FU | 62 | 8 | 0 | 0 | 0 | 0 | 3.13 |
| | 3111 | 450 | 1b | 1.82 | ETR | 24 | 67 | 0 | 2 | 0 | 1 | 30.71 |
| | | | | | FU | 31 | 63 | 0 | 0 | 0 | 0 | 8.65 |
| | 2211 | 750 | 1a | 2.35 | ETR | n/a | n/a | n/a | n/a | n/a | n/a | n/a |
| | | | | | FU | 35 | 1 | 31 | 0 | 13 | 0 | 9.33 |
| | 2310 | 1250 | 1a | 0.86 | ETR | 42 | 0 | 33 | 0 | 14 | 0 | 10.15 |
| | | | | | FU | 41 | 1 | 22 | 0 | 14 | 0 | 9.39 |
| | 2312 | 1250 | 1a | 3.20 | ETR | 38 | 14 | 9 | 0 | 52 | 0 | 26.13 |
| | | | | | FU | 36 | 9 | 10 | 0 | 52 | 0 | 26.03 |
| | 3301 | 1250 | 1a | 1.16 | ETR | 8 | 4 | 65 | 0 | 10 | 0 | 9.38 |
| | | | | | FU | 28 | 0 | 34 | 0 | 16 | 0 | 10.65 |
| | 3302 | 1250 | 1a | 2.50 | ETR | 39 | 8 | 15 | 0 | 24 | 0 | 14.39 |
| | | | | | FU | 31 | 10 | 26 | 0 | 18 | 0 | 12.33 |
| | 3303 | 1250 | 1a | 1.93 | ETR | 0 | 1 | 79 | 0 | 20 | 0 | 14.59 |
| | | | | | FU | 6 | 0 | 66 | 0 | 23 | 0 | 15.28 |
| | 3305 | 1250 | 1a | 2.25 | ETR | 63 | 2 | 10 | 0 | 12 | 4.5 | 47.49 |
| | | | | | FU | 77 | 0 | 4 | 0 | 10 | 1 | 15.38 |
| Plateau | 2104 | 450 | 1a | 0.65 | ETR | 34 | 0 | 27 | 4 | 9 | 4 | 57.05 |
| | | | | | FU | 82 | 0 | 0 | 0 | 8 | 0 | 6.55 |
| | 2106 | 450 | 1b | 0.41 | ETR | n/a | n/a | n/a | n/a | n/a | n/a | n/a |
| | | | | | FU | 5 | 8 | 0 | 0 | 0 | 0 | 1.14 |
| | 3201 | 750 | 1a | 0.73 | ETR | 0 | 0 | 2 | 100 | 0 | 0 | 466.14 |
| | | | | | FU | 25 | 2 | 24 | 3 | 22 | 3 | 45.74 |
| | 3202 | 750 | 1b | 0.22 | ETR | 0 | 0 | 0 | 100 | 0 | 0 | 466.00 |
| | | | | | FU | 24 | 16 | 0 | 29 | 0 | 2 | 126.48 |
| | 12308 | 1250 | 1b | 0.05 | ETR | 0 | 68 | 0 | 30 | 0 | 0 | 147.96 |
| | | | | | FU | 7 | 64 | 0 | 0 | 0 | 0 | 7.93 |
| | 2309 | 1250 | 1b | 0.33 | ETR | n/a | n/a | n/a | n/a | n/a | n/a | n/a |
| | | | | | FU | 19 | 10 | 0 | 0 | 0 | 0 | 1.87 |
| | 2311 | 1250 | 1a | 0.62 | ETR | 72 | 92 | 12 | 2 | 8 | 1 | 25.96 |
| | | | | | FU | n/a | n/a | n/a | n/a | n/a | n/a | n/a |
| | 3306 | 1250 | 1b | 0.26 | ETR | 0 | 0 | 0 | 100 | 0 | 0 | 466.00 |
| | | | | | FU | 52 | 25 | 0 | 4 | 0 | 1 | 30.97 |
| Continued Response | 3110 | 450 | 1b | — | ETR | nd[h] | nd | nd | nd | nd | nd | nd |
| | | | | | FU | 21 | 53.5 | 0 | 0 | 0 | 0 | 6.80 |
| | 3112 | 450 | 1b | — | ETR | nd | nd | nd | nd | nd | nd | nd |
| | | | | | FU | 3 | 6 | 0 | 0 | 0 | 0 | 0.83 |

TABLE 1-continued

Mutations in the HCV Protease Alone or in Combination Found After Dosing with VX-950

| Subject Group | Subj ID | VX-950 Dose | Geno-type | Δ in VL[a] | Time Point[b] | % Single[c] V36 | T54 | R155 | A156 | % Double[c] 36/155 | 36/156 | Average Phenotype[d] |
|---|---|---|---|---|---|---|---|---|---|---|---|---|
| | 2207 | 750 | 1b | — | ETR | nd | nd | nd | nd | nd | nd | nd |
| | | | | | FU | n/a | n/a | n/a | n/a | n/a | n/a | n/a |
| | 3203 | 750 | 1b | — | ETR | nd | nd | nd | nd | nd | nd | nd |
| | | | | | FU | 9 | 1 | 0 | 2 | 0 | 0 | 9.65 |
| | 3204 | 750 | 1b | — | ETR | nd | nd | nd | nd | nd | nd | nd |
| | | | | | FU | 25 | 20 | 0 | 0 | 0 | 0 | 3.17 |
| | 3205 | 750 | 1a | — | ETR | nd | nd | nd | nd | nd | nd | nd |
| | | | | | FU | 62 | 11 | 21 | 0 | 5 | 0 | 4.92 |
| | 3212 | 750 | 1b | — | ETR | nd | nd | nd | nd | nd | nd | nd |
| | | | | | FU | 0 | 0 | 0 | 0 | 0 | 0 | 0.00 |

[a]Log change in HCV RNA from nadir to Day 14 (end of dosing). Patient 3108 did not have a Day 14 HCV RNA value, and so it was inferred using Day 11 and Day 17 values.
[b]Days after first dose of VX-950
[c]Percentages base on an average of 82 clones
[d]Sum of (% mutant at amino acid position) × (average fold change in $IC_{50}$ for amino acid position for all single and double mutants/100
[e]ETR = end of treatment (Day 14)
[f]FU = follow up (7-10 days after ETR)
[g]n/a = not available (in progress)
[h]nd = not detectable

TABLE 2

$IC_{50}$ Analysis of Single and Double Mutants with VX-950 and BILN 2061

| | VX950 | | BILN2061 | |
|---|---|---|---|---|
| Mutation | $IC_{50}$ [nM] | Fold change | $IC_{50}$ [nM] | Fold change |
| V36M | 110 | 1.7 | nd* | nd |
| V36M | 280 | 4.4 | 2.3 | 0.5 |
| V36M | 156 | 2.4 | 2.0 | 0.4 |
| V36L | 140 | 2.2 | 2.1 | 0.5 |
| V36A | 125 | 2.0 | nd | nd |
| V36A | 275 | 4.3 | 2.3 | 0.5 |
| V36A | 250 | 3.9 | 26 | 5.5 |
| V36A | 264 | 4.1 | nd | nd |
| V36A | 444 | 6.9 | 9.1 | 2.0 |
| T54S | 120 | 1.9 | 3.6 | 0.8 |
| T54A | 749 | 12 | 10 | 2.3 |
| R155K | 275 | 4.3 | 632 | 137 |
| R155K | 300 | 4.7 | nd | nd |
| R155K | 410 | 6.4 | >840 | >183 |
| R155M | 425 | 6.6 | nd | nd |
| R155S | 370 | 5.8 | >840 | >183 |
| R155T | 335 | 5.2 | nd | nd |
| R155T | 465 | 7.3 | 696 | 151 |
| R155T | 915 | 14 | 799 | 174 |
| A156S | 1400 | 22 | 7.4 | 1.6 |
| A156T | 21500 | 336 | >840 | >183 |
| A156T | 15000 | 234 | nd | nd |
| A156I | >50000 | >781 | nd | nd |
| A156V | >50000 | >781 | nd | nd |
| A156V | 12500 | 195 | nd | Nd |
| V36A, R155K | 1350 | 21 | nd | nd |
| V36A, R155K | 1800 | 28 | nd | nd |
| V36M, R155K | 3593 | 56 | nd | nd |
| V36M, R155K | 2950 | 46 | >840 | >183 |
| V36M, R155K | 4043 | 63 | nd | nd |
| V36M, R155T | 3810 | 60 | 729 | 158 |
| V36M, A156T | >50000 | >781 | nd | nd |

*nd = not determined

TABLE 3

Mean $IC_{50}$ values for VX-950 of Different Amino Acid Mutations at the Same Position

| Mutation | $IC_{50}$ mean [nM] | $IC_{50}$ SD [nM] | Fold change mean | Fold change SD |
|---|---|---|---|---|
| V36M/L/A | 227 | 106 | 3.5 | 1.7 |
| T54S | 120 | | 1.9 | |
| T54A | 749 | | 12 | |
| R155K/M/S/T | 437 | 204 | 6.8 | 3.2 |
| A156S | 1400 | | 22 | |
| A156T/V/I | 29800 | 18730 | 466 | 293 |
| V36M/A, R155K/T | 2924 | 1116 | 46 | 17 |
| V36M, A156T | >50000 | | >781 | |

TABLE 4

Fitness of Viral Mutants

| Viral Mutation | Fitness | Fold Reduction in Fitness Relative to Wild-type | Fitness (wild-type set to 100) |
|---|---|---|---|
| None (wild-type) | 4.17 | — | 100 |
| V36A/M | 2.82 | −1.48 | 68 |
| R155K/T + V36A/M | 2.0 | −2.09 | 48 |
| T54A | 1.86 | −2.24 | 45 |
| R155K/T | 1.58 | −2.64 | 38 |
| A156V/T | 0.1 | −41.70 | 2.4 |

TABLE 5

Summary of Resistance of Mutant HCV Proteases

| Viral Variant | VX-950 Replicon Assay[a] | VX-950 Enzyme Assay[b] | SCH 503034 Replicon Assay | SCH 503034 Enzyme Assay | BILN 2061 Replicon Assay | BILN 2061 Enzyme Assay | ITMN-191 Replicon Assay | ITMN-191 Enzyme Assay |
|---|---|---|---|---|---|---|---|---|
| V36M | 7.0 (1.6) | 5.8 | 2.7 (0.9) | 4.4 | 1.4 (0.9) | 0.6 | 2.1 | 1.9 |
| V36A | 7.4 (2.2) | — | 3.2 (0.9) | — | 1.7 (1.1) | — | 1.5 | — |
| V36G | 11.2 (0.4) | — | 2.4 (0.3) | — | 1.1 | — | 1.7 | — |
| V36L | 2.2 (0.4) | 2.2 | 1.1 (0.3) | — | 1.5 | — | 0.9 | — |
| T54A | 6.3 (1.7) | — | 3.2 (1.1) | — | 0.9 (0.2) | — | 1.0 | — |
| V36A + T54A | 20.1 (2.9) | — | 4.5 (0.2) | — | 0.6 (0.3) | — | 0.5 (0.1) | — |
| R155K | 7.4 (0.6) | 11 | 6.2 (4.9) | 10 | 355 (213) | >300 | 62.8 | 120 |
| R155T | 19.8 (1.8) | 8.7 | 10.2 (2.4) | — | 645 (173) | 72 | 9.2 | — |
| R155S | 4.1 (0.4) | 22 | 1.8 (0.6) | — | 592 (124) | >310 | 8.0 (0.2) | — |
| R155I | 24.0 (5.2) | 16 | 6.6 (2.1) | — | 36.5 (9.5) | 56 | 1.3 (0.2) | — |
| R155M | 5.5 (0.4) | — | 2.5 (0.3) | — | 42.2 (2.1) | — | — | — |
| R155G | 7.4 (0.5) | — | 2.8 (0.6) | — | 821 (208) | — | 18.7 (3.0) | — |
| V36A + R155K | ~40 | — | 8.3 (0.7) | — | 757 (99) | — | 316 (191) | — |
| V36A + R155T | >62 | — | 21.9 (6.6) | — | 835 (91) | — | 33.0 | — |
| V36M + R155K | ~63 | 74 | 11.3 (5.5) | 39 | 791 (343) | >250 | 263 (155) | 220 |
| V36M + R155T | >62 | — | 21.3 (2.6) | — | 1160 (110) | — | 66.7 | — |
| V36M + A156T | >62 | — | >37 | — | 1986 (1104) | — | 12.0 (2.0) | — |
| A156S | — | 50 | — | 37 | — | 9.7 | — | 10 |
| A156T | — | 410 | — | 310 | — | >310 | — | 12 |
| V170A | 2.6 (0.6) | — | 3.3 (0.6) | — | 1.8 (0.3) | — | ?? | — |
| R109K | 0.8 (0.2) | — | 0.8 (0.2) | — | 1.2 (0.4) | — | ?? | — |

Incorporation by Reference

All publications and patents mentioned herein are hereby incorporated by reference in their entirety as if each individual publication or patent was specifically and individually indicated to be incorporated by reference.

While specific embodiments of the subject disclosure have been discussed, the above specification is illustrative and not restrictive. Many variations of the disclosure will become apparent to those skilled in the art upon review of this specification and the claims below. The full scope of the disclosure should be determined by reference to the claims, along with their full scope of equivalents, and the specification, along with such variations.

We claim:

1. An isolated Hepatitis C Virus (HCV) polynucleotide comprising a nucleic acid sequence encoding a proteolytically active HCV NS3 protease having an encoded amino acid sequence that is at least 60% identical to the amino acid sequence encoded by the region of the nucleic acid sequence of SEQ ID NO:1, from nucleotide position 1 through nucleotide position 543, wherein the nucleic acid sequence has at least one codon alteration, said codon alteration being at the codon position corresponding to codon position 54 of SEQ ID NO:1, said codon alteration resulting in a codon encoding an amino acid different than threonine or alanine at the amino acid position corresponding to position 54 of the HCV NS3 protease amino acid sequence of SEQ ID NO:2.

2. An isolated Hepatitis C Virus (HCV) polynucleotide comprising a nucleic acid sequence encoding a proteolytically active HCV NS3 protease having an encoded amino acid sequence that is at least 60% identical to the amino acid sequence encoded by the region of the nucleic acid sequence of SEQ ID NO:1, from nucleotide position 1 through nucleotide position 543, wherein the nucleic acid sequence has at least one codon alteration, said codon alteration being at the codon position corresponding to position 54, said codon alteration resulting in a nucleic acid encoding a serine at the amino acid position corresponding to position 54 of the HCV NS3 protease amino acid sequence set forth as SEQ ID NO:2.

3. An isolated Hepatitis C Virus (HCV) polynucleotide comprising a nucleic acid sequence encoding a proteolytically active HCV NS3 protease having an encoded amino acid sequence that is at least 60% identical to the amino acid sequence encoded by the region of the nucleic acid sequence of SEQ ID NO:1, from nucleotide position 1 through nucleotide position 543, wherein the nucleic acid sequence has at least one codon alteration, said codon alteration being at the codon position corresponding to codon position 36 of SEQ ID NO:1, the codon alteration resulting in a codon encoding methionine or glycine at the amino acid position corresponding to position 36 of the HCV NS3 protease amino acid sequence of SEQ ID NO:2.

4. An isolated Hepatitis C Virus (HCV) polynucleotide comprising a nucleic acid sequence encoding a proteolytically active HCV NS3 protease having an encoded amino acid sequence that is at least 60% identical to the amino acid sequence encoded by the region of the nucleic acid sequence of SEQ ID NO:1, from nucleotide position 1 through nucleotide position 543, wherein the nucleic acid sequence has at least one codon alteration, said codon alteration being at the codon position corresponding to codon position 155 of SEQ ID NO:1, said codon alteration resulting in a codon encoding an amino acid selected from the group consisting of lysine, threonine, serine, isoleucine, methionine, leucine and glycine at the amino acid position corresponding to position 155 of the HCV NS3 protease amino acid sequence of SEQ ID NO:2.

5. An isolated Hepatitis C Virus (HCV) polynucleotide comprising a nucleic acid sequence encoding a proteolytically active HCV NS3 protease having an encoded amino acid sequence that is at least 60% identical to the amino acid sequence encoded by the region of the nucleic acid sequence of SEQ ID NO:1, from nucleotide position 1 through nucleotide position 543, wherein the nucleic acid sequence has at least one codon alteration, said codon alteration being at the codon position corresponding to codon position 156 of SEQ ID NO:1, said codon alteration resulting in a codon encoding an isoleucine at the amino acid position corresponding to position 156 of the HCV NS3 protease amino acid sequence of SEQ ID NO:2.

6. The polynucleotide of any one of claims 1 and 2-5, wherein said nucleic acid has at least 90% sequence identity with the region of the nucleic acid sequence of SEQ ID NO:1 from nucleotide position 1 through nucleotide position 543.

7. The polynucleotide of any one of claims 1 and 2-5, wherein said nucleic acid has at least 95% sequence identity with the region of the nucleic acid sequence of SEQ ID NO:1 from nucleotide position 1 through nucleotide position 543.

8. The isolated HCV polynucleotide of claim 1, wherein the nucleic acid has at least one additional codon alteration at a codon position selected from the group consisting of codon positions corresponding to codon positions 36, 155 and 156 of SEQ ID NO:1, and combinations thereof.

9. The isolated HCV polynucleotide of claim 3, wherein the nucleic acid has at least one additional codon alteration at a codon position selected from the group consisting of codon positions corresponding to codon positions 155 and 156 of SEQ ID NO:1, and combinations thereof.

10. The isolated HCV polynucleotide of claim 4, wherein the nucleic acid has at least one additional codon alteration at a codon position selected from the group consisting of codon positions corresponding to codon positions 36 and 156 of SEQ ID NO:1, and combinations thereof.

11. The isolated HCV polynucleotide of claim 5, wherein the nucleic acid sequence has at least one additional codon alteration at a codon position selected from the group of codon positions consisting of codon positions corresponding to codon positions 36,54 and 155 of SEQ ID NO:1, or combinations thereof.

12. An expression system comprising the HCV polynucleotide of any one of claims 1 and 2-5.

13. An expression system comprising a vector comprising the HCV polynucleotide of any one of claims 1 and 2-5 operably linked to a promoter.

14. A host cell transfected, transformed, or transduced with the vector of claim 13.

15. The expression system of claim 12 that is an mRNA display system.

16. An isolated Hepatitis C Virus (HCV) polynucleotide, comprising a nucleic acid sequence encoding a HCV NS3 protease capable of binding to either a VX-950 protease inhibitor or a BILN 2061 protease inhibitor in the presence of HCV NS4A peptide cofactor and having at least 60% sequence identity with the amino acid sequence encoded by the region of the nucleic acid sequence of SEQ ID NO:1, from nucleotide position 1 through nucleotide position 543, wherein the nucleic acid sequence has at least one codon alteration at a codon position selected from the group of codon positions corresponding to codon positions 36, 54, 155 and 156 of SEQ ID NO:1, and (i) wherein said codon alteration at the codon position corresponding to codon position 36 of SEQ ID NO:1, if it is the only codon alteration at a position corresponding to one of the codon positions 36, 54, 155 and 156, results in a codon encoding methionine or glycine, (ii) wherein said codon alteration at the codon position corresponding to codon position 54 of SEQ ID NO:1, if it is the only codon alteration at a position corresponding to one of the codon positions 36, 54, 155 and 156, results in a codon encoding a serine, (iii) wherein said codon alteration at the position corresponding to codon position 155 of SEQ ID NO:1, if it is the only codon alteration at a position corresponding to one of the codon positions 36, 54, 155 and 156, results in a codon encoding an amino acid selected from the group consisting lysine, threonine, serine, isoleucine, methionine, leucine and glycine, and (iv) wherein said codon alteration at the position corresponding to codon position 156 of SEQ ID NO:1, if it is the only codon alteration at a position corresponding to one of the codon positions 36, 54, 155 and 156, results in a codon encoding isoleucine.

17. The isolated Hepatitis C Virus (HCV) polynucleotide of claim 16 wherein the nucleic acid sequence comprises a first codon alteration, said codon alteration being at the codon position corresponding to position 36 of SEQ ID NO:1, said codon alteration resulting in a codon encoding methionine or glycine, and that further comprises at least an additional codon alteration at one or more codon positions selected from the group of codon positions corresponding to codon positions 54, 155 and 156.

18. The isolated Hepatitis C Virus (HCV) polynucleotide of claim 16, wherein the nucleic acid sequence comprises a first codon alteration, said codon alteration being at the codon position corresponding to position 155 in the nucleic acid sequence of SEQ ID NO:1, said codon alteration resulting in a codon encoding an amino acid selected from the group consisting lysine, threonine, serine, isoleucine, methionine, leucine and glycine, and that further comprises at least an additional codon alteration at one or more codon positions selected from the group of codon positions corresponding to codon positions 36, 54 and 156.

19. An isolated Hepatitis C Virus (HCV) variant comprising a nucleic acid encoding a proteolytically active HCV NS3 protease having an encoded amino acid sequence that is at least 60% identical to the amino acid sequence encoded by the region of the nucleic acid sequence of SEQ ID NO:1, from nucleotide position 1 through nucleotide position 543, wherein the nucleic acid has at least one codon alteration, said codon alteration being at the codon position corresponding to codon position 36 of SEQ ID NO:1, said codon alteration resulting in a codon encoding methionine or glycine at the amino acid position corresponding to position 36 of the HCV NS3 protease amino acid sequence of SEQ ID NO:2.

20. An isolated Hepatitis C Virus (HCV) variant comprising a nucleic acid encoding a proteolytically active HCV NS3 protease having an encoded amino acid sequence that is at least 60% identical to the amino acid sequence encoded by the region of the nucleic acid sequence of SEQ ID NO:1, from nucleotide position 1 through nucleotide position 543, wherein the nucleic acid sequence has at least one codon alteration at the codon position corresponding to codon position 54 of SEQ ID NO:1, wherein said codon alteration results in a codon encoding an amino acid different than threonine or alanine at the amino acid position corresponding to position 54 of the HCV NS3 protease amino acid sequence SEQ ID NO:2.

21. An isolated Hepatitis C Virus (HCV) variant comprising a nucleic acid encoding a proteolytically active HCV NS3 protease having an encoded amino acid sequence that is at least 60% identical to the amino acid sequence encoded by the region of the nucleic acid sequence of SEQ ID NO:1, from nucleotide position 1 through nucleotide position 543, wherein the nucleic acid has at least one codon alteration, said codon alteration being at the codon position corresponding to codon position 155 of SEQ ID NO:1, said codon alteration resulting in a codon encoding an amino acid selected from the group consisting of lysine, threonine, serine, isoleucine, methionine, leucine and glycine at the amino acid position corresponding to position 155 of the HCV NS3 protease amino acid sequence of SEQ ID NO:2.

22. An isolated Hepatitis C Virus (HCV) variant comprising a nucleic acid encoding a proteolytically active HCV NS3 protease having an encoded amino acid sequence that is at least 60% identical to the amino acid sequence encoded by the region of the nucleic acid sequence of SEQ ID NO:1, from nucleotide position 1 through nucleotide position 543, wherein the nucleic acid has at least one alteration, said codon alteration being at the codon position corresponding to codon position 156 of SEQ ID NO:1, said codon alteration resulting in a codon encoding an isoleucine at the amino acid position corresponding to position 156 of the HCV NS3 protease amino acid sequence of SEQ ID NO:2.

23. The isolated HCV variant of claim 19, wherein the nucleic acid has at least one additional codon alteration at a codon position selected from the group of codon positions consisting of codon positions corresponding to codon positions 54, 155 and 156 of SEQ ID NO:1, and combinations thereof.

24. The isolated HCV variant of claim 20, wherein the nucleic acid has at least one additional codon alteration at a codon position selected from the group of codon positions consisting of codon positions corresponding to codon positions 36, 155 and 156 of SEQ ID NO:1, and combinations thereof.

25. The isolated HCV variant of claim 21, wherein the nucleic acid has at least one additional codon alteration at a codon position selected from the group of codon positions consisting of codon positions corresponding to codon positions 36, 54 and 156 of SEQ ID NO:1, and combinations thereof.

26. The isolated HCV variant of claim 22, wherein the nucleic acid has at least one additional codon alteration at a codon position selected from the group of codon positions consisting of codon positions corresponding to codon positions 36, 54 and 155 of SEQ ID NO:1, and combinations thereof.

27. The variant of any one of claims 20, 19-22, wherein said nucleic acid has at least 90% sequence identity with the region of the nucleic acid sequence of SEQ ID NO:1 from nucleotide position 1 through nucleotide position 543.

28. The variant of any one of claims 20, 19-22, wherein said nucleic acid has at least 95% sequence identity with the region of the nucleic acid sequence of SEQ ID NO:1 from nucleotide position 1 through nucleotide position 543.

* * * * *

SEQUENCE LISTING

```
<160> NUMBER OF SEQ ID NOS: 8

<210> SEQ ID NO 1
<211> LENGTH: 2055
<212> TYPE: DNA
<213> ORGANISM: Hepatitis C virus

<400> SEQUENCE: 1
gcgcctatta cggcctactc ccaacagacg cgaggcctac ttggctgcat catcactagc      60
ctcacaggcc gggacaggaa ccaggtcgag ggggaggtcc aagtggtctc caccgcaaca     120
caatctttcc tggcgacctg cgtcaatggc gtgtgttgga ctgtctatca tggtgccggc     180
tcaaagaccc ttgccggccc aaagggccca atcacccaaa tgtacaccaa tgtggaccag     240
gacctcgtcg gctggcaagc gccccccggg gcgcgttcct tgacaccatg cacctgcggc     300
agctcggacc tttacttggt cacgaggcat gccgatgtca ttccggtgcg ccggcggggc     360
gacagcaggg ggagcctact ctcccccagg cccgtctcct acttgaaggg ctcttcgggc     420
ggtccactgc tctgcccctc ggggcacgct gtgggcatct ttcgggctgc cgtgtgcacc     480
cgaggggttg cgaaggcggt ggactttgta cccgtcgagt ctatggaaac cactatgcgg     540
```

```
tccccggtct tcacggacaa ctcgtcccct ccggccgtac cgcagacatt ccaggtggcc      600
catctacacg cccctactgg tagcggcaag agcactaagg tgccggctgc gtatgcagcc      660
caagggtata aggtgcttgt cctgaacccg tccgtcgccg ccaccctagg tttcggggcg      720
tatatgtcta aggcacatgg tatcgaccct aacatcagaa ccggggtaag gaccatcacc      780
acgggtgccc ccatcacgta ctccacctat ggcaagtttc ttgccgacgg tggttgctct      840 ggggcgcct atgacatcat aatatgtgat gagtgccact caactgactc gaccactatc      900
ctgggcatcg gcacagtcct ggaccaagcg gagacggctg gagcgcgact cgtcgtgctc      960
gccaccgcta cgcctccggg atcggtcacc gtgccacatc caaacatcga ggaggtggct     1020
ctgtccagca ctggagaaat cccctttat ggcaaagcca tccccatcga gaccatcaag     1080
ggggggaggc acctcatttt ctgccattcc aagaagaaat gtgatgagct cgccgcgaag     1140
ctgtccggcc tcggactcaa tgctgtagca tattaccggg gccttgatgt atccgtcata     1200
ccaactagcg gagacgtcat tgtcgtagca acggacgctc taatgacggg ctttaccggc     1260
gatttcgact cagtgatcga ctgcaataca tgtgtcaccc agacagtcga cttcagcctg     1320
gacccgacct tcaccattga cgacgacgac cgtgccacaa g acgcggtgtc acgctcgcag    1380
cggcgaggca ggactggtag gggcaggatg ggcatttaca ggtttgtgac tccaggagaa     1440
cggccctcgg gcatgttcga ttcctcggtt ctgtgcgagt gctatgacgc gggctgtgct     1500
tggtacgagc tcacgcccgc cgagacctca gttaggttgc gggcttacct aaacacacca     1560
gggttgcccg tctgccagga ccatctggag ttctgggaga cgtctttac aggcctcacc      1620 cacatagacg cccatttctt gtcccagact aagcaggcag agacaacttc ccctacctg     1680 gtagcatacc aggctacggt gtgcgccagg gctcaggctc cacctccatc gtgggaccaa     1740
atgtggaagt gtctcatacg gctaaagcct acgctgcacg gccaacgcc cctgctgtat      1800 aggctgggag ccgttcaaaa cgaggttact accacacacc ccataaccaa atacatcatg     1860
gcatgcatgt cggctgacct ggaggtcgtg acgagcacct gggtgctggt aggcggagtc     1920
ctagcagctc tggccgcgta ttgcctgaca acaggcagcg tggtcattgt gggcaggatc     1980
atcttgtccg gaaagccggc catcattccc gacagggaag tcctttaccg ggagttcgat     2040
gagatggaag agtgc                                                      2055
```

<210> SEQ ID NO 2
<211> LENGTH: 685
<212> TYPE: PRT
<213> ORGANISM: Hepatitis C virus

<400> SEQUENCE: 2

```
Ala Pro Ile Thr Ala Tyr Ser Gln Gln Thr Arg Gly Leu Leu Gly Cys
  1               5                  10                  15

Ile Ile Thr Ser Leu Thr Gly Arg Asp Arg Asn Gln Val Glu Gly Glu
             20                  25                  30

Val Gln Val Val Ser Thr Ala Thr Gln Ser Phe Leu Ala Thr Cys Val
         35                  40                  45

Asn Gly Val Cys Trp Thr Val Tyr His Gly Ala Gly Ser Lys Thr Leu
     50                  55                  60

Ala Gly Pro Lys Gly Pro Ile Thr Gln Met Tyr Thr Asn Val Asp Gln
 65                  70                  75                  80

Asp Leu Val Gly Trp Gln Ala Pro Pro Gly Ala Arg Ser Leu Thr Pro
                 85                  90                  95
```

```
Cys Thr Cys Gly Ser Ser Asp Leu Tyr Leu Val Thr Arg His Ala Asp
            100                 105                 110

Val Ile Pro Val Arg Arg Gly Asp Ser Arg Gly Ser Leu Leu Ser
        115                 120                 125

Pro Arg Pro Val Ser Tyr Leu Lys Gly Ser Ser Gly Pro Leu Leu
    130                 135                 140

Cys Pro Ser Gly His Ala Val Gly Ile Phe Arg Ala Ala Val Cys Thr
145                 150                 155                 160

Arg Gly Val Ala Lys Ala Val Asp Phe Val Pro Val Glu Ser Met Glu
                165                 170                 175

Thr Thr Met Arg Ser Pro Val Phe Thr Asp Asn Ser Ser Pro Pro Ala
            180                 185                 190

Val Pro Gln Thr Phe Gln Val Ala His Leu His Ala Pro Thr Gly Ser
        195                 200                 205

Gly Lys Ser Thr Lys Val Pro Ala Ala Tyr Ala Ala Gln Gly Tyr Lys
    210                 215                 220

Val Leu Val Leu Asn Pro Ser Val Ala Ala Thr Leu Gly Phe Gly Ala
225                 230                 235                 240

Tyr Met Ser Lys Ala His Gly Ile Asp Pro Asn Ile Arg Thr Gly Val
                245                 250                 255

Arg Thr Ile Thr Thr Gly Ala Pro Ile Thr Tyr Ser Thr Tyr Gly Lys
            260                 265                 270

Phe Leu Ala Asp Gly Gly Cys Ser Gly Gly Ala Tyr Asp Ile Ile Ile
        275                 280                 285

Cys Asp Glu Cys His Ser Thr Asp Ser Thr Thr Ile Leu Gly Ile Gly
    290                 295                 300

Thr Val Leu Asp Gln Ala Glu Thr Ala Gly Ala Arg Leu Val Val Leu
305                 310                 315                 320

Ala Thr Ala Thr Pro Pro Gly Ser Val Thr Val Pro His Pro Asn Ile
                325                 330                 335

Glu Glu Val Ala Leu Ser Ser Thr Gly Glu Ile Pro Phe Tyr Gly Lys
            340                 345                 350

Ala Ile Pro Ile Glu Thr Ile Lys Gly Gly Arg His Leu Ile Phe Cys
        355                 360                 365

His Ser Lys Lys Lys Cys Asp Glu Leu Ala Ala Lys Leu Ser Gly Leu
    370                 375                 380

Gly Leu Asn Ala Val Ala Tyr Tyr Arg Gly Leu Asp Val Ser Val Ile
385                 390                 395                 400

Pro Thr Ser Gly Asp Val Ile Val Val Ala Thr Asp Ala Leu Met Thr
                405                 410                 415

Gly Phe Thr Gly Asp Phe Asp Ser Val Ile Asp Cys Asn Thr Cys Val
            420                 425                 430

Thr Gln Thr Val Asp Phe Ser Leu Asp Pro Thr Phe Thr Ile Glu Thr
        435                 440                 445

Thr Thr Val Pro Gln Asp Ala Val Ser Arg Ser Gln Arg Arg Gly Arg
    450                 455                 460

Thr Gly Arg Gly Arg Met Gly Ile Tyr Arg Phe Val Thr Pro Gly Glu
465                 470                 475                 480

Arg Pro Ser Gly Met Phe Asp Ser Ser Val Leu Cys Glu Cys Tyr Asp
                485                 490                 495

Ala Gly Cys Ala Trp Tyr Glu Leu Thr Pro Ala Glu Thr Ser Val Arg
            500                 505                 510

Leu Arg Ala Tyr Leu Asn Thr Pro Gly Leu Pro Val Cys Gln Asp His
```

-continued

```
                515                 520                 525
Leu Glu Phe Trp Glu Ser Val Phe Thr Gly Leu Thr His Ile Asp Ala
        530                 535                 540

His Phe Leu Ser Gln Thr Lys Gln Ala Gly Asp Asn Phe Pro Tyr Leu
545                 550                 555                 560

Val Ala Tyr Gln Ala Thr Val Cys Ala Arg Ala Gln Ala Pro Pro Pro
                565                 570                 575

Ser Trp Asp Gln Met Trp Lys Cys Leu Ile Arg Leu Lys Pro Thr Leu
            580                 585                 590

His Gly Pro Thr Pro Leu Leu Tyr Arg Leu Gly Ala Val Gln Asn Glu
        595                 600                 605

Val Thr Thr Thr His Pro Ile Thr Lys Tyr Ile Met Ala Cys Met Ser
    610                 615                 620

Ala Asp Leu Glu Val Val Thr Ser Thr Trp Val Leu Val Gly Gly Val
625                 630                 635                 640

Leu Ala Ala Leu Ala Ala Tyr Cys Leu Thr Thr Gly Ser Val Val Ile
                645                 650                 655

Val Gly Arg Ile Ile Leu Ser Gly Lys Pro Ala Ile Ile Pro Asp Arg
            660                 665                 670

Glu Val Leu Tyr Arg Glu Phe Asp Glu Met Glu Glu Cys
        675                 680                 685

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ggcgtgtggg gacatcatc                                                19

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ggtggagtac gtgatggggc                                               20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
catatacgct ccaaagccca                                               20

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      6x His tag
```

```
<400> SEQUENCE: 6

His His His His His His
  1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: (EDANS)
<220> FEATURE:
<221> NAME/KEY: MOD_RES
<222> LOCATION: (6)
<223> OTHER INFORMATION: alpha-Abu psi[COO]
<220> FEATURE:
<221> NAME/KEY: MOD_RES
<222> LOCATION: (9)
<223> OTHER INFORMATION: (DABCYL)

<400> SEQUENCE: 7

Asp Glu Asp Glu Glu Xaa Ala Ser Lys
  1               5

<210> SEQ ID NO 8
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Lys Lys Gly Ser Val Val Ile Val Gly Arg Ile Val Leu Ser Gly Lys
  1               5                  10                  15
```